US006702834B1

(12) United States Patent
Boylan et al.

(10) Patent No.: US 6,702,834 B1
(45) Date of Patent: Mar. 9, 2004

(54) EMBOLIC PROTECTION DEVICES

(75) Inventors: John F. Boylan, Murrieta, CA (US);
William J. Boyle, Fallbrook, CA (US);
Andy E. Denison, Temecula, CA (US);
Debashis Dutta, Santa Clara, CA (US);
Benjamin C. Huter, Murrieta, CA (US); Scott J. Huter, Temecula, CA (US); Paul F. Muller, San Carlos, CA (US); Samir Patel, Del Mar, CA (US);
Christopher J. Tarapata, Santa Clara, CA (US); Chicheng Wang, Highland Park, NJ (US); Francisco Sanchez, Temecula, CA (US); Kent C. B. Stalker, San Marcos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 152 days.

(21) Appl. No.: 09/727,102

(22) Filed: Nov. 28, 2000

Related U.S. Application Data

(63) Continuation-in-part of application No. 09/490,319, filed on Jan. 24, 2000, which is a continuation-in-part of application No. 09/476,159, filed on Dec. 30, 1999.

(51) Int. Cl.[7] .............................................. A61M 29/00
(52) U.S. Cl. ...................... 606/200; 606/159; 606/127; 604/106
(58) Field of Search ................................ 606/159, 200, 606/110, 113, 114, 127; 604/104–109, 171, 172, 265

(56) References Cited

U.S. PATENT DOCUMENTS

| 3,952,747 A | 4/1976 | Kimmell, Jr. |
| 4,425,908 A | 1/1984 | Simon |
| 4,494,531 A | 1/1985 | Gianturco |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |

(List continued on next page.)

FOREIGN PATENT DOCUMENTS

| EP | 0 472 334 A1 | 2/1992 |
| GB | 2020557 | 11/1979 |
| WO | WO92/03097 | 3/1992 |

(List continued on next page.)

*Primary Examiner*—Brian L. Casler
*Assistant Examiner*—Jennifer Maynard
(74) *Attorney, Agent, or Firm*—Fulwider Patton Lee & Utecht, LLP.

(57) ABSTRACT

An embolic protection device for use in a blood vessel when an interventional procedure is being performed in a stenosed or occluded region to capture any embolic material which may be created and released into the bloodstream during the procedure. The device includes a filtering assembly having a self-expanding strut assembly and a filter element attached thereto. In one embodiment, the filtering assembly is attached to the distal end of a guide wire and is deployed within the patient's vasculature as the guide wire is manipulated into the area of treatment. A restraining sheath placed over the filtering assembly in a coaxial arrangement maintains the filtering assembly in its collapsed position until it is ready to be deployed by the physician. Thereafter, the sheath can be retracted to expose the filtering assembly which will then self-expand within the patient's vasculature. Interventional devices can be delivered over the guide wire and any embolic debris created during the interventional procedure and released into the blood stream will enter the filtering assembly and be captured therein. Other embodiments include filtering assemblies attached to an outer tubular member and inner shaft member which apply axial force to the distal ends of the assembly to either expand or contract the struts as needed.

8 Claims, 30 Drawing Sheets

U.S. PATENT DOCUMENTS

| | | |
|---|---|---|
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,626,605 A | 5/1997 | Irie et al. |
| 5,634,942 A | 6/1997 | Chevillon et al. |
| 5,649,953 A | 7/1997 | Lefebvre |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maahs |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,941,896 A | 8/1999 | Kerr |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,013,093 A | 1/2000 | Nott et al. |
| 6,152,946 A * | 11/2000 | Broome et al. ............ 606/200 |
| 6,171,327 B1 | 1/2001 | Daniel et al. |
| 6,179,859 B1 | 1/2001 | Bates et al. |
| 6,179,860 B1 * | 1/2001 | Fulton, III et al. ......... 606/200 |
| 6,290,710 B1 * | 9/2001 | Cryer et al. ................ 606/200 |
| 6,340,465 B1 * | 1/2002 | Hsu et al. ................... 424/400 |
| 6,383,206 B1 * | 5/2002 | Gillick et al. .............. 606/200 |

FOREIGN PATENT DOCUMENTS

| | | |
|---|---|---|
| WO | WO96/01591 | 1/1996 |
| WO | WO97/17100 | 5/1997 |
| WO | WO98/02084 | 1/1998 |
| WO | WO98/33443 | 8/1998 |
| WO | WO99/23976 | 5/1999 |
| WO | WO 0067667 | 11/2000 |

\* cited by examiner

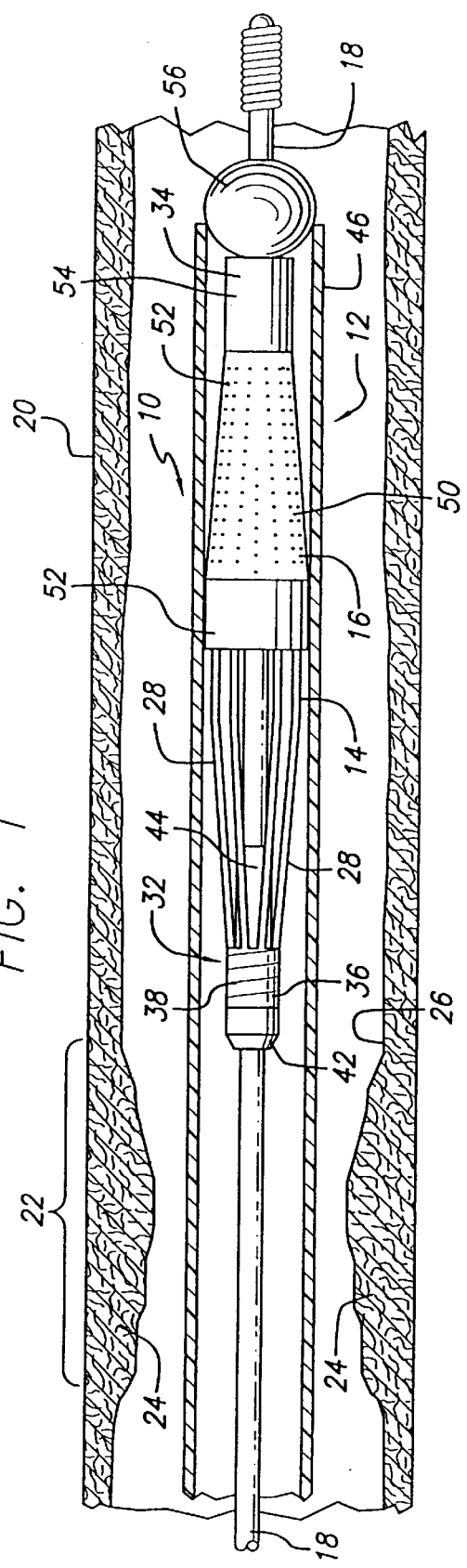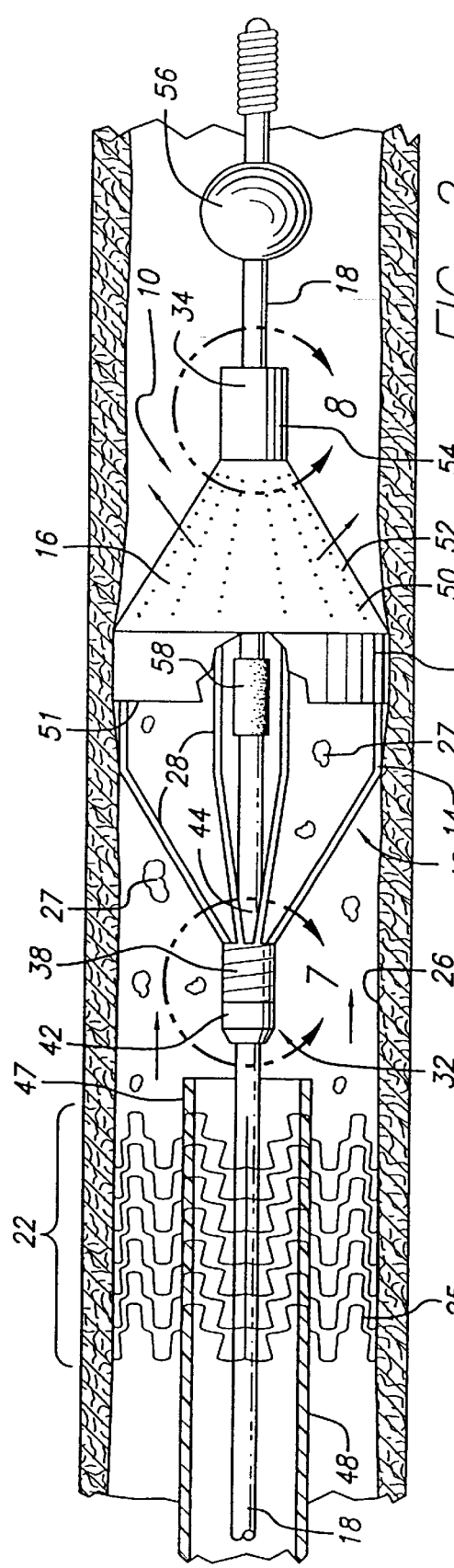

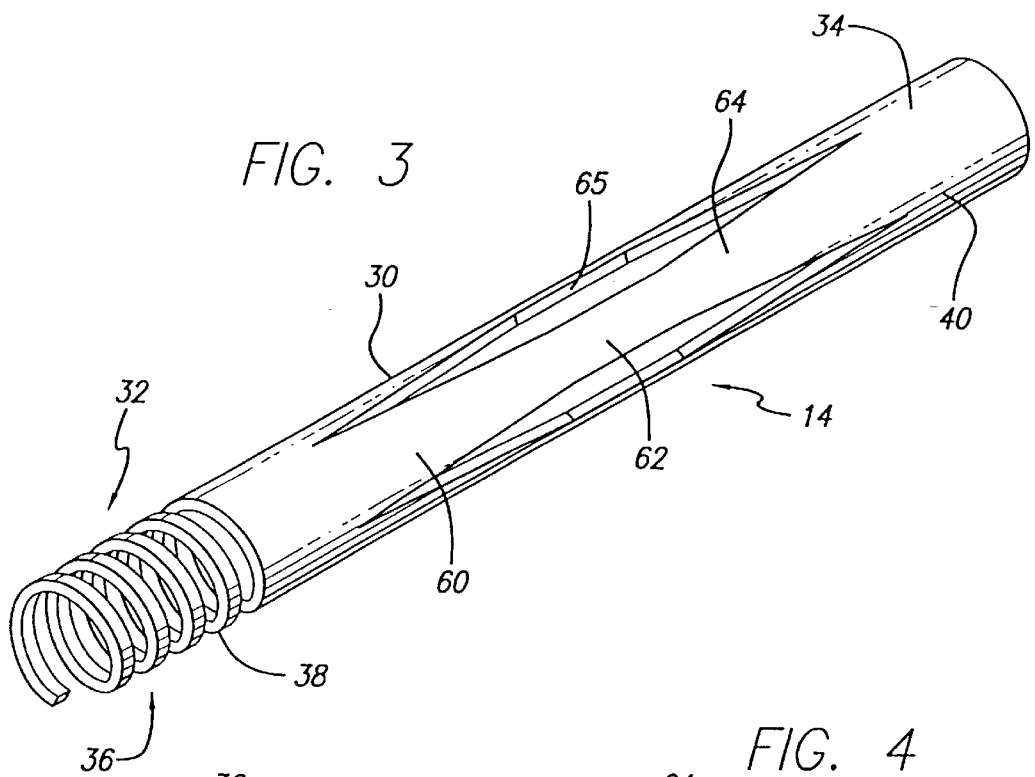
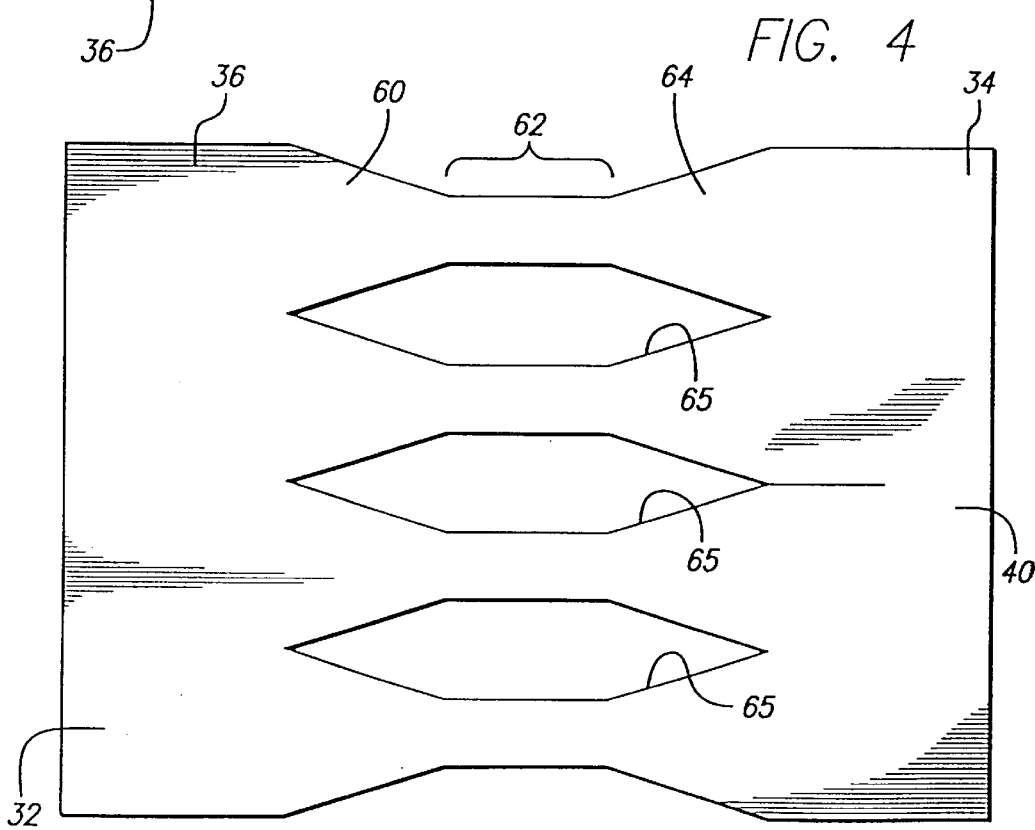

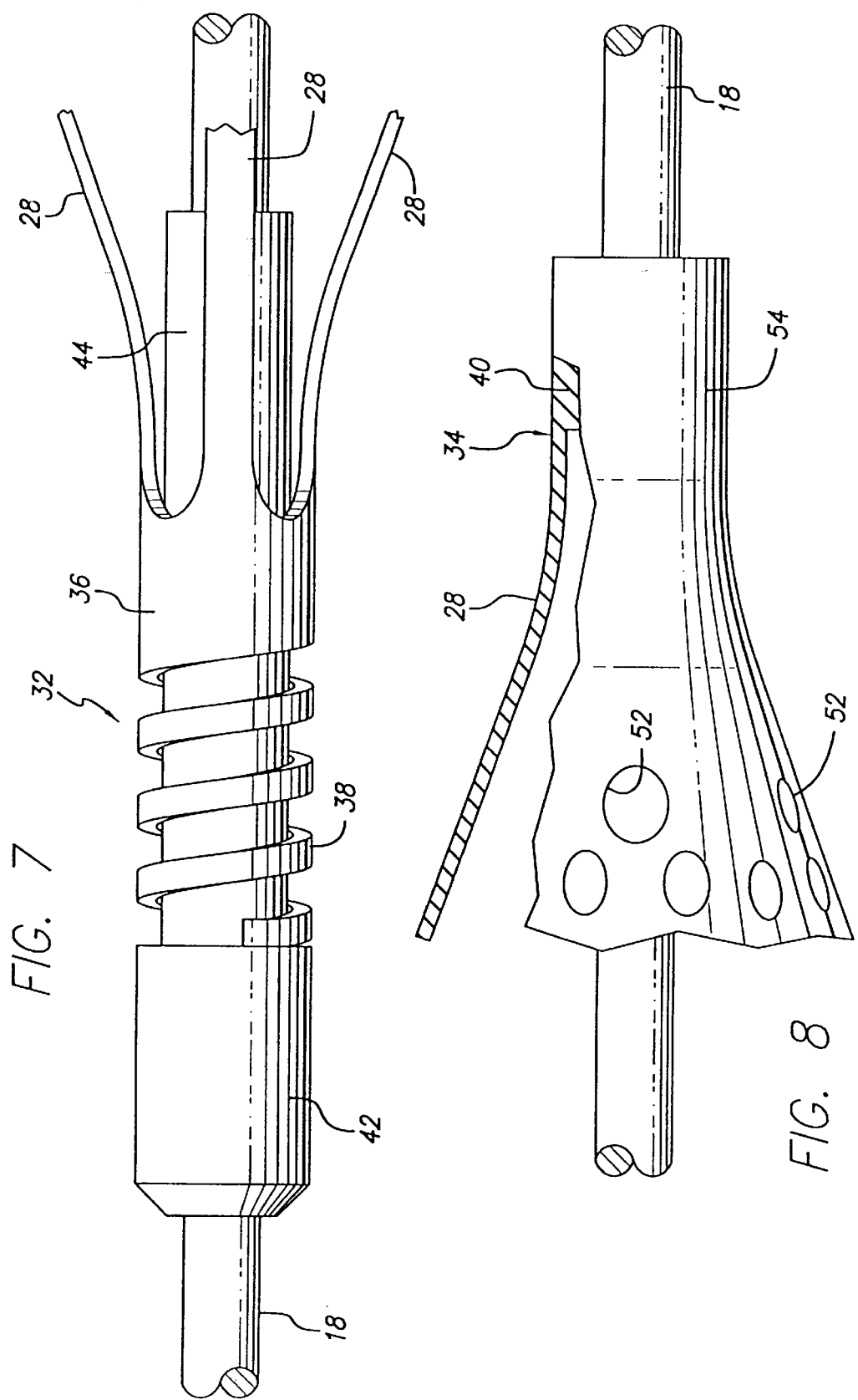

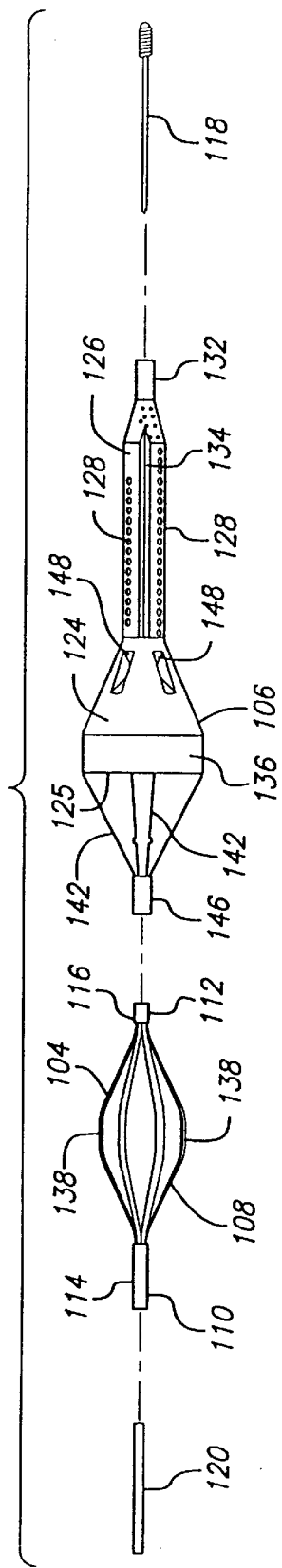
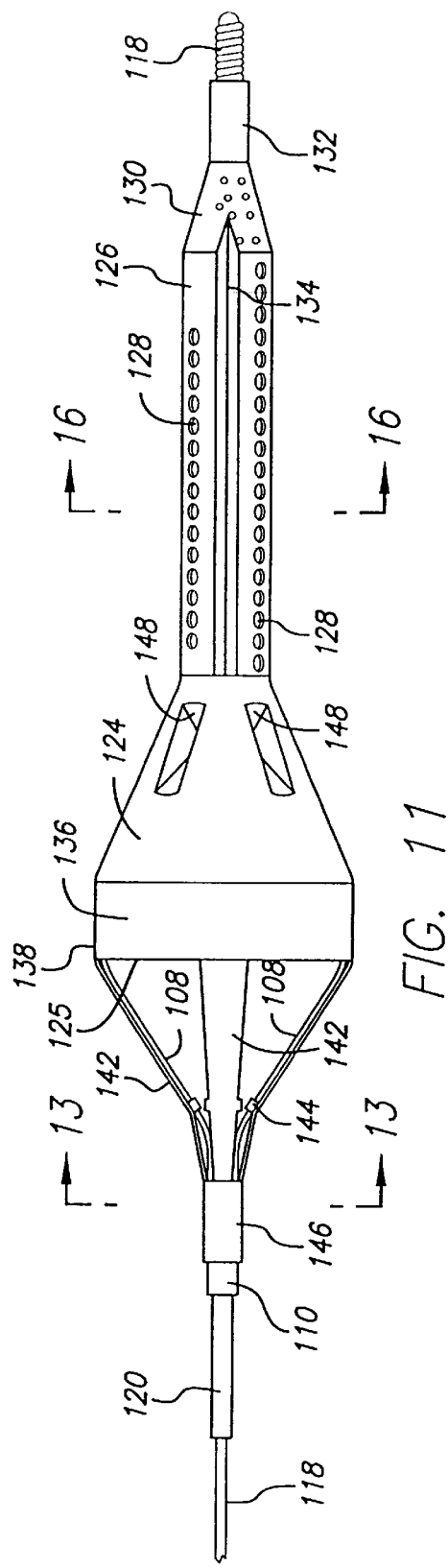
FIG. 10
FIG. 11

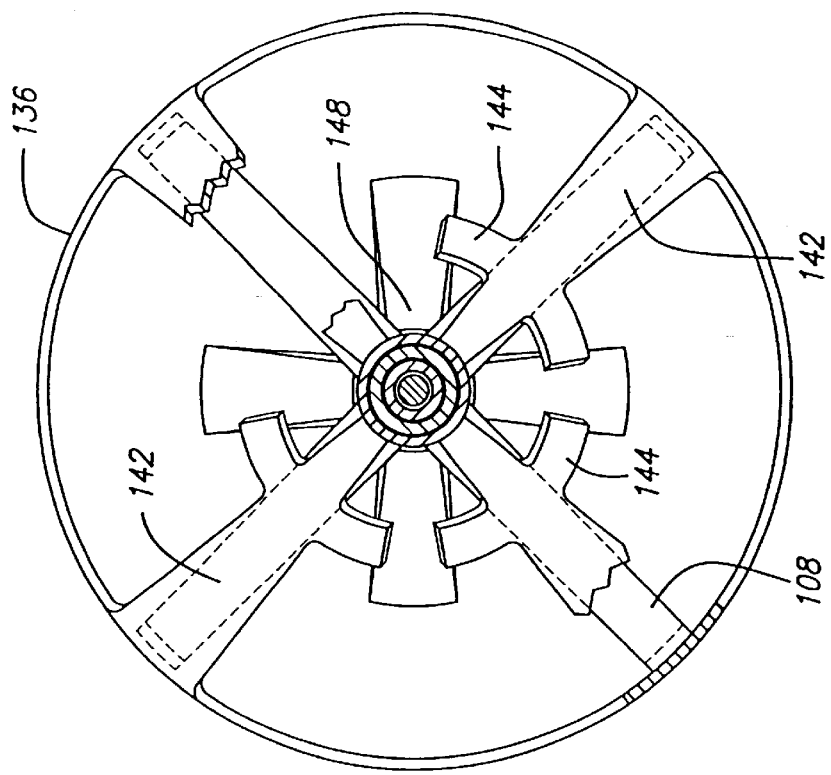
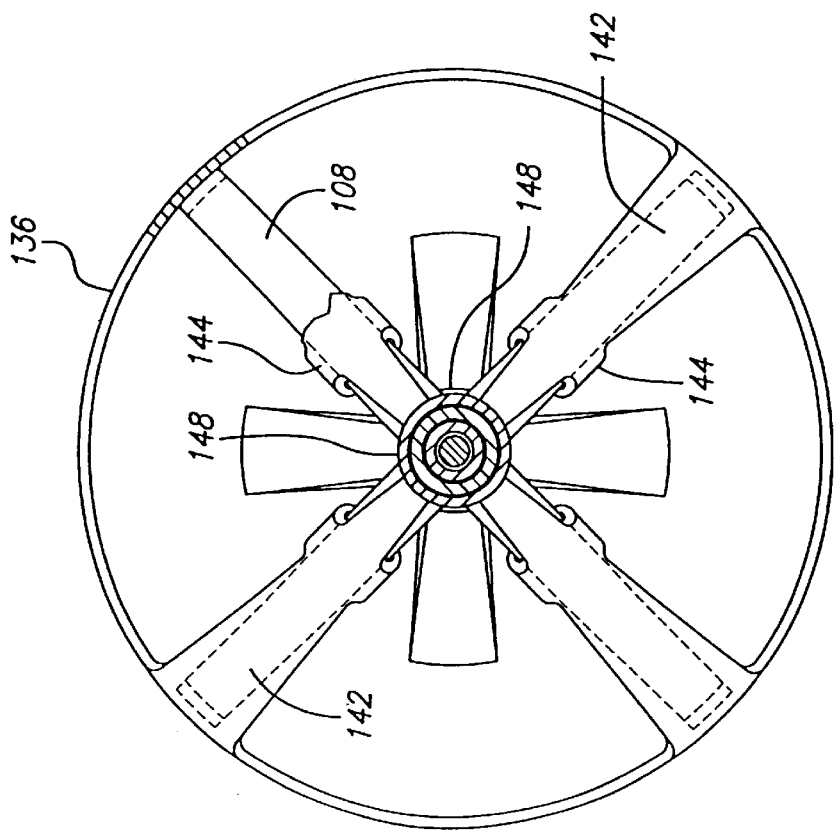

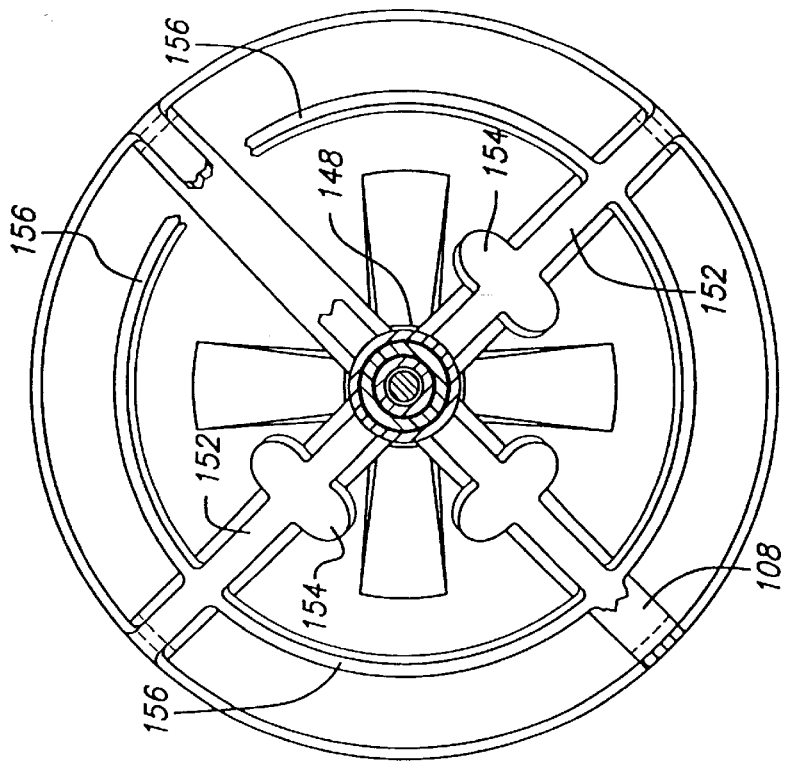
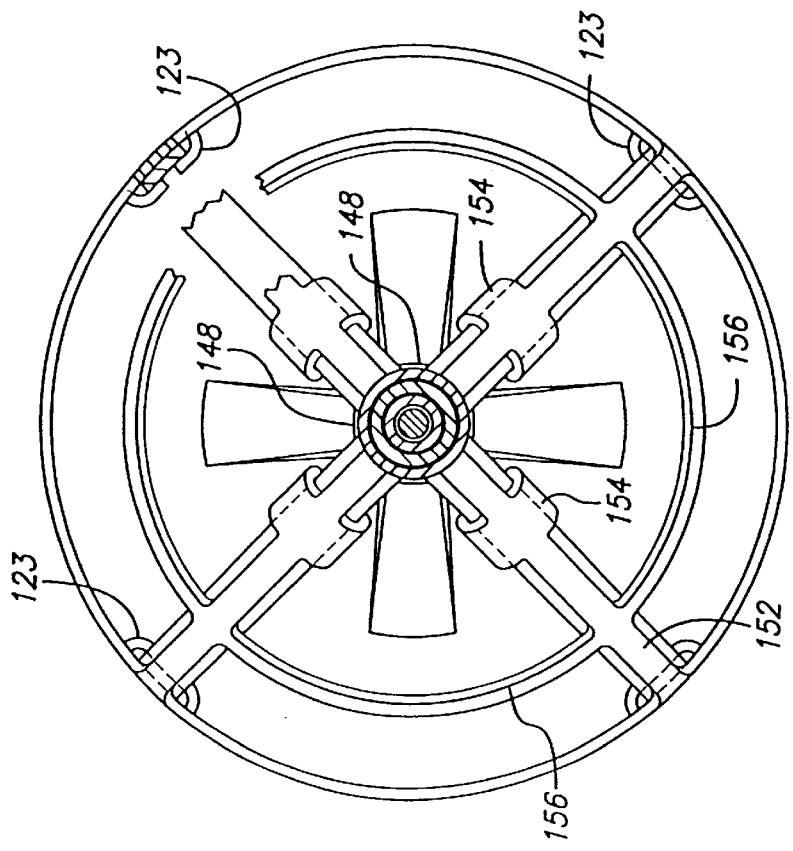

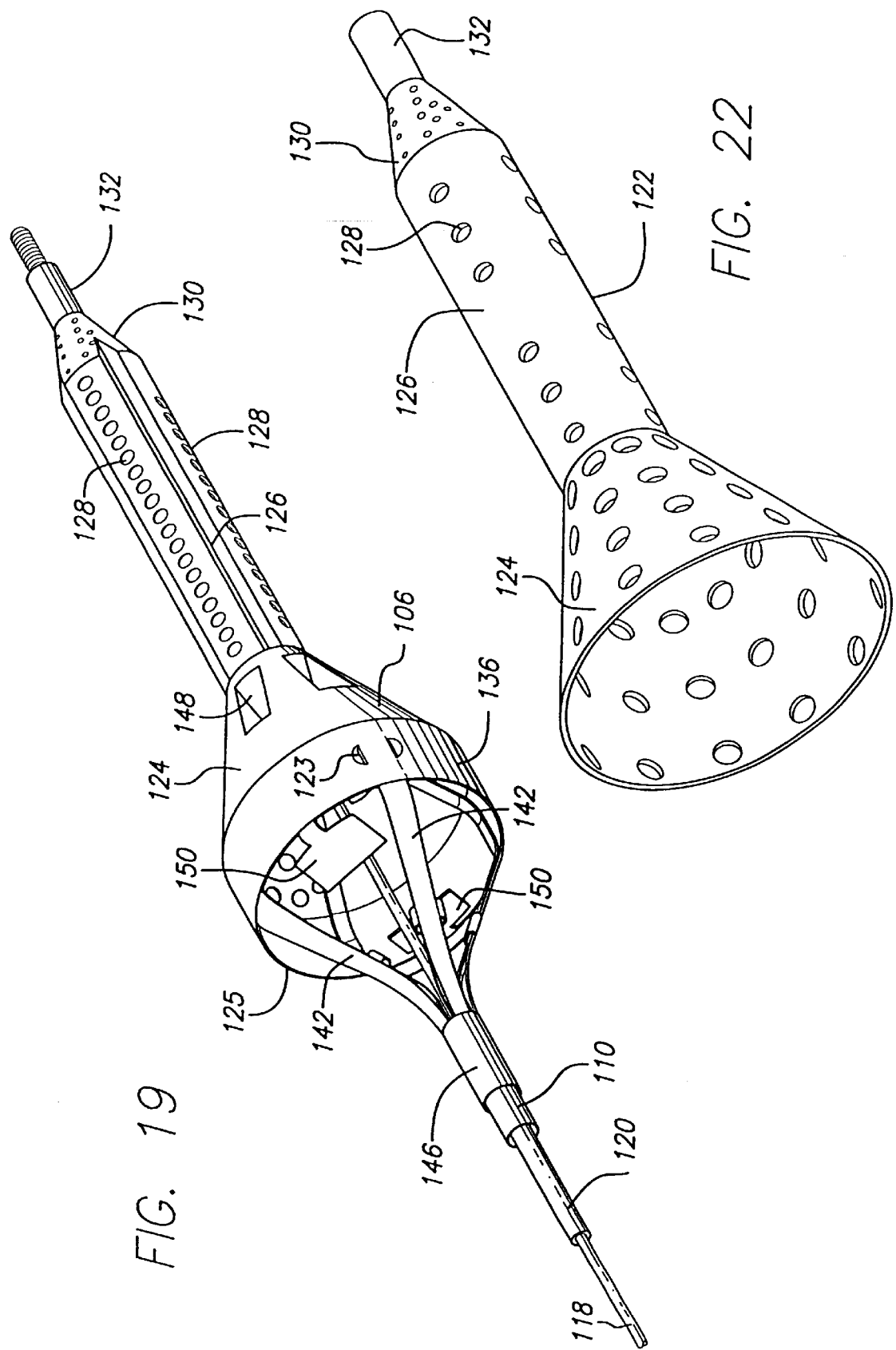

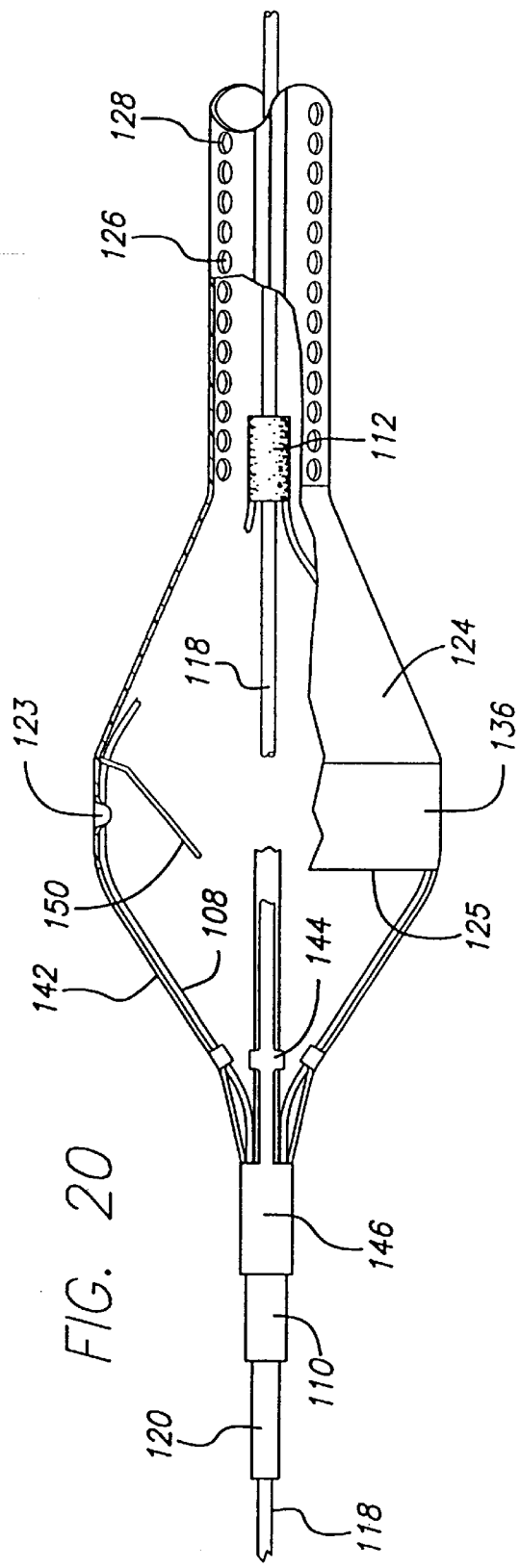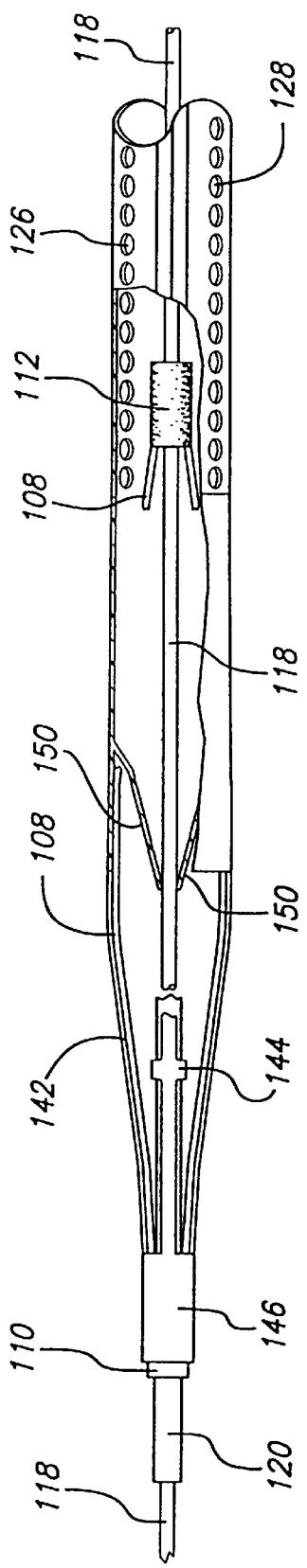

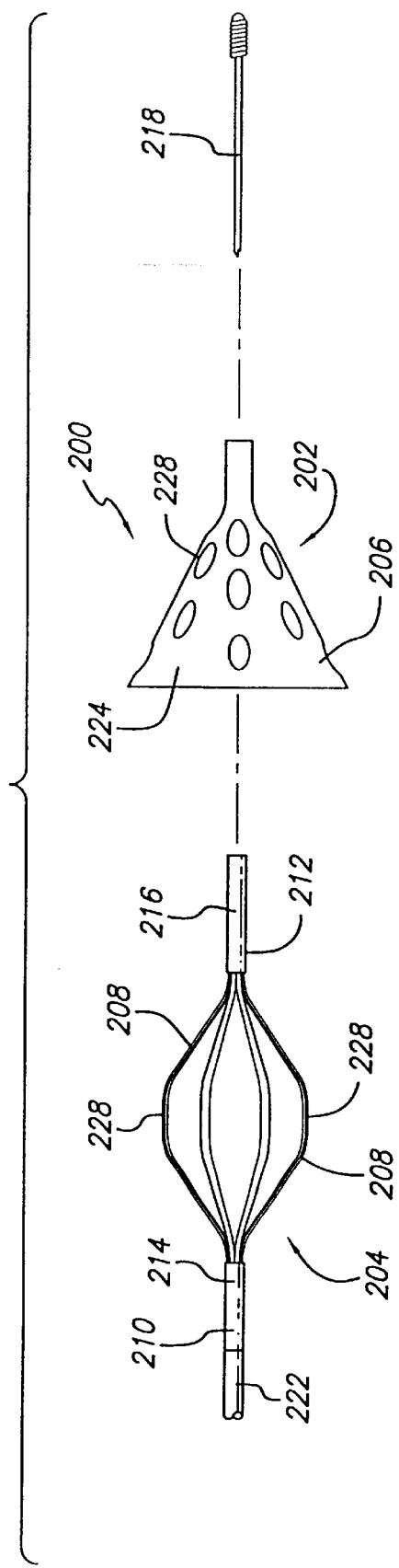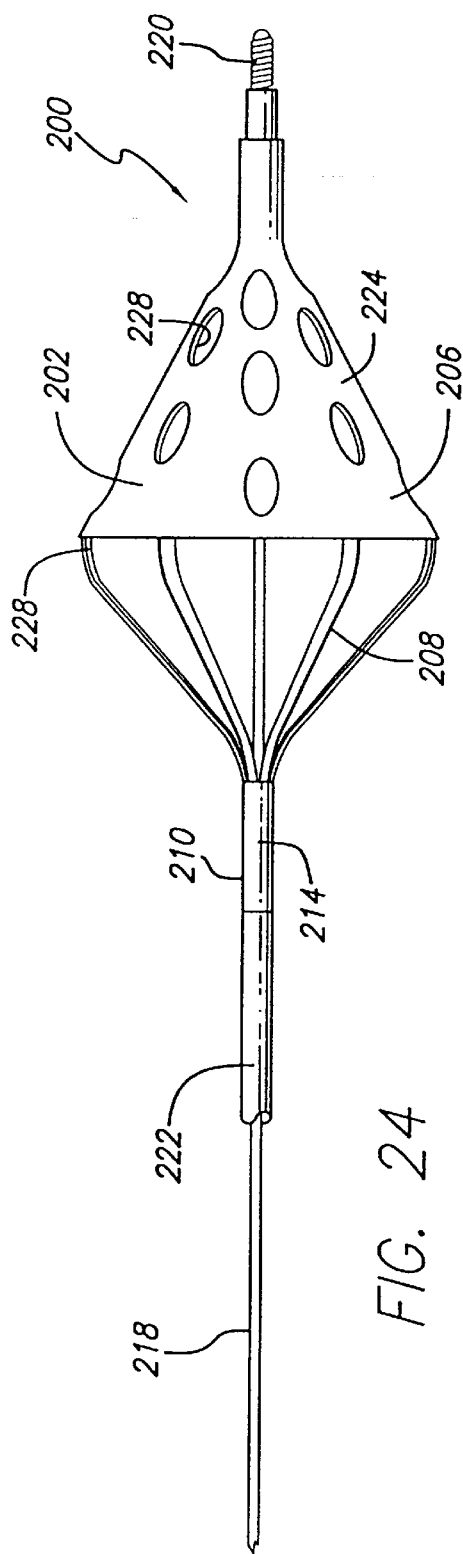
FIG. 23
FIG. 24

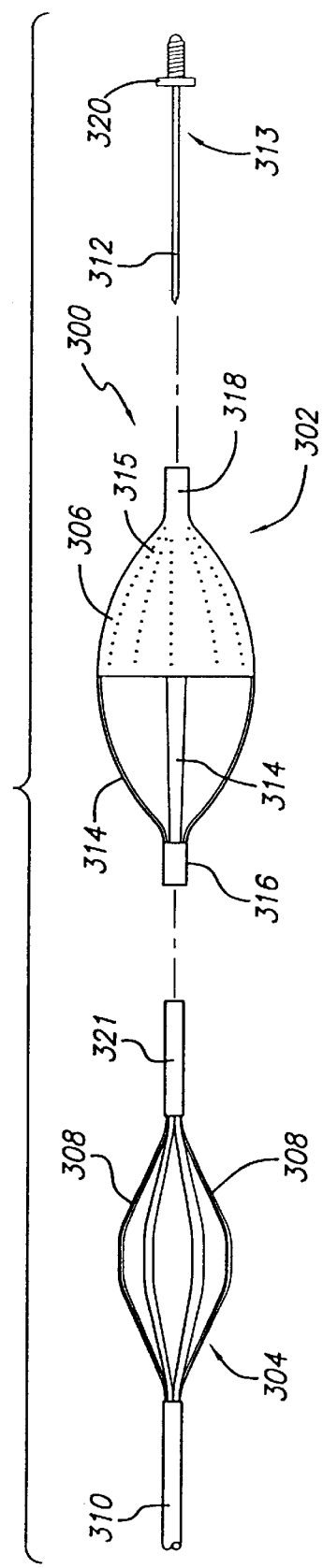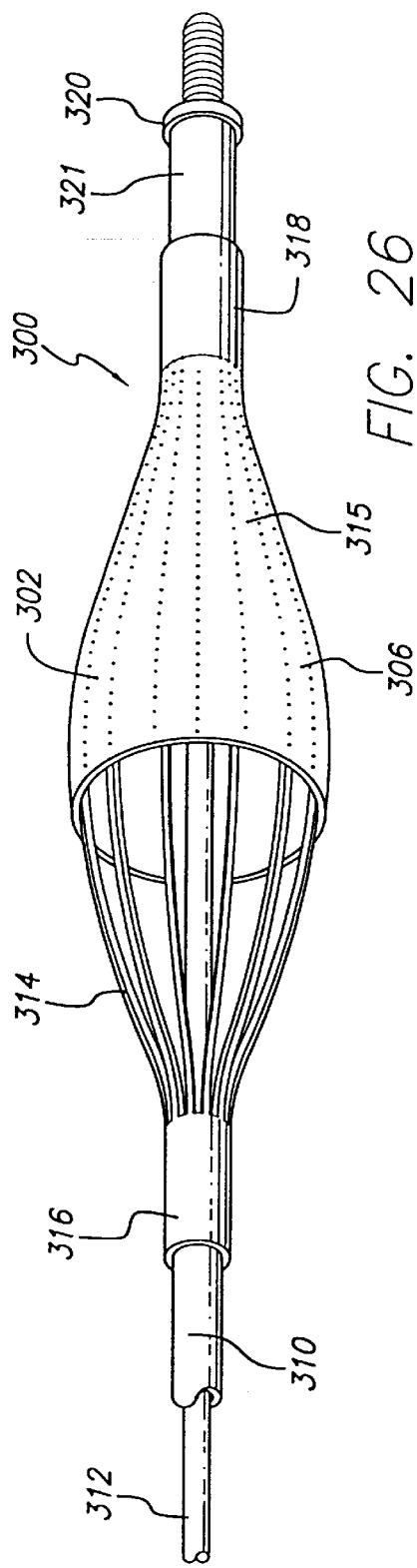
FIG. 25
FIG. 26

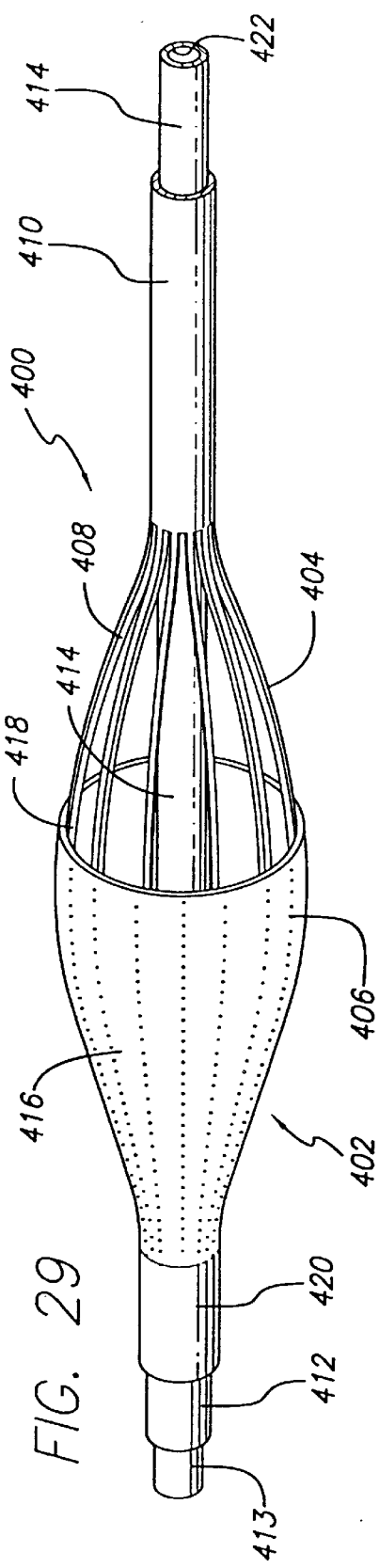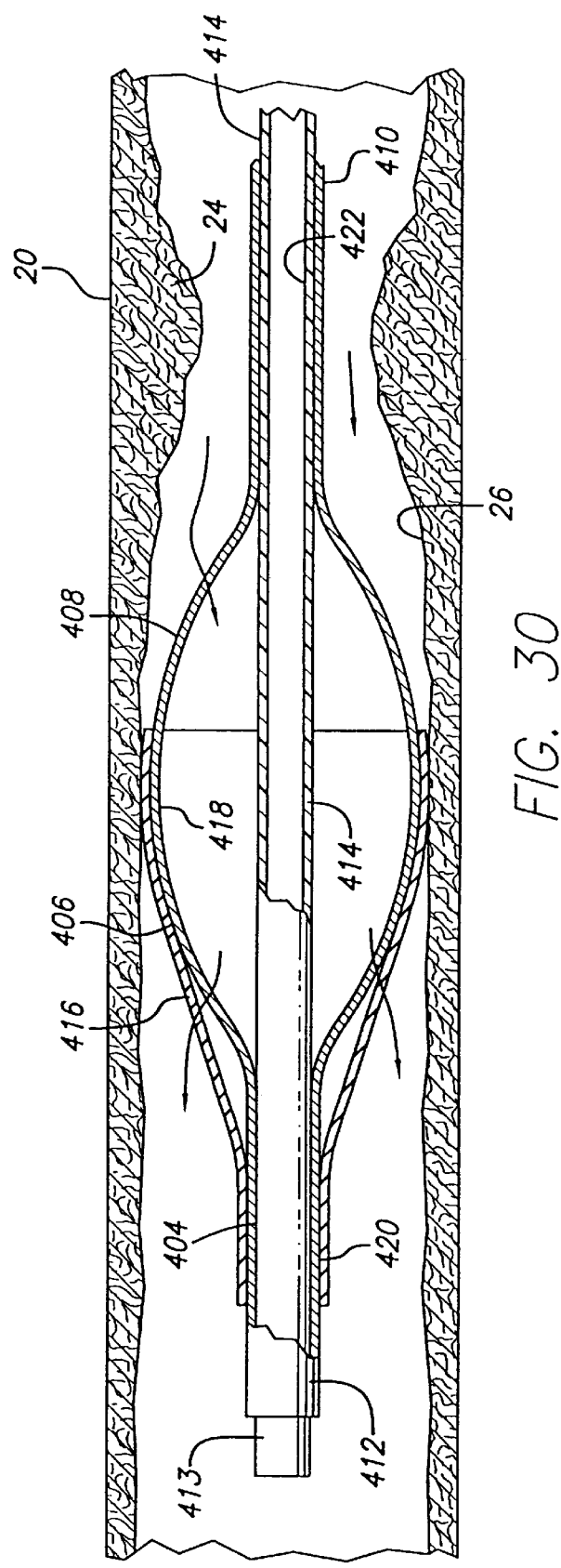

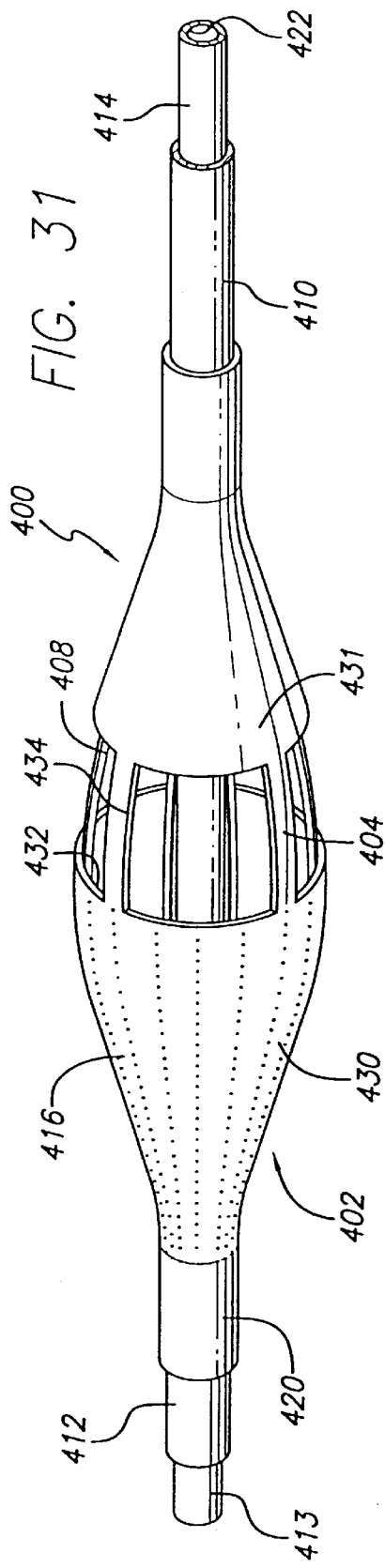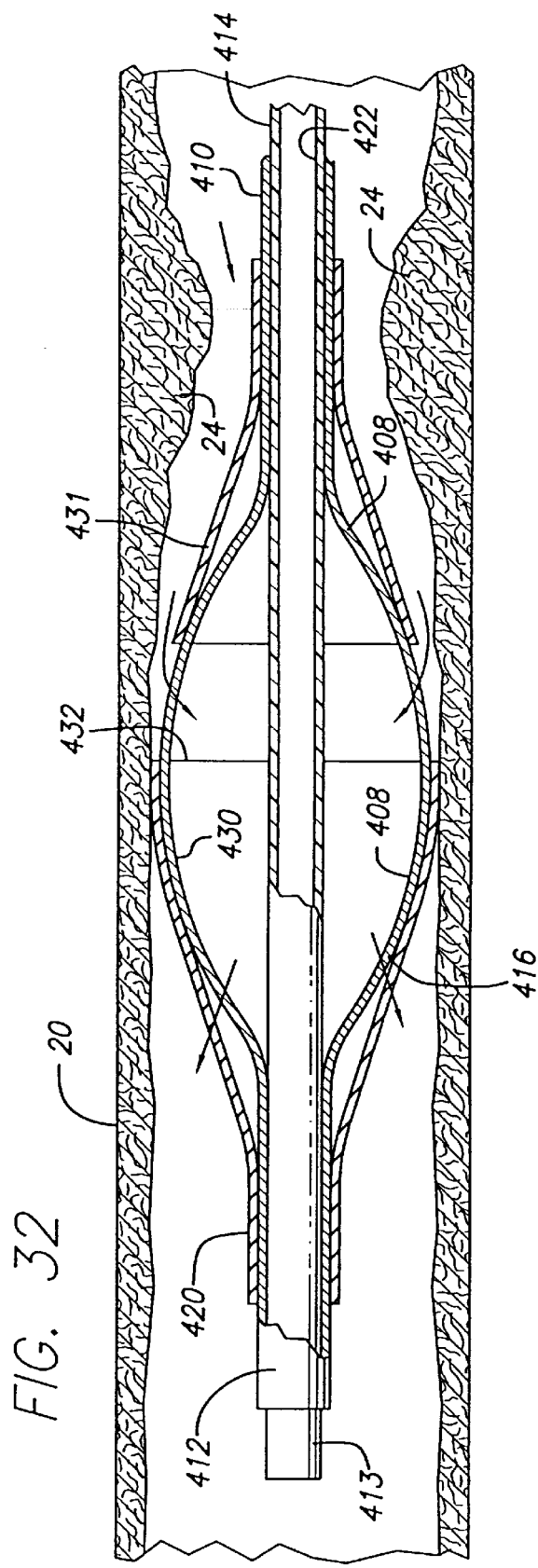

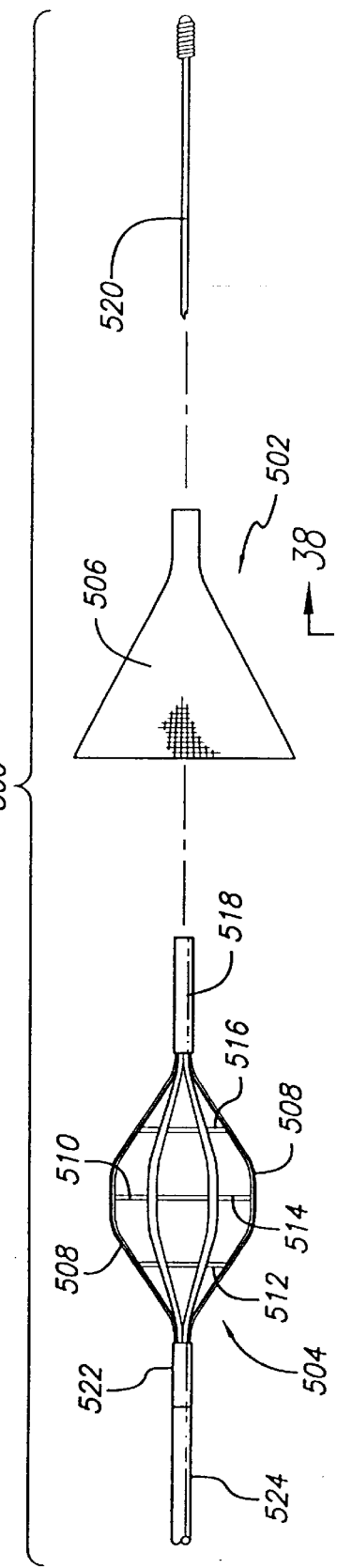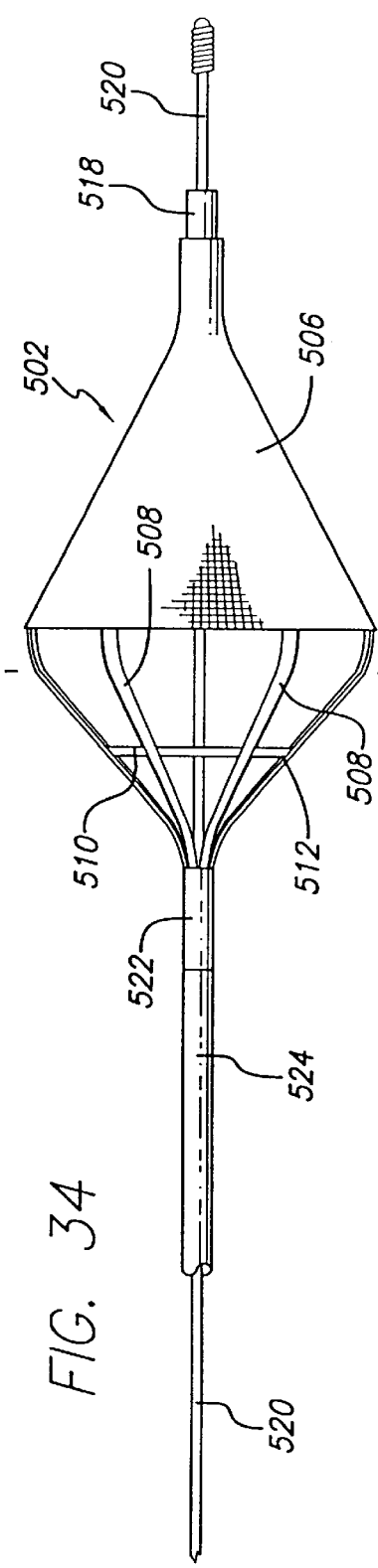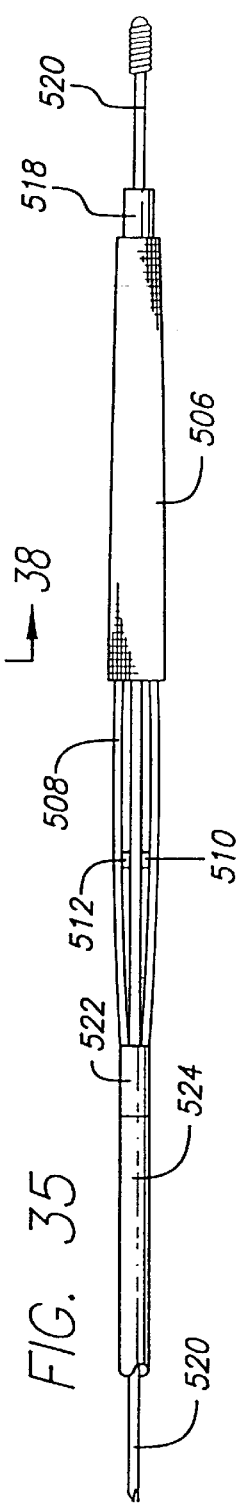
FIG. 33
FIG. 34
FIG. 35

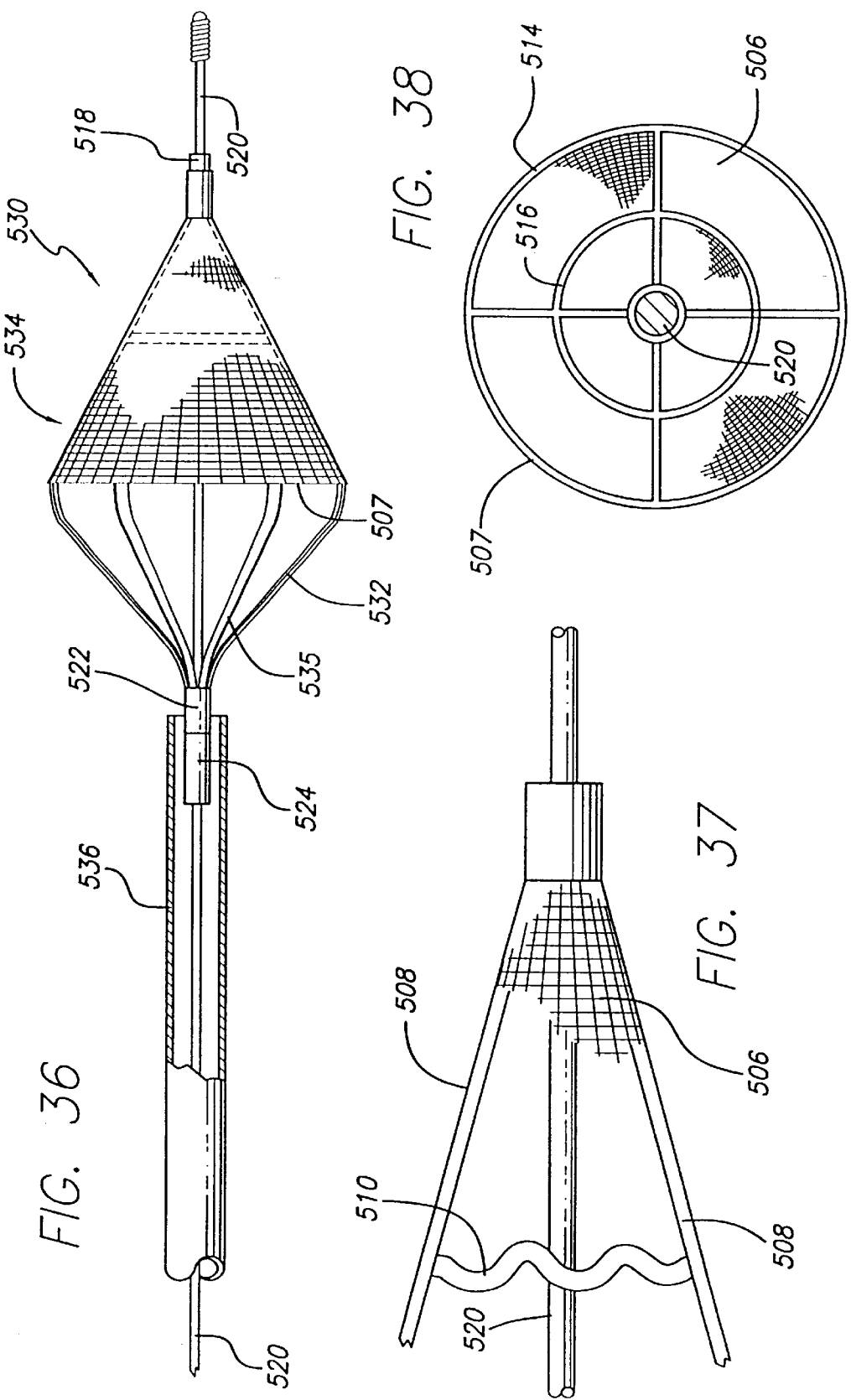

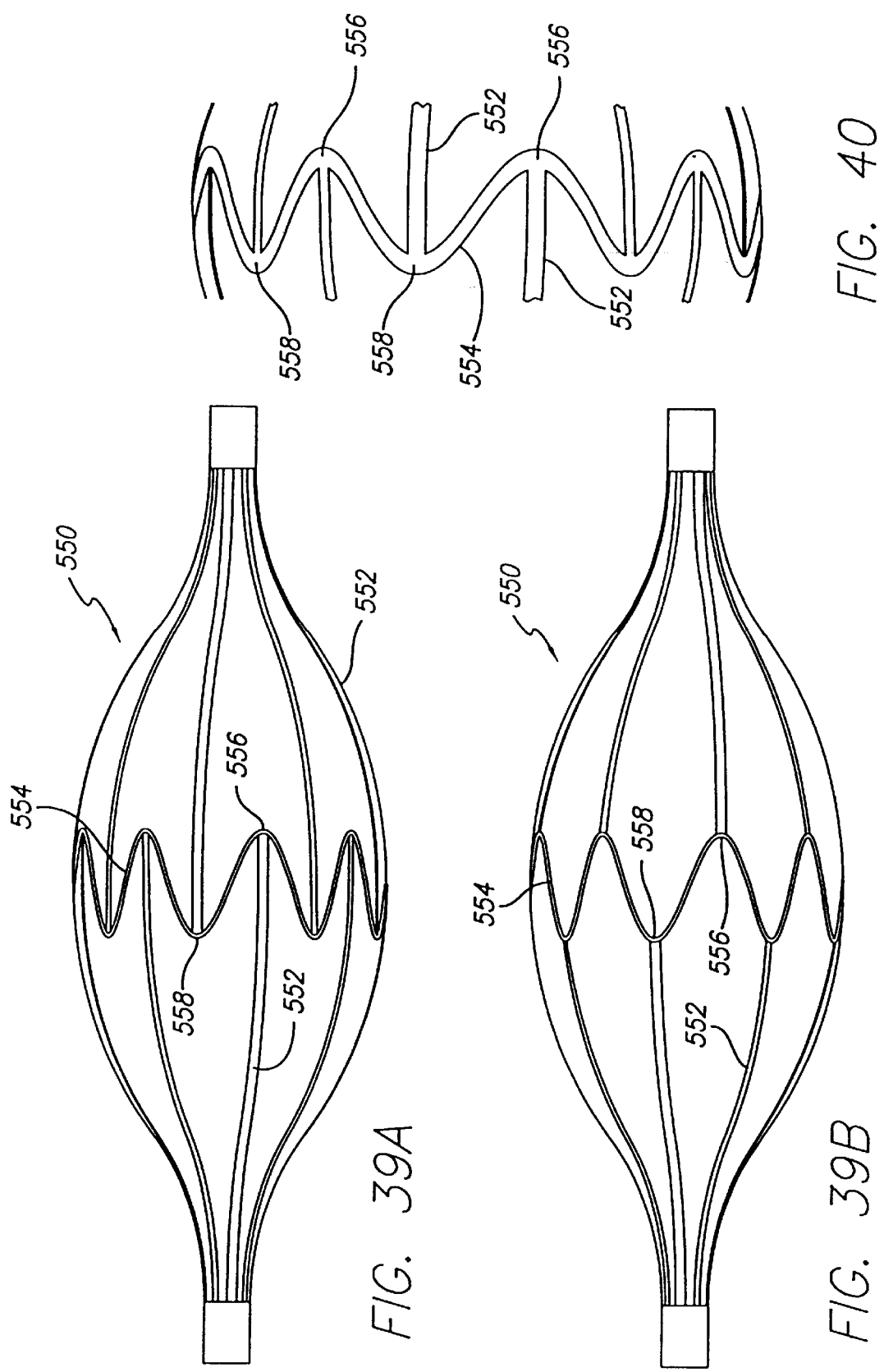

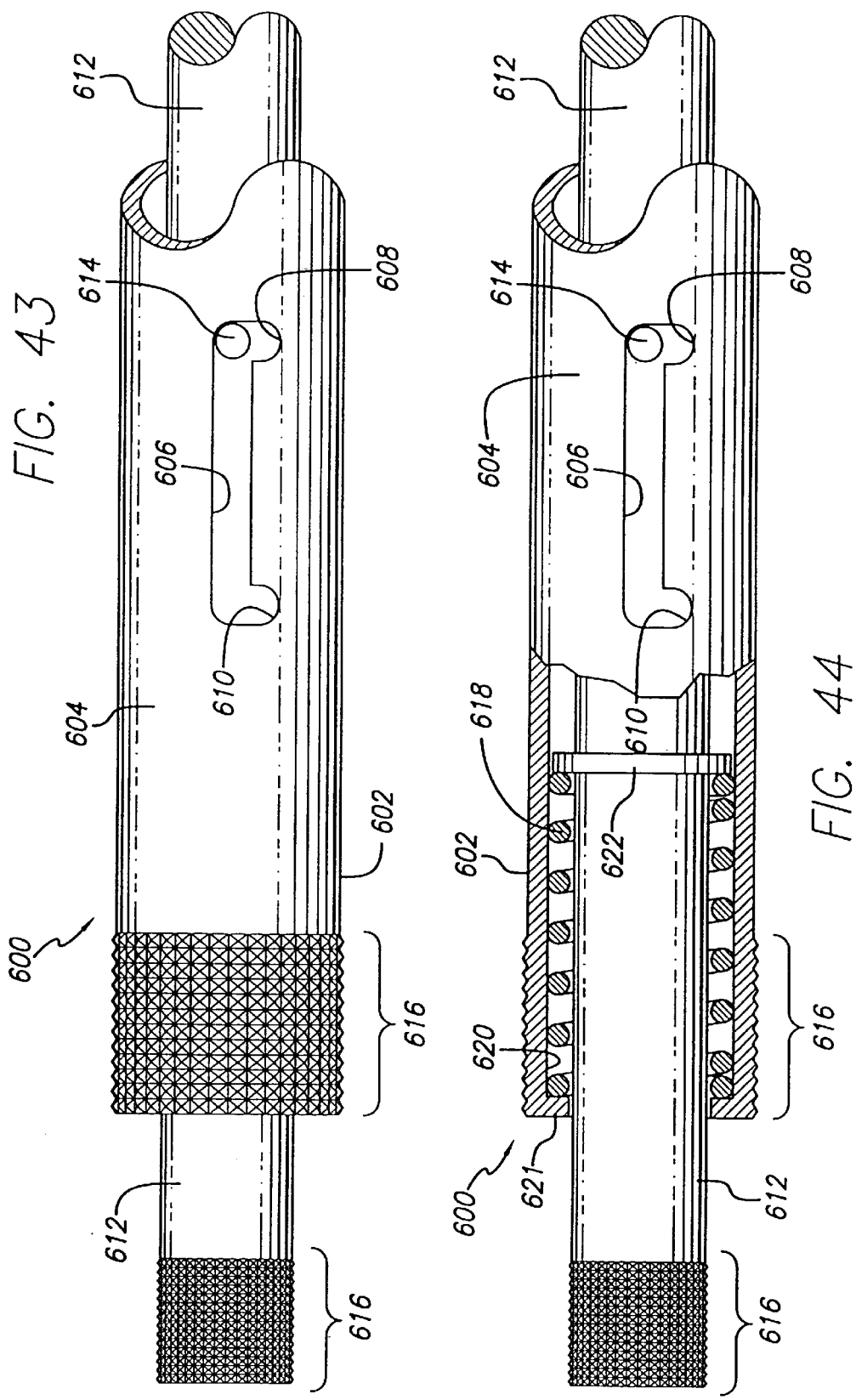

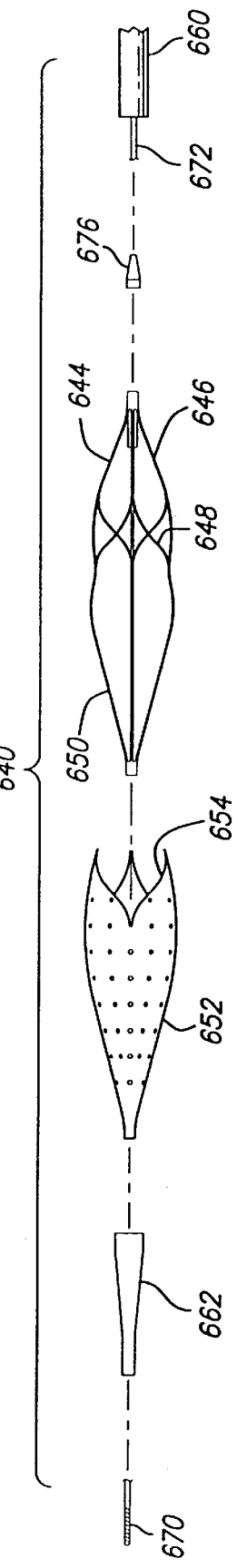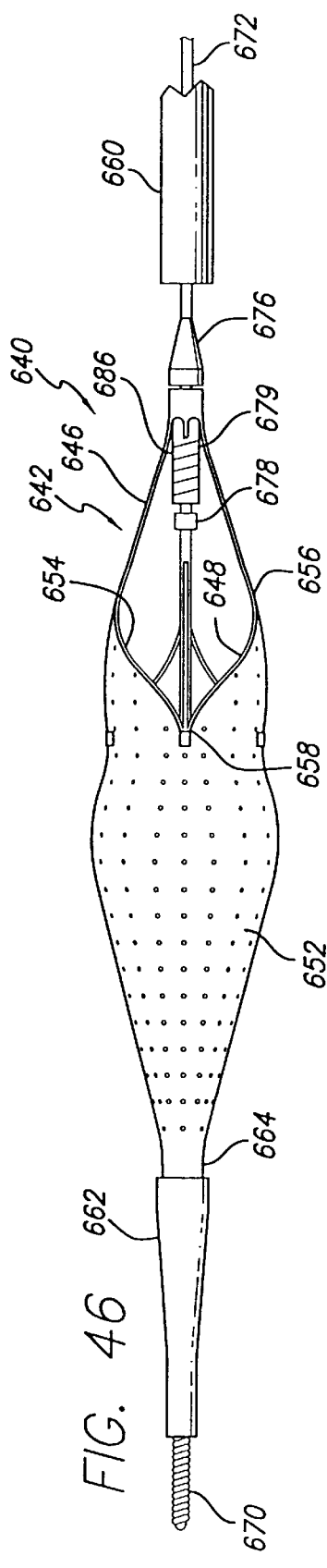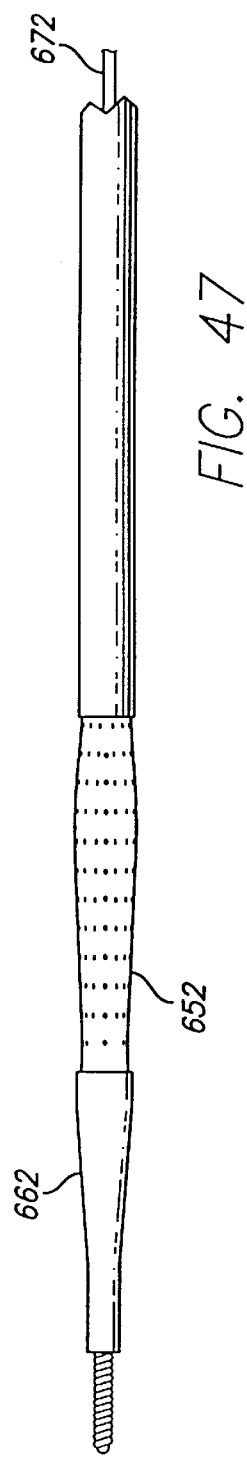
FIG. 45
FIG. 46
FIG. 47

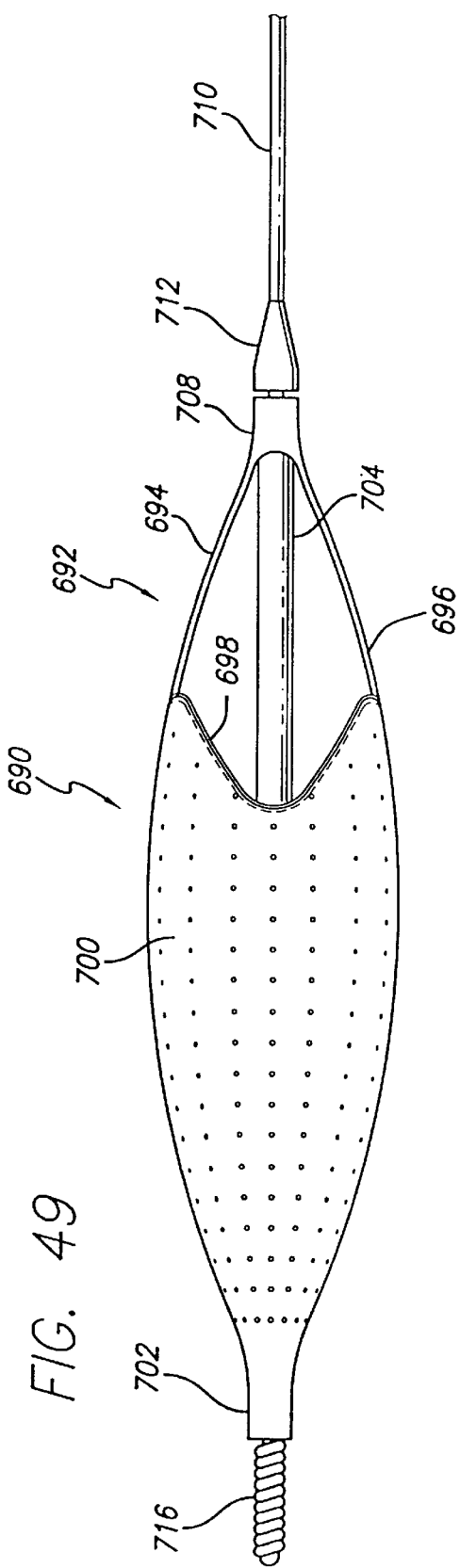

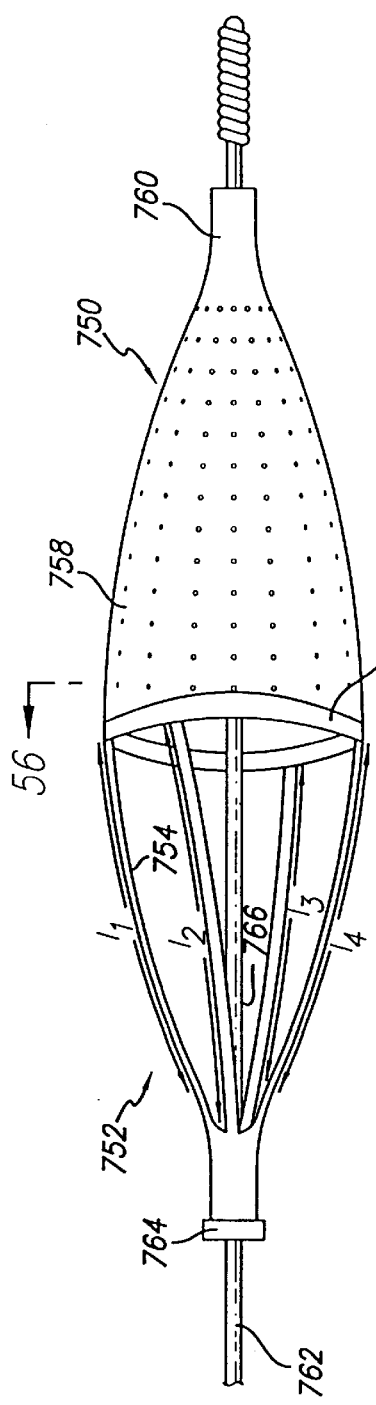
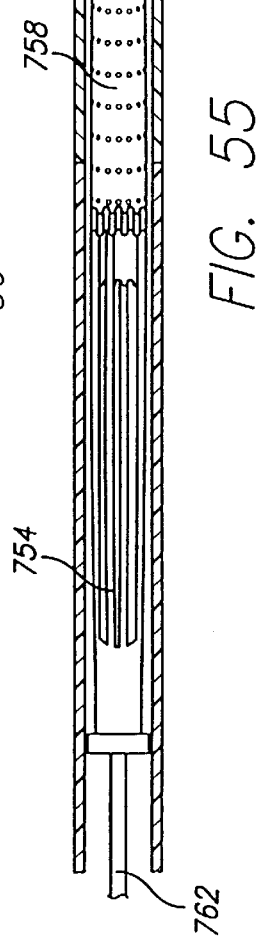
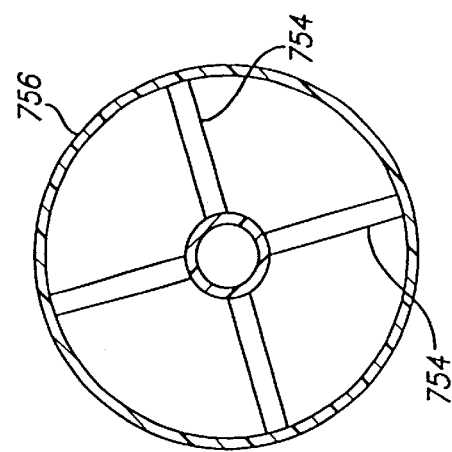
FIG. 54
FIG. 55
FIG. 56

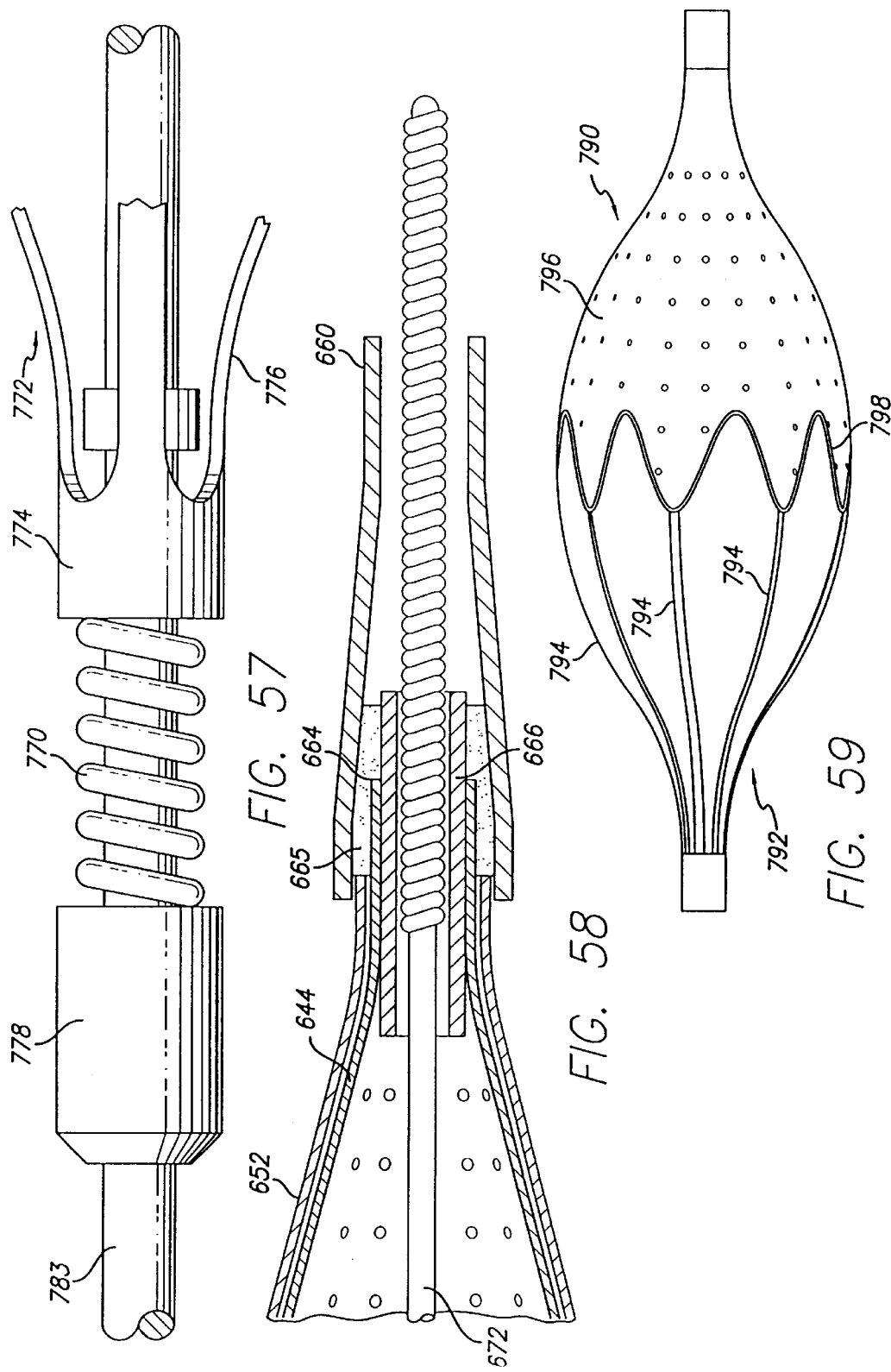

EMBOLIC PROTECTION DEVICES

This application is a continuation-in-part of application Ser. No. 9/490,319 filed Jan. 24, 2000, which is a continuation-in-part of application Ser. No. 09/476,159 filed Dec. 30, 1999, which are assigned to the same Assignee as the present application.

The present invention relates generally to filtering devices and systems which can be used when an interventional procedure is being performed in a stenosed or occluded region of a blood vessel to capture embolic material that may be created and released into the bloodstream during the procedure. The embolic filtering devices and systems of the present invention are particularly useful when performing balloon angioplasty, stenting procedures, laser angioplasty or atherectomy in critical vessels, particularly in vessels such as the carotid arteries, where the release of embolic debris into the bloodstream can occlude the flow of oxygenated blood to the brain or other vital organs, which can cause devastating consequences to the patient. While the embolic protection devices and systems of the present invention are particularly useful in carotid procedures, the inventions can be used in conjunction with any vascular interventional procedure in which there is an embolic risk.

A variety of non-surgical interventional procedures have been developed over the years for opening stenosed or occluded blood vessels in a patient caused by the build up of plaque or other substances on the wall of the blood vessel. Such procedures usually involve the percutaneous introduction of the interventional device into the lumen of the artery, usually through a catheter. In typical carotid PTA procedures, a guiding catheter or sheath is percutaneously introduced into the cardiovascular system of a patient through the femoral artery and advanced through the vasculature until the distal end of the guiding catheter is in the common carotid artery. A guide wire and a dilatation catheter having a balloon on the distal end are introduced through the guiding catheter with the guide wire sliding within the dilatation catheter. The guide wire is first advanced out of the guiding catheter into the patient's carotid vasculature and is directed across the arterial lesion. The dilatation catheter is subsequently advanced over the previously advanced guide wire until the dilatation balloon is properly positioned across the arterial lesion. Once in position across the lesion, the expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed blood vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent is crimped tightly onto the balloon portion of the catheter and transported in its delivery diameter through the patient's vasculature. At the deployment site, the stent is expanded to a larger diameter, often by inflating the balloon portion of the catheter.

Prior art stents typically fall into two general categories of construction. The first type of stent is expandable upon application of a controlled force, as described above, through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanium (NiTi) alloys, which will automatically expand from a collapsed state when the stent is advanced out of the distal end of the delivery catheter into the body lumen. Such stents manufactured from expandable heat sensitive materials allow for phase transformations of the material to occur, resulting in the expansion and contraction of the stent.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, quite often particles are not fully vaporized and thus enter the bloodstream. Likewise, not all of the emboli created during an atherectomy procedure may be drawn into the vacuum catheter and, as a result, enter the bloodstream as well.

When any of the above-described procedures are performed in the carotid or arteries, the release of emboli into the circulatory system can be extremely dangerous and sometimes fatal to the patient. Debris that is carried by the bloodstream to distal vessels of the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature. Other techniques which have had some limited success include the placement of a filter or trap downstream from the treatment site to capture embolic debris before it reaches the smaller blood vessels downstream. However, there have been problems associated with filtering systems, particularly during the expansion and collapsing of the filter within the body vessel. If the filtering device does not have a suitable mechanism for closing the filter, there is a possibility that trapped embolic debris can backflow through the inlet opening of the filter and enter the blood-stream as the filtering system is being collapsed and removed from the patient. In such a case, the act of collapsing the filter device may actually squeeze trapped embolic material through the opening of the filter and into the bloodstream.

Many of the prior art filters which can be expanded within a blood vessel are attached to the distal end of a guide wire or guide wire-like tubing which allows the filtering device to be placed in the patient's vasculature when the guide wire is manipulated in place. Once the guide wire is in proper position in the vasculature, the embolic filter can be deployed within the vessel to capture embolic debris. The guide wire can then be used by the physician to deliver interventional devices, such as a balloon angioplasty dilatation catheter or a stent, into the area of treatment. When a combination of embolic filter and guide wire is utilized, the proximal end of a guide wire can be rotated by the physician, usually unintentionally, when the interventional device is being delivered over the guide wire in an over-the-wire fashion. If the embolic filter is rigidly affixed to the distal end of the guide wire, and the proximal end of the guide wire is twisted or rotated, that rotation will be translated along the length of the guide wire to the embolic filter, which can cause the filter to rotate or move within the vessel and possibly cause trauma to the vessel wall. Additionally, it is possible for the physician to accidentally collapse or displace the deployed filter should the guide wire twist when the interventional device is being delivered over the guide wire. Moreover, a shockwave (vibratory motion) caused by the exchange of the delivery catheter or interventional devices along the guide wire can ajar the deployed filtering device and can possibly result in trauma to the blood vessel. These types of occurrences during the interventional procedure are undesirable since they can cause trauma to the vessel which is detrimental to the patient's health and/or cause the deployed filter to be displaced within the vessel which may result in some embolic debris flowing past the filter into the downstream vessels.

What has been needed is a reliable filtering device and system for use when treating stenosis in blood vessels which helps prevent the risk associated when embolic debris that can cause blockage in vessels at downstream locations is released into the bloodstream. The device should be capable of filtering any embolic debris which may be released into the bloodstream during the treatment and safely contain the debris until the filtering device is to be collapsed and removed from the patient's vasculature. The device should be relatively easy for a physician to use and should provide a failsafe filtering device which captures and removes any embolic debris from the bloodstream. Moreover, such a device should be relatively easy to deploy and remove from the patient's vasculature. The inventions disclosed herein satisfy these and other needs.

SUMMARY OF THE INVENTION

The present invention provides a number of filtering devices and systems for capturing embolic debris in a blood vessel created during the performance of a therapeutic interventional procedure, such as a balloon angioplasty or stenting procedure, in order to prevent the embolic debris from blocking blood vessels downstream from the interventional site. The devices and systems of the present invention are particularly useful while performing an interventional procedure in critical arteries, such as the carotid arteries, in which vital downstream blood vessels can easily become blocked with embolic debris, including the main blood vessels leading to the brain. When used in carotid procedures, the present invention minimizes the potential for a stroke occurring during the procedure. As a result, the present invention provides the physician with a higher degree of confidence that embolic debris is being properly collected and removed from the patient's vasculature during the interventional procedure.

An embolic protection device and system made in accordance with the present invention includes an expandable filtering assembly which is affixed to the distal end of a tubular shaft member, such as a guide wire. The filtering assembly includes an expandable strut assembly made from a self-expanding material, such as nickel-titanium (NiTi) alloy or spring steel, and includes a number of outwardly extending struts which are capable of self-expanding from a contracted or collapsed position to an expanded or deployed position within the patient's vasculature. A filter element made from an embolic capturing media is attached to the expandable strut assembly and moves from the collapsed position to the expanded position via the movement of the expandable struts. This expandable strut assembly is affixed to the guide wire in such a manner that the entire filtering assembly rotates or "spins" freely on the guide wire to prevent the filtering assembly from being rotated after being deployed within the patient's vasculature. In this manner, any accidental or intentional rotation of the proximal end of the guide wire is not translated to the deployed filtering assembly, which will remain stationary within the patient's vasculature and, as such, the threat of trauma to the vessel wall and displacement of the filter caused by the rotation and/or manipulation of the guide wire can be virtually eliminated.

The expandable struts of the strut assembly can be biased to remain in their expanded position until an external force placed on the struts to collapse and maintain the struts in their contracted or collapsed position is removed. This is done through the use of a restraining sheath which is placed over the filtering assembly in a coaxial fashion to maintain the strut assembly in its collapsed position. The composite guide wire and filtering assembly, with the restraining sheath placed over the filtering assembly, can then be placed into the patient's vasculature. Once the physician properly manipulates the guide wire into the target area, the restraining sheath can be retracted off of the expandable strut assembly to deploy the struts into their expanded position. This can be easily performed by the physician by simply retracting the proximal end of the restraining sheath (which is located outside of the patient) along the guide wire. Once the restraining sheath is retracted, the self-expanding properties of the strut assembly cause the struts to move radially outward away from the guide wire to contact the wall of the blood vessel. Again, as the struts expand radially, so does the filter element which will now be in place to collect any embolic debris that may be released into the bloodstream as the physician performs the interventional procedure. The filter sub-assembly could be bonded to the core wire at both distal and proximal ends of the embolic protection device. The core wire could be made from stainless steel or shaped memory biocompatible materials. The guide wire with the embolic protection device could be loaded into a delivery sheath. The delivery sheath could be torqued, steering the device into the intended vessel site.

The filtering assembly can be rotatably affixed to the guide wire by rotatably attaching the proximal end of the filtering assembly to the guide wire. The distal end of the strut assembly can move longitudinally along the guide wire and is also rotatable on the guide wire as well. This allows the strut assembly to move between its collapsed and expanded positions while still allowing the entire filtering assembly to freely rotate or "spin" about the guide wire. This attachment of the proximal end of the strut assembly to the guide wire allows the restraining sheath to be retracted from the filtering assembly and permits a recovery sheath to be placed over the expanded strut assembly to move the strut assembly back to the collapsed position when the embolic protection device is to be removed from the patient's vasculature.

The filtering assembly also may include a dampening element or member which is utilized to absorb some of the shockwave (vibratory motion) that may be transmitted along the length of the guide wire during the handling of the guide wire by the physician. Since a sudden shock to the filtering assembly can cause the filter to scrape the wall of the blood vessel or become displaced in the vessel, the dampening member acts much like a "shock absorber" to absorb some of the shock and prevent the transmission of the shock force to the filtering assembly. This shock can be produced via a number of way, for example, through the exchange of interventional devices along the guide wire. Also, when the restraining sheath is removed from the filtering assembly, a shockwave can be created if the self-expanding struts open too quickly. As a result of utilizing the dampening member, shock and trauma to the patient's vasculature are minimized and the chances of displacing the filter are virtually eliminated. In one aspect of the dampening member, a helical spring is formed on the proximal end of the expandable strut assembly to provide dampening to the assembly. Other methods of obtaining dampening can be utilized, such as attaching a separately formed spring or elastomeric member to the strut assembly.

The expandable strut assembly made in accordance with the present invention may be made from a length of tubing (also known as a "hypotube") made from a shape memory alloy or other self-deploying material. Stainless steel or other biocompatible metals or polymers can be utilized to form the struts of the assembly. Another material is nickel-titanium (NiTi). The individual struts of the expandable strut assembly are formed on the length of hypotube by selectively removing material from the tubing to form the particular size and shape of the strut. For example, the wall of the hypotube can be laser cut with slots to form the individual struts. Small tabs can also be lazed into the tubing along the strut which can be used to hold the filter member in place. By selectively removing portions of the hypotube by a high precision laser, similar to lasers utilized in the manufacturer of stents, one can achieve a very precise and well defined strut shape and length. In one aspect of the present invention, the pattern of the material to be removed from the hypotubing can be a repeating diamond-shaped which creates a strut pattern in the form of two inverted triangles meshed together. This particular strut pattern provides greater strength along the strut where it would have a tendency to break or become weakened. Such a strut pattern also provides for a more natural bending position for each strut, allowing the expandable strut assembly to open and close more uniformly. In one particular pattern, the strut pattern requires the removal of a repeating truncated diamond pattern by laser or other means to create the shape of the strut. In this particular pattern, each strut has a relatively straight center section formed between two inverted triangles, somewhat similar to the strut pattern described above. This particular strut pattern provides an expanded center section which allows the struts to expand to a greater volume, which helps in the capture of emboli by allowing a larger filter to be placed on the strut assembly. The center section located between the two inverted triangle also provides a sufficient working area to attach the filter element onto the strut assembly. These same features can be accomplished by curved sections which have a reduced width in the center section.

The embolic protection device may also include a filtering assembly with a strut assembly which is not self-expanding, but utilizes the application of a force on the proximal and distal ends of the strut assembly to deploy and collapsed the assembly. In this particular form of the invention, the embolic protection device includes an inner shaft member and an outer tubular member which is coaxially disposed over the inner shaft member. The distal end of the expandable strut assembly can be attached to the inner shaft member with the proximal end of the strut assembly being attached to the distal end of the outer tubular member. When there is relative movement between the inner shaft member and outer tubular member, a force is created which is imparted to the expandable strut assembly to cause the struts to either contract or expand. For example, when the outer tubular member and inner shaft member are moved relative to each other to produce an inward force acting on the proximal and distal ends of the strut assembly, the force causes the expandable struts to move from the collapsed position into the expanded position. Thereafter, when the strut assembly is to be collapsed, the outer tubular member and inner shaft member can be moved relative to each other to create an outward force acting on the proximal and distal end of the strut assembly to cause the expanded struts to move back to their collapsed position. A physician easily can manipulate the proximal ends of the inner shaft member and outer tubular member to deploy and collapse the filtering assembly as needed. The filtering assembly could be self-expanding with the movement of the inner and outer members providing the means for expanding and collapsing the assembly without the need for an outer sheath.

The inner shaft member can be a guide wire which can be utilized to move the filtering assembly directly into position downstream from the lesion for capturing any embolic debris which may be released into the bloodstream. The inner shaft member could also be a elongated tubular member which has an inner lumen that can track along a guide wire once the guide wire has been maneuvered into position into the patient's vasculature. The entire embolic protection device can then be delivered to the desired location over the guide wire using over-the-wire techniques.

The filtering element utilized in conjunction with the embolic protection device can take on many different forms as are disclosed herein. In one aspect, the filter includes a proximal cone section which expands to the diameter of the artery in which the embolic protection device is to be deployed. This proximal cone section funnels blood flow and embolic debris into a main or central filter located distal to the proximal cone section. This proximal cone may or may not provide filtering itself. Its primary function is flow direction and its ability to collapse and expand with the expandable struts of the strut assembly. A main or central filter may comprise an elongated tubular shaped member is located distal to the proximal cone section. It is integral with the distal end of the proximal cone section and provides a large filtering area that acts as a storage reservoir for holding embolic material. Ideally, it is sized so that it receives any and all of the embolic material which it is to be filtered by the embolic protection device. It includes a number of perfusion openings which allow blood to pass through but retain embolic material. The central filter may not be collapsible or expandable, but rather may be made somewhat rigid and has an outer diameter large enough to provide a storage reservoir for holding embolic material yet can be withdrawn and delivered through the particular guiding catheter utilized to deploy the embolic protection device into the patient's vasculature. The central filter also could be made from collapsible material, but should have an outer diameter which is large enough to provide an adequate storage reservoir yet can be withdrawn through the guiding catheter as well. Although this central filter may have a substantially fixed diameter, it can also be tapered and should have an outer diameter small enough to fit through the inner diameter of the specific guiding catheter utilized to deploy the device.

As with all of the filter elements made in accordance with the present invention, the material which can be utilized includes a variety of materials such as polymeric material which is foldable and recovers elastically to aid in the capture of the emboli trapped in the filter. Other suitable materials include braided or woven bio-compatible material which can significantly filter the desired size of the embolic debris to be captured by the filter. The filter can be formed by blowing a suitable material into the proposed shape and then cutting off unwanted portions. The perfusion openings can be drilled into the material using a laser, such as an excimer laser, or by mechanically drilling and punching the openings to the desired size and shape. Laser drilling of the holes provides accuracy, quickness and the ability to drill complex hole shapes, circles, ovals and slots. Alternatively, the central filter can be made from the same or different material from the proximal cone portion and can be welded or bonded to create an integral unit.

Still another type of filter material can be utilized in accordance with the present invention which does not require the use of mechanical drilling or laser cutting to create the precise openings in the filter which allows adequate blood perfusion while capturing the desired size of embolic debris. This filtering material utilizes an open-celled microporous structure which has uniform porosity and a network-like structure which traps embolic particles. Such filtering material has the benefit of being both mechanically strong and more tear resistant while being most effective in trapping embolic debris since the particles must travel through an intricate network of patterns in order to escape through the filter. Due to the open-celled microporous structure, the probability that embolic debris will somehow escape through the structure is extremely minimal.

The method for making this open-celled microporous filtering material consists of dissolving a selected polymer into a solvent to produce a polymer/solvent solution. This polymer/solvent solution is then cast or sprayed as a film into the desired shape and thickness. For example, the film can be cast onto a cone-shaped rotating mandrel which improves the uniformity of the film thickness. Then, a non-solvent is cast or sprayed onto the film before complete evaporation of the solvent. This non-solvent induces a phase-separation of the polymer to create the microporous structures. The resulting microporous material can then be placed onto the strut assembly to create the composite emboli-catching device.

In one particular filter made in accordance with the present invention, the proximal cone includes advantageous features which help prevent the filter from slipping off the expandable strut assembly. These features also help to prevent trapped embolic debris from being squeezed out of the filter as the filter is being collapsed for removal from the patient's vasculature. The filter may include, for example, a set of restraining straps designed to be attached to each of the proximal ends of the struts to help secure the filter onto the strut assembly. These straps can include tabs which can be wrapped around each of the struts and permanently affixed thereto utilizing a suitable adhesive. The proximal cone section of the filter may also include a number of indented flaps which cooperate to close off the inlet opening of the central filter. These indented flaps are formed on the proximal cone and move into position to cover the opening of the central filter when the proximal cone section is collapsed by the strut assembly. Therefore, the possibility that any embolic debris trapped within the deep reservoir of the central filter will be discharged through the inlet opening is greatly diminished since the opening will be closed off by these indented flaps. Likewise, the proximal cone section of the filter can also include inwardly inverting flaps located near the inlet opening of the proximal cone section which cooperate to close off the large inlet opening of the proximal cone section whenever the strut assembly is collapsed. These elements help to prevent accidental leakage of trapped embolic debris whenever the filtering assembly is collapsed for removal from the patient.

In other aspects of the present invention, variations can be made to the devices described above which enhance their performance characteristics. For example, a strut assembly can be utilized which utilizes struts having different lengths which allows greater ease in re-sheathing the expanded strut/filter assembly since the filter and struts can be incrementally introduced into the restraining sheath, rather than having the struts and filter material enter the sheath all at once. Likewise, the filter itself can be made with a proximal edge which has a scalloped pattern which helps prevent the filter material from entering into the sheath all at once. As a result, the filtering assembly can be more easily retracted by the recovery sheath and collapsed to its smaller profile when the device is to be removed from the patient's vasculature.

Other advantages associated with the present invention include the placement of a surface coating on the strut of the strut assembly for reducing the coefficient of friction at selected areas of the strut assembly to help prevent possible embolic material from sticking to struts. Embolic debris which does not make its way into the filter and becomes "stuck" on proximal struts of the filter assembly can possibly be released into the bloodstream when the filter assembly is being collapsed and withdrawn from the patient's vasculature. In one aspect, selective deposition of a slippery polymer to the proximal struts of the strut assembly can be utilized to reduce the coefficient of friction between the embolic debris and the struts. This helps allow the embolic material to be less likely to stick on a strut assembly and more likely to pass into the filter. High areas of strain of the strut assembly may cause the coating material to crack if the coating is not sufficiently elastic. Additionally, high strain regions of the device would not be coated if the coating would affect the performance of the expansion of the strut assembly. Such materials includes polyimide and PTFE coatings, which can be applied to a strut assembly without affecting the mechanical properties of the base material. In another aspect of the invention, a coating of "slippery" polymer deposited on the entire strut assembly provided that the polymer was sufficiently elastic so as not to crack or affect the ability of the struts to bend throughout the device.

These and other advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in cross section, of an embolic protection device embodying features of the present invention showing the expandable filtering assembly in its collapsed position within a restraining sheath and disposed within a vessel.

FIG. 2 is an elevational view, partially in cross section, similar to that shown in FIG. 1, wherein the expandable filtering assembly is in its expanded position within the vessel.

FIG. 3 is a perspective view of the strut assembly which forms part of the filtering assembly of the present invention as shown in its collapsed position.

FIG. 4 is a plan view of a flattened section of the expandable strut assembly shown in FIG. 3 which illustrates one particular strut pattern for the expandable strut assembly.

FIG. 7 is an elevational view, partially in cross section, of the proximal end of the expandable strut assembly of FIG. 2 as it is rotatably attached to the guide wire.

FIG. 8 is an elevational view, partially in section and fragmented, showing the distal end of the filtering assembly of FIG. 2 as it is slidably mounted on the guide wire.

FIG. 10 is a elevational view of the various components making up the embolic protection device of FIG. 9.

FIG. 11 is an elevational view of the embolic protection device of FIG. 9 in its expanded position.

FIG. 12 is an end view of the filter element of the embolic protective device of FIG. 11 taken along lines 12—12.

FIG. 13 is an end view of the filtering element of FIG. 12 which shows the retaining tabs of the filter prior to being wrapped around the struts of the expandable strut assembly to help retain the filer element on the strut assembly.

FIG. 14 is an end view, similar to that shown in FIG. 12, of another embodiment of the filter element of the embolic protection device which shows an alternative embodiment of retaining tabs and structural elements that can be used to help retain the filter element on the strut assembly.

FIG. 15 is an end view of the filter element of FIG. 14, showing the retaining tabs of the filter element prior to being wrapped around the struts of the expandable strut assembly to help retain the filter element on the strut assembly.

FIG. 19 is a perspective view of an embolic protection device made in accordance with the present invention which includes inverted flaps which help close the inlet opening of the proximal cone section of the filter element when the device is collapsed.

FIG. 20 is an elevational view, partially in cross-section and fragmented, of the embolic protection device of FIG. 19 showing the proximal cone section and inverted flaps in an expanded position.

FIG. 21 is an elevational view, partially in cross-section and fragmented, of the embolic protection device of FIG. 19 wherein the proximal cone section is collapsed which causes the inverted flaps to close off the inlet opening of the proximal cone section of the filter element.

FIG. 22 is a perspective view of an alternative embodiment of a filter element made in accordance with the present invention.

FIG. 23 is an elevational view of the various components which make up another embodiment of an embolic protection device made in accordance with the present invention.

FIG. 24 is an elevational view depicting the embolic protection device of FIG. 23 in the expanded position.

FIG. 25 is an elevational view of the various components which make up another embodiment of an embolic protection device made in accordance with the present invention.

FIG. 26 is an elevated view depicting the embolic protection device of FIG. 25 in the expanded position.

FIG. 29 is another embodiment of an embolic protection device made in accordance with the present invention.

FIG. 30 is an elevational view, partially in section, of the embolic protection device of FIG. 29 in its expanded condition within a vessel.

FIG. 31 is another embodiment of an embolic filtering device made in accordance with the present invention.

FIG. 32 is an elevational view, partially in section, of the embolic filtering device of FIG. 31 in its expanded condition and disposed within a vessel.

FIG. 33 is an elevational view of the various components making up another embodiment of an embolic protection device made in accordance with the present invention.

FIG. 34 is an elevational view depicting the embolic protection device of FIG. 33 in its expanded position.

FIG. 35 is an elevational view depicting the embolic protection device of FIG. 34 in its collapsed position.

FIG. 36 is an elevational view, partially in section, of an alternative embodiment of an embolic protection device similar to that shown in FIG. 34.

FIG. 37 is an elevational view of two deployment members which move the struts of the strut assembly into the expanded or collapsed positions.

FIG. 38 is an end view of the filtering assembly of FIG. 34 taken along lines 38—38.

FIG. 39A is an elevational view depicting an alternative strut assembly made in accordance with the present invention which allows the assembly to be collapsed to a lower profile.

FIG. 39B is an elevational view depicting an alternative strut assembly made in accordance with the present invention which allows the assembly to be collapsed to a lower profile.

FIG. 40 is an expanded side view showing the arrangement of struts on the strut assembly of FIG. 39.

FIG. 43 is an elevational view of a proximal locking mechanism which can be utilized in accordance with embodiments of the embolic protection device made in accordance with the present invention.

FIG. 44 is an elevational view, partially in section, showing the biasing spring of the locking mechanism of FIG. 39 which can maintain the embolic protection device either in the collapsed or expanded position.

FIG. 45 is an elevational view of the various components making up another embodiment of an embolic protection device made in accordance with the present invention.

FIG. 46 is an elevational view depicting the embolic protection device of FIG. 45 in its expanded position.

FIG. 47 is an elevation view depicting the embolic protection device of FIG. 46 as it is being moved into its collapsed position.

FIG. 49 is an elevational view of another embodiment of the embolic protection device made in accordance with the present invention.

FIG. 50 is a cross-sectional view depicting the embolic protection device of FIG. 49 in its expanded position.

FIG. 54 is an elevational view of another embodiment of an embolic protection device made in accordance with the present invention.

FIG. 55 is an elevational view, partially in cross-section, similar to that shown in FIG. 54, wherein the expandable filtering assembly is in its collapsed position.

FIG. 56 is a cross-sectional view of the embolic protection device of FIG. 54 taken along line 56—56.

FIG. 57 is an elevational view of a proximal end of an expandable strut assembly showing a dampening member associated with a filtering assembly which is rotatably attached to a guide wire.

FIG. 58 is a cross-sectional view of the proximal end of a filtering assembly made in accordance with the present invention showing one particular example of attaching an obturator to a strut assembly.

FIG. 59 is an elevational view depicting an embolic protection device made in accordance with the present invention which includes a coating that reduces the frictional coefficient between embolic debris and the struts of the strut assembly to help prevent embolic particles from sticking to the strut assemblies.

DETAILED DESCRIPTION OF THE PREFERRED EMBODIMENTS

Figure 5:
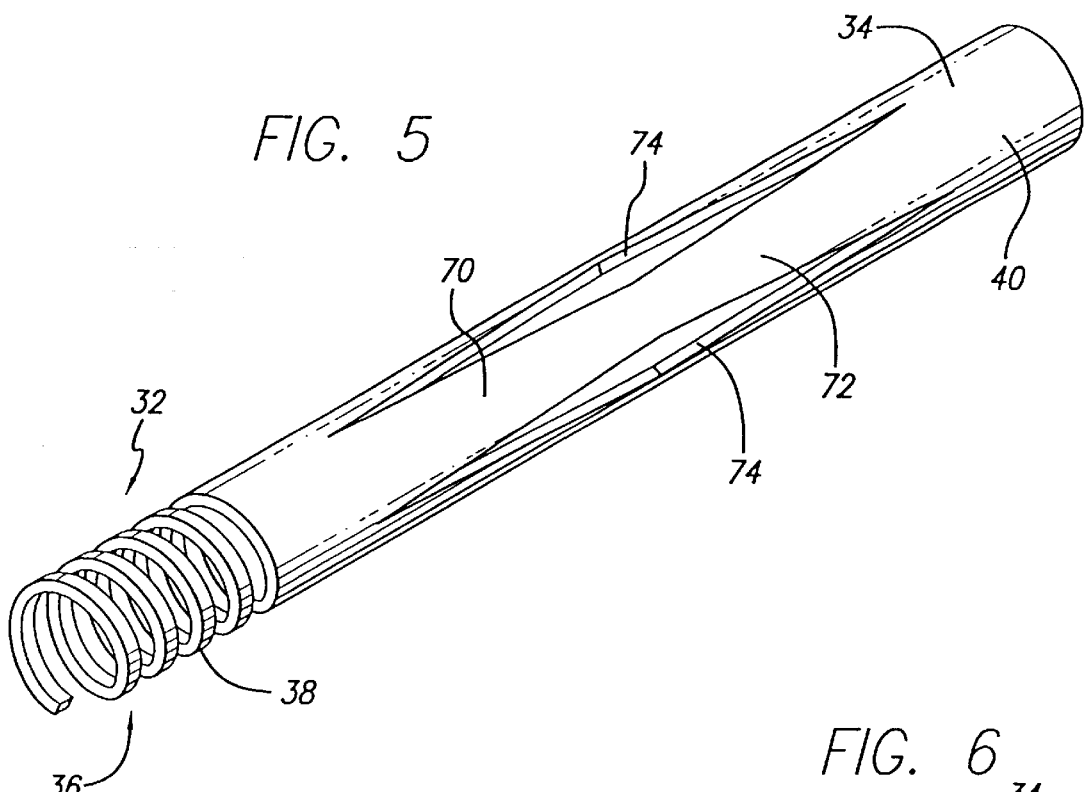
FIG. 5 is a perspective view of another embodiment of an expandable strut assembly which forms part of the filtering assembly of the present invention in its collapsed position.

Turning now to the drawings, in which like reference numerals represent like or corresponding elements in the drawings, FIGS. 1 and 2 illustrate an embolic protection device 10 incorporating features of the present invention. In the particular embodiment shown in FIGS. 1 and 2, the embolic protection device 10 comprises a filtering or filter assembly 12 which includes an expandable strut assembly 14 and a filter element 16. The filter assembly 12 is rotatably mounted on the distal end of an elongated tubular shaft, such as a guide wire 18. Additional details regarding particular structure and shape of the various elements making up the filter assembly 12 are provided below.

The embolic protection device 10 is shown as it is placed within an artery 20 or other blood vessel of the patient. This portion of the artery 20 has an area of treatment 22 in which atherosclerotic plaque 24 has built up against the inside wall 26 of the artery 20. The filter assembly 12 is placed distal to, and downstream from, the area of treatment 22 as is shown in FIGS. 1 and 2. Although not shown, a balloon angioplasty catheter can be introduced within the patient's vasculature in a conventional SELDINGER technique through a guiding catheter (not shown). The guide wire 18 is disposed through the area of treatment and the dilatation catheter can be advanced over the guide wire 18 within the artery 20 until the balloon portion is directly in the area of treatment. The balloon of the dilatation catheter can be expanded, expanding the plaque 24 against the inside wall 26 of the artery 20 to expand the artery and reduce the blockage in the vessel at the position of the plaque 24. After the dilatation catheter is removed from the patient's vasculature, a stent 25 (shown in FIG. 2) could also be delivered to the area of treatment 22 using over-the-wire techniques to help hold and maintain this portion of the artery 20 and help prevent restenosis from occurring in the area of treatment. Any embolic debris 27 which is created during the interventional procedure will be released into the bloodstream and will enter the filtering assembly 12 located downstream from the area of treatment 22. Once the procedure is completed, the filtering assembly 12 is collapsed and removed from the patient's vasculature, taking with it all embolic debris trapped within the filter element 16.

One particular form of the expandable strut assembly 14 is shown in FIGS. 1–4. As can be seen in these figures, the expandable strut assembly 14 includes a plurality of radially expandable struts 28 which can move from a compressed or collapsed position as shown in FIG. 1 to an expanded or deployed position shown in FIG. 2. FIG. 3 shows a length of tubing 30 which can be utilized to form this expandable strut assembly 14.

The expandable strut assembly 14 includes a proximal end 32 which is rotatably attached to the guide wire 18 and a distal end 34 which is free to slide longitudinally along the guide wire 18 and also can rotate thereabout. The distal end 34 moves longitudinally along the guide wire whenever the struts move between the expanded and contrasted positions. The proximal end 32 includes a short tubular segment or sleeve 36 which has a coil spring formed therein which acts as a dampening member or element 38. The function of this dampening element 38 will be explained below. The distal end 34 of the tubing 30 also includes a short segment or sleeve 40 which is slidably and rotatably disposed on the guide wire 18.

Referring now to FIGS. 1, 2 and 7, the proximal end 32 of the expandable strut assembly 14 is mounted between a tapered fitting 42 located proximal to the dampening element 38 and a radiopaque marker band 44 located distal to the proximal end 32. The tapered end fitting 42 and marker band 44 fix the proximal end 32 onto the guide wire 18 to prevent any longitudinal motion of the proximal end along the guide wire but allow for rotation of the proximal end 32 and the filtering assembly 12. This particular construction allows the expandable strut assembly to rotate or "spin" freely about the guide wire. In this manner, the filtering assembly 12 will remain stationary should the guide wire 18 be rotated at its proximal end after the embolic detection device 10 has been deployed within the patient's vasculature. This is just one way of affixing the expandable strut assembly 14 onto the guide wire 18 to allow it to spin or rotate on the guide wire 18. Other ways of performing this same function can be employed with the present invention.

The benefits of mounting the proximal end 32 of the expandable strut assembly 14 to the guide wire 18 include the ability to precisely deploy the filtering assembly 12 within the artery once the guide wire 18 has been positioned in the patient's vasculature. Since the proximal end 32 cannot move longitudinally along the guide wire, the physician can be sure that the filtering element 12 will be placed exactly where he/she places it once the restraining sheath 46 is retracted to allow the expandable struts to move into their expanded position. Additionally, since the proximal end 32 is affixed to the guide wire, any movement of the filtering element as the restraining sheath 46 is retracted should not occur. Since the expandable struts 28 can be made from self-expanding materials, there may be some stored energy in the filtering assembly 12 as it is held in its collapsed position by the restraining sheath 46. As that restraining sheath 46 is retracted, there can be a frictional build-up which can cause the strut assembly 14 to move outward if the proximal end 32 were not affixed to the guide wire 18. As a result, if the ends of the strut assembly 14 were not somehow fixed onto the guide wire, there could be a tendency of the filtering element 12 to spring out of the restraining sheath 46 as it is being retracted. As a result, the placement of the filtering element 12 will not be as accurate since the physician will not be able to predetermine if and how much the filtering assembly 12 would move as the restraining sheath 46 is retracted.

The dampening element 38, which in this particular embodiment of the invention is shown as a helical coil formed on the proximal end 32 of the strut assembly 14, helps to dampen any shockwaves (vibratory motion) which may be transmitted along the guide wire 18, for example, when interventional devices are being delivered or exchanged over the guide wire in an over-the-wire fashion. Similarly, this dampening element 38 also helps dampen any shock forces which may result as the restraining sheath 46 is retracted to allow the radial expandable struts to move into their expanded position as shown in FIG. 2. The helical coil can also act as an attachment method which helps retain guide wire flexibility. The dampening element 38 should somewhat also dampen shock which may be created as the recovery sheath 48 (FIG. 2) contacts the struts to collapse the filter assembly 12 when the embolic protection device is to be removed from the patient's vasculature. As a result, this dampening element 38 will absorb and dissipate forces which would otherwise act on the expanded filtering assembly 12 and could cause the assembly 12 to scrape the inside wall 26 of the artery 20 or otherwise cause trauma to the vessel. This dampening element 38 also helps prevent displacement or misalignment of the filter element within the artery which may result from a sudden shock transmitted along the guide wire 18.

The filter element 16 utilized in conjunction with this preferred embodiment of the invention includes a tapered or cone shaped section 50 which has a plurality of openings 52 which allow the blood to flow through the filter 16 but captures emboli within the inside of the cone shaped section. The filter element 16 includes a short proximal section 52 which is integral with the cone shaped section 50 and expands to a substantially cylindrical shape when the struts 28 of the strut assembly 14 are deployed. The inlet opening 51 allows any embolic debris 27 to enter the filter element 16 for capture. This short cylindrical section 52 also serves as a suitable location where the filter element 16 can be adhesively or otherwise affixed to each strut 28 of the strut assembly 14. The filter element 18 includes a short distal cylindrical section 54 which is integral with the remaining sections of the filter and is attached to the sleeve segment 40 which forms the distal end 34 of the expandable strut assembly 14. This distal cylindrical section 54 can be attached to the sleeve 40 using adhesives or other bonding techniques.

Referring again to FIG. 1, the filter assembly 12 is maintained in its collapsed or compressed position through the use of a restraining sheath 46 which contacts the struts 28 and filter elements 16 to maintain the filtering assembly 12 collapsed. Although not shown, the guide wire and restraining sheath 46 have proximal ends which extend outside the patient. The struts 28 can be manipulated into the expanded position by retracting the restraining sheath 46 (via its proximal end) to expose the struts 28. Since the struts 28 are self expanding, the removal of the restraining sheath 46 allows the struts 28 and filter element 16 to move to the expanded position within the artery 20.

The guide wire 18 includes a small sphere 56 affixed thereto which is beneficial during the delivery of the embolic protection device 10 into the patient's vasculature. This sphere 56 is approximately as large as the inner diameter of the restraining sheath 46 and is utilized as a "nosecone" to prevent possible "snow plowing" of the embolic protection device as it is being delivered through the patient's arteries. The sphere 56 is atraumatic and has a smooth surface to help the embolic protection device travel through the patient's vasculature and cross lesions without causing the distal end of the restraining sheath 46 to "dig" or "snow plow" into the wall of the arteries. When the embolic protection device 10 is to be removed from the patient's vasculature, a recovery catheter 48 is utilized to collapse and recover the filter assembly 12. (FIG. 2). Generally, this recovery sheath 48 has a slightly larger inner diameter than the restraining sheath 46 since the struts 28 are now deployed and may require some increased hoop strength at the distal end 47 of the recovery sheath 48 to properly move the strut assembly 14 back into its collapsed position. The collapse of the expandable strut assembly 14 can be accomplished by holding the guide wire 18 and moving the proximal end (not shown) of the recovery sheath 48 forward which will move the distal end 47 of the sheath 48 over the struts 28. Alternatively, the recovery sheath 48 can be held stationary while the proximal end of the guide wire is retracted back to pull the entire filter assembly 12 into the sheath 48. Upon collapse of the filter assembly 12, any embolic debris generated and entering the bloodstream during the interventional procedure will remain trapped inside the filter element 16 and will be withdrawn from the bloodstream when the embolic protection device 10 is removed from the patient's vasculature.

A radiopaque marker 58 located approximately at the longitudinal center of the expandable strut assembly 14 is also affixed to the guide wire 18 to provide the physician with a reference marker when positioning the device within the patient's artery 20.

The number of struts 28 formed on the expandable strut assembly 14 can be any number which will provide sufficient expandability within the artery to properly deploy and maintain the filter element 16 in place. In the embodiment shown in FIGS. 1 and 2, the expandable strut assembly has four self-expanding struts 28. Likewise, the particular size and shape of each strut 28 can be varied without departing from the spirit and scope of the present invention. In this preferred embodiment, the strut pattern includes a first portion 60 having an inverted triangular shape, a substantially straight center section 62, and a second inverted triangular shaped section 64 which completes the strut. This particular strut pattern is preferred since the design provides greater strength in regions of the strut where there would be a tendency for the strut to break or become weakened. These regions include the very proximal and distal ends of each strut which are designed with a wider base. This particular design also allows the composite strut assembly to open and close more uniformly which is beneficial especially when collapsing the struts for removal from the patient. Additionally, the center section 62 allows the struts 28 to expand to a greater volume, which allows a larger filter element to be placed on the strut assembly 14, if needed.

Referring now specifically to FIG. 4, a plan view of a rolled out flat sheet of the tubing 30 utilized to form the struts 28 is shown. As can be seen from FIG. 5, a particular design pattern is cut into wall of the tubing 30 in order to form each strut 28. In the case of the embodiment shown in FIG. 3, that pattern consists of a truncated diamond shape 65 which helps form the first section 60, the center section 62 and the second section 64. By selectively removing portions of the tubing 30 through laser cutting or other suitable means, each particular strut 28 can be made to a precise shape, width and length. This truncated diamond pattern 68 repeats as can be seen in FIG. 4 to provide uniform size to each of the struts 28 formed therein.

Figure 6:
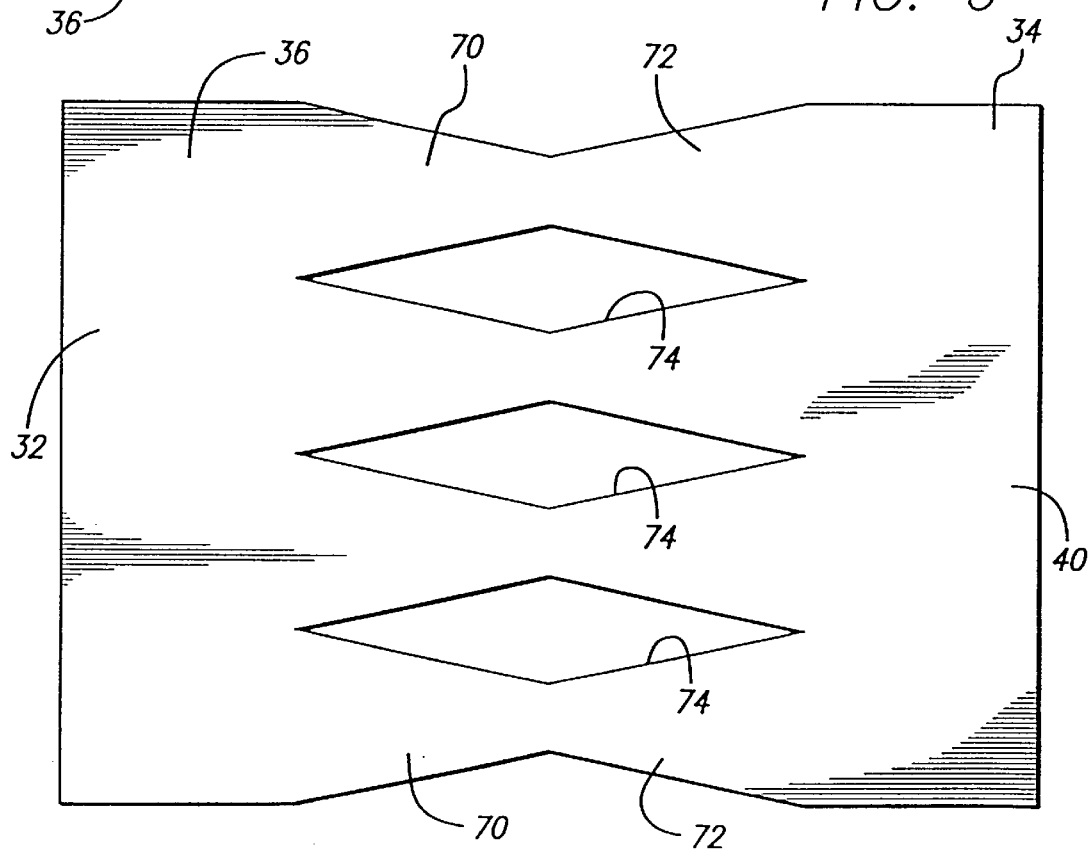
FIG. 6 is a plan view of a flattened section of the expandable strut assembly of FIG. 5 which shows an alternative strut pattern for the expandable strut assembly.

An alternative preferred embodiment of the expandable strut assembly 14 is shown in FIGS. 5 and 6. This particular strut assembly 14 is similar to the one shown in FIGS. 3 and 4 except that there is no center section. The struts 68 shown in FIGS. 5 and 6 consist of a pair of inverted triangles which form a first section 70 and a second section 72. The plan view of the flat sheet of the tubing 30 used to form the strut assembly 14, as shown in FIG. 6, shows a repeating diamond pattern 74 which is cut into the tubing to create each individual strut 28. Again, this particular pattern is preferred since greater strength is provided near the proximal and distal ends of each strut where there would be a tendency for breakage or a weakness of the strut. When the particular pattern is cut into the tubing, whether it be the pattern shown in FIGS. 3–4 or 5–6 or some other pattern, the sleeve 36 which forms the proximal end 32 of the strut assembly 14 can thereafter be similarly cut to create the helical coil which forms the damping element 38 on the strut assembly 14.

Figure 9:
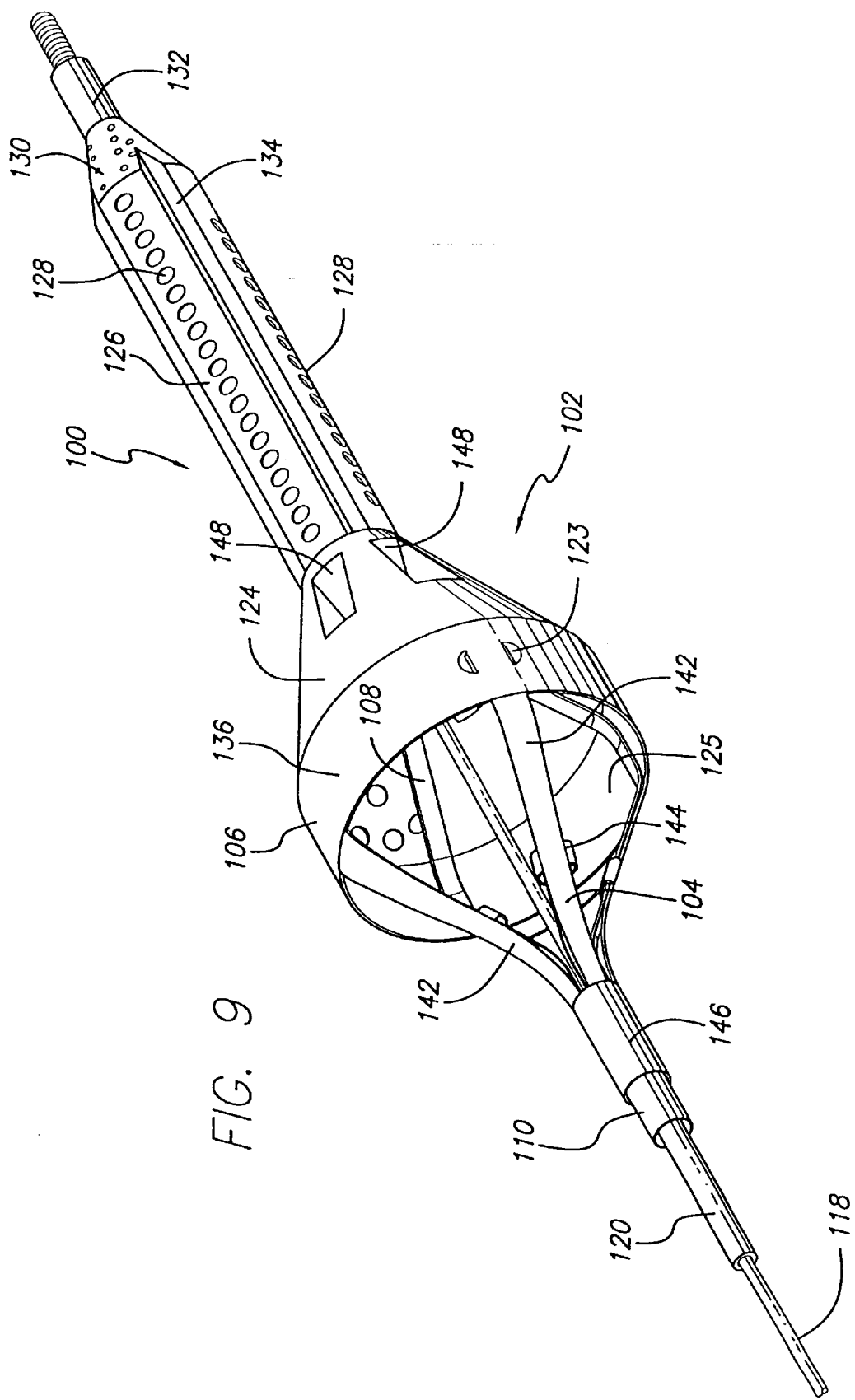
FIG. 9 is a perspective view of another embodiment of an embolic protection device made in accordance with the present invention.

Another embodiment of the present invention is shown in FIGS. 9–11. As can be seen in FIG. 9, the embolic protection device 100 includes a filter assembly 102 having an expandable strut assembly 104 and a unique filter element 106. The particular strut assembly 104 utilized with this embolic protection device 100 is similar to the structure of the expandable strut assembly 14 shown in the previous embodiment. The filter element 106, which will be described in greater detail below, is utilized in its expanded position to collect any embolic debris for removal from the blood stream of the patient.

The various elements making up this particular embodiment of the embolic protection device 100 are shown in FIG. 10. In this particular embodiment, the strut assembly 104 does not necessarily have to be made from a self-expanding material, as the strut assembly 14 disclosed in the previous embodiment. Rather, it could be made from stainless steel or other materials which require the application of external axial force on the proximal end 110 and distal end 112 of the strut assembly 104 to move the struts 108 between the contracted and expanded positions. As is shown in FIGS. 10 and 11, the proximal end 110 of the assembly 104 includes a short tubular or sleeve-like segment 114 and a similar distal segment 116. The struts 108 are moved from a contracted to a deployed position by imparting an inward axial force on the proximal end 110 and distal end 112 of the strut assembly 104. This can be accomplished by first attaching the distal end 112 of the assembly 104 directly to the guide wire 118. The proximal end 110 of the strut assembly 104, can then, in turn, be attached to an outer tubular member 120 which, along with the guide wire 118, has a proximal end which extends outside of the patient. The proximal ends (not shown) of both the outer tubular member 120 and the guide wire 118 can be manipulated by the physician to either impart an inward axial force on the two ends 110 and 112 of the strut assembly 104 to move the struts 108 to the deploy position or can be moved to impart an outward axial force on both ends 110 and 112 to collapse the struts 108 back to their collapsed position.

The struts 108 of the strut assembly 104 can be made from a piece of tubing (hypotube) in which select portions of the tubing are removed to form the particular size and shape of each strut. The strut assembly 104 could also be made from a self-expanding material such as nickel-titanium (NiTi) if desired. The struts 108 would then be biased into either the collapsed or expanded position with the outer tubular member 120 being used to move the proximal end 110 in order to expand or contract the strut assembly 104, depending upon, of course, the manner in which the expandable struts 108 are biased. Again, in the embodiment shown in FIG. 10, the struts 108 have a similar shape as the struts 28 shown in the embodiment of FIGS. 14. This particular embodiment of an embolic protection device thus eliminates the need to utilize both a restraining sheath and recovery sheath which would be otherwise needed in order to deploy and contract the embolic protection device. This particular design, however, does not allow for the filter assembly 102 to rotate as freely along the guide wire 118 as does the previous embodiments, although there can be some rotation. However, the outer tubular member 120 and guide wire 118 are utilized in a similar fashion by allowing interventional devices to be delivered over the outer tubular member in an over-the-wire fashion after the embolic protection device 110 is in place within the patient's vasculature.

It should be appreciated that the strut assembly 104 could also be made from a self-expanding material which maintains the struts 108 biased in their expanded position. The outer tubular member 120 would still be utilized in order to move the expanded struts 108 back into their collapsed position. The proximal ends of the outer tubular member 120 and guide wire 118 can be attached to a simple locking mechanism 600 (shown in FIGS. 39 and 40) which can be utilized to move the outer tubular member relative to the guide wire for maintaining the strut assembly 104 in its collapsed position until ready to be deployed within the patient's vasculature. It should further be appreciated that the particular embolic protection device 100 can also be modified to eliminate the outer tubular member 120 and be a self-expanding assembly like the one shown in FIGS. 1–2. In such a case, the proximal end 110 of the strut assembly 104 can be rotatably attached to the guide wire 118 with the distal end 112 being slidably mounted on the guide wire to allow for longitudinal motion and rotational motion about the guide wire 118.

The filter element 106 utilized in conjunction with this particular embodiment, or which can be utilized with any of the other embodiments disclosed herein, has a unique shape to provide a large reservoir to collect and maintain any embolic debris which may be trapped within the filter 106. Referring now to FIGS. 9–12, the various sections of the filter element 106 will be described in greater detail. It should be noted that the filter element 122 of FIG. 22 incorporates many of the same filter sections as the filter element 106 shown in FIGS. 10–12. Therefore, corresponding sections of these filters will be described simultaneously in order to better understand the principles underlying these unique filter elements. Both filter elements include a proximal cone section 124 which expands to fit within the diameter of the artery. This particular proximal cone section 124 blocks or funnels blood flow and embolic debris into the main or central filter 126. In both of the filter elements shown in FIGS. 9 and 22, the proximal cone section 124 includes a plurality of openings 128 which are utilized in filtering the embolic debris. However, it is possible to eliminate the openings 128 on the proximal cone section 124 to allow it to primarily direct blood flow and embolic debris directly into the central filter 126. This central filter 126 is integral with the proximal cone section 124 and includes a number of openings 128 utilized to permit blood flow through this section of the filter but to retain any embolic debris which is larger than the size of the openings 128. The openings 128 can be laser cut or otherwise punched into this central filter 126. This central filter 126 has a substantially cylindrical shape and acts as a large reservoir for holding the embolic debris. Ideally, it is sized such that when it is completely full of embolic material, it does not collapse to a smaller profile. However, is should be able to be withdrawn into the guiding catheter (not shown) when in its fully expanded condition with embolic debris trapped therein. Thus, the maximum outer expanded diameter of this central filter 126 should be smaller than the inner diameter of the guiding or sheath utilized in deploying the embolic protection device 100 in the patient's vasculature. The central filter can be made from a stiffer polymeric material which will maintain the shape and outer diameter to prevent the filter from collapsing after use. The resulting stiffer central filter cannot be squeezed during the collapse and removal of the filtering assembly from the artery which should prevent any trapped embolic debris from being squeezed out of the reservoir portion of the central filter.

Both filters 106 and 122 include a distal tapered region 130 which tapers down to the shaft of the guide wire 118. The taper of this particular region of the filter elements 106 and 122 facilitates the delivery of the embolic protection device 100 and helps prevent the "snow plow" effect when being delivered through the patient's vasculature. There is a small distal section 132 which also forms a part of the filter element and is utilized to attach the distal end of the filter directly onto the guide wire. This distal section 132 can be fastened utilizing well-known adhesives or other bonding techniques to permanently affix it to the guide wire 118 and prevent any embolic debris from escaping through the distal opening of this distal section 132.

Figure 16:
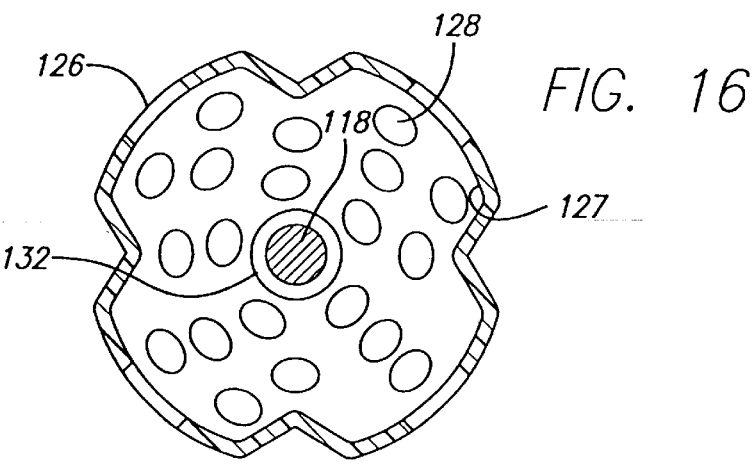
FIG. 16 is a cross sectional view of the central filter of the filtering device of FIG. 11 taken along lines 16—16.

The primary benefit of utilizing a large central filter with a proximal cone section is that there is a large filtering area provided by the central filter 126 which is less likely to squeeze out trapped embolic debris when the embolic protection device 100 is being removed from the patient's vasculature. As can be seen in FIG. 22, the central filter 126 has a general cylindrical shape while the central filter 126 of FIG. 9 can be a generally cylindrically shaped but can also include side creases 134 which produce a unique-looking design. The particular cross-sectional view of the central filter 126 of filter element 106 is shown in FIG. 16 and shows just one of a number of different shapes that can be used to create the central filter 126. In use, the filter element 122 of FIG. 22 would be attached to the strut assembly 104 and guide wire 118 utilizing adhesives or other bonding techniques.

The filter element 106 of FIG. 9 also incorporates some unique features which are not shown in the more basic filter design shown in FIG. 22. These advantages include the unique cross-sectional shape of the central filter 126 shown in FIG. 16, along with other features which help maintain the filter element 106 securely attached to the struts 108 of the strut assembly 104. Referring again to FIGS. 10–12, the filter element 106 includes a short outer rim 136 which is proximal to the end of the cone section 124 and has a large inlet opening 125 for receiving the blood flow and any embolic debris released into the bloodstream. This proximal outer rim 136 is ring-shaped and can be utilized to help attach the filter onto the struts 108 of the assembly 104. As can be seen in FIG. 10, this proximal outer ring is attached to the middle section 138 of each strut 108 and includes a tab 123 which can be wrapped around and attached to the strut 108. This proximal outer ring 136 also helps maintain the circular inlet opening 125 which must be expanded and maintained within the artery of the patient. Attached to the front of the outer rim 136 are restraining straps 142 which are likewise utilized to help hold the filter onto the struts 108 of the assembly 104. Each restraining strap 142 includes tab-like projections 144 which can wrap around each individual strut and be affixed thereto utilizing a bonding agent such as adhesive. These elements allow the restraining straps 142 to hold the filter element 106 onto the strut assembly 104. It should be appreciated that any number of different tab-like projections 144 can be utilized in conjunction with these restraining straps 142 to help secure the filter onto the assembly 104. The proximal end of each restraining strap 144 is attached to a sleeve 146 which also can be adhesively fixed to the tubular segment 114 formed at the proximal end 110 of the strut assembly 104. These various sections of the filter 106 can be made as one composite unit and can be formed by cutting a pattern into a pre-formed filter blank. Thereafter, the openings 128 along the length of the filter element 106 can be placed accordingly.

Figure 17:
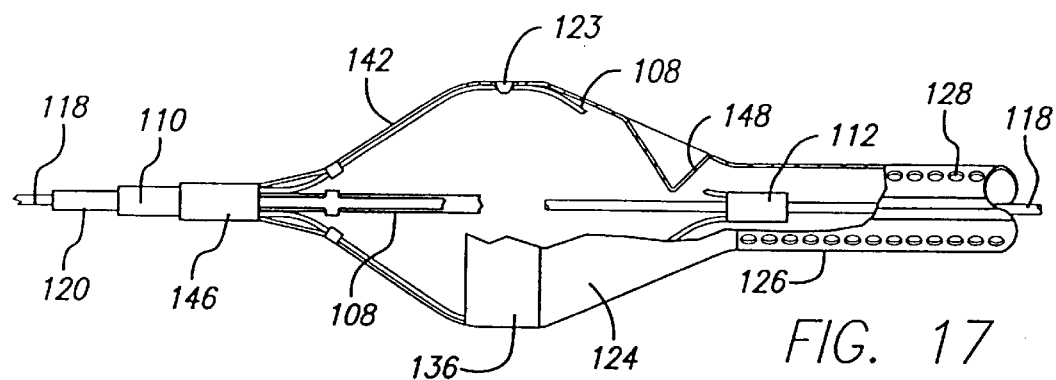
FIG. 17 is an elevational view, partially in cross-section and fragmented, of the embolic protection device of FIG. 11 showing the indented flaps of the proximal cone section in the expanded position.
Figure 18:
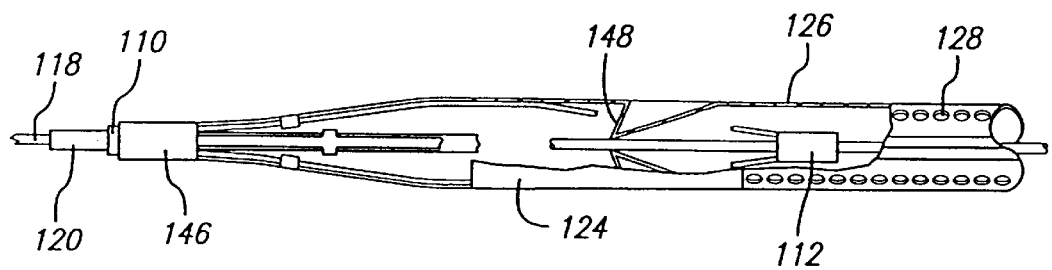
FIG. 18 is an elevational view, partially in cross-section and fragmented, showing the indented flaps of the proximal cone section in the collapsed position which causes the indented flaps to close the inlet opening of the central filter of the device.

The proximal cone section 126 of the filter element 106 shown in FIG. 9 includes a plurality of indented flaps 148 which are utilized to help close the opening of the central filter 126 when the proximal cone 124 is in its collapsed position. Each of these indented flaps 148, as shown in FIGS. 11, 17 and 18, are created such that as the proximal cone section 124 is being closed, the flaps join together and cooperate to form a barrier which prevents embolic debris from being released through the inlet opening 127 of the central filter 126. In the particular embodiment shown in FIG. 9, four such indented flaps can be utilized (only two of which are shown in FIGS. 11, 17 and 18) in order to create the barrier necessary to close the opening to the central filter 126. However, the number of indented flaps 148 and the size and shape of each flap 148 can be varied accordingly in order to create a protective barrier which helps prevent trapped embolic debris from escaping from the central filter 126 as the device 100 is being collapsed for removal from the patient.

Referring now to the FIGS. 19, 20 and 21, a variation of the indented flaps 148 is shown in the proximal cone section 124 of the filter element 106. As can be seen in these figures, there are a pair of flap portions 150 which are located within the proximal cone section 124 and are utilized as a mechanism for closing the inlet opening 127 of the filter element 106 when the filter assembly is collapsed. These flap portions 150 act much like the indented flaps 148 in that as the proximal cone section 124 is being collapsed, these flap portions 150 extend across the inlet opening 127 of the filter element 106 to create a barrier which helps prevent trapped embolic debris from being released back into the bloodstream. These flap portions 150 can be small appropriately shaped pieces which extend across the inlet opening when the filter is expanded but do not interfere with the flow of blood going into the filter element 106. Blood simply travels around the flap portions 150, along with any embolic debris, to the center filter 126 where the embolic debris will be trapped in the debris reservoir. This feature provides a preventive measure to diminish the possible release of trapped embolic debris when the embolic protection device 100 is being collapsed and removed from the patient's vasculature.

Referring now to FIGS. 14 and 15, an alternative form of the restraining straps and tabs which are utilized to affix the filter element 106 is shown. In these particular figures, the restraining strap 152 extends along each strut 108 and a tab like projection 154 is utilized to affix the restraining strap to each individual strut 108. Additional lateral strapping members 156 which extend laterally from each restraining strap 152 can also be utilized to help prevent the filter element 106 from moving off the strut assembly 104 during usage. These various designs shows alternative ways of affixing the filter element 106 onto the strut assembly 104. It should be appreciated that still other forms of attaching the filter element 106 to the strut assembly 104 can be utilized without departing from the spirit and scope of the present invention.

Another embodiment of the present invention is shown in FIGS. 23 and 24. In this particular embodiment, the embolic protection device 200 includes a filter assembly 202 having a strut assembly 204 and a filter element 206. The strut assembly 204 is similar to the strut assembly shown in FIGS. 1–4. It includes self-expanding struts 208 which are expandable from a collapsed position to a fully expanded position. This strut assembly 204 includes a proximal end 210 and a distal end 212. This strut assembly 204 can be made from a piece of tubing in which the struts are created by selectively removing portions of the tubing. In this particular embodiment, the tubing can be hypotubing made from a shape memory material such as nickel-titanium (NiTi). The resulting strut assembly 204 is normally biased to remain in the expanded position and require the applications of force on the ends 210 and 212 to deploy the struts 208 back to their collapsed position.

The proximal end 210 includes a segment of tubing 214 and the distal end 212 includes a similar segment of tubing 216 as well. The distal end 212 is permanently attached to the guide wire 218 near the distal coil 220 of the guide wire. The distal end 212 can be bonded using adhesives or welded, brazed or soldered to the guide wire 218. Likewise, the proximal end 210 of the strut assembly 204 can be bonded, welded, brazed or soldered to an elongated outer tubular member 222 which has a proximal end which extends outside of the patient. The proximal ends of the elongated tubular member 222 and the guide wire 218 can be manipulated by the physician to either open or close the filter assembly 202. A suitable locking mechanism 600 for maintaining the strut assembly 204 in its collapsed or closed position is disclosed in FIGS. 43 and 44 and is described in greater detail below.

The filter element 206 comprises of a cone shape portion 224 which is attached to the center section 226 of each strut 208. A plurality of openings 228 are laser cut or otherwise formed in the filter 206 which allows blood to flow through the filter but captures embolic debris which is larger than the size of the openings. This is another more example of a variation of the embolic protection device which can be made in accordance with the present invention.

Another embodiment of the present invention is shown as a embolic protection device 300 in FIGS. 25–28. Like the other embodiments, this device 300 includes a filtering assembly 302 which has an expandable strut assembly 304 and a filter element 306 attached to the strut assembly 304. Individual struts 308 are formed on the strut assembly 304 for moving the filtering element 306 into an expanded position within the patient's vasculature. The strut assembly 304 is some what similar similar to the previous embodiments disclosed above in that an outer elongated tubular member 310 is utilized in conjunction with a guide wire 312 to collapse and deploy the strut assembly 304. Although not shown in FIGS. 25 and 26, the outer tubular member 310 has a proximal end which extends with the proximal end of the guide wire outside of the patient to allow the physician to move the proximal ends to deploy or collapse the filtering assembly 302. The strut assembly 304 can be formed by selectively removing material from the outer tubular member 310 near its distal end to create the individual struts 308.

The struts will open upon application of an inward force on ends of the individual struts 308. Alternatively, the strut assembly 304 can be made from a piece of hypotubing which can be affixed to the outer tubular member 310 as is shown in some of the previous embodiments of the invention. The entire outer tubular member 310 with the strut assembly 304 is free to slide along the length of the guide wire 312 which allows the filtering assembly 302 to be positioned within the patient's vasculature in an over-the-wire fashion.

Figure 27:
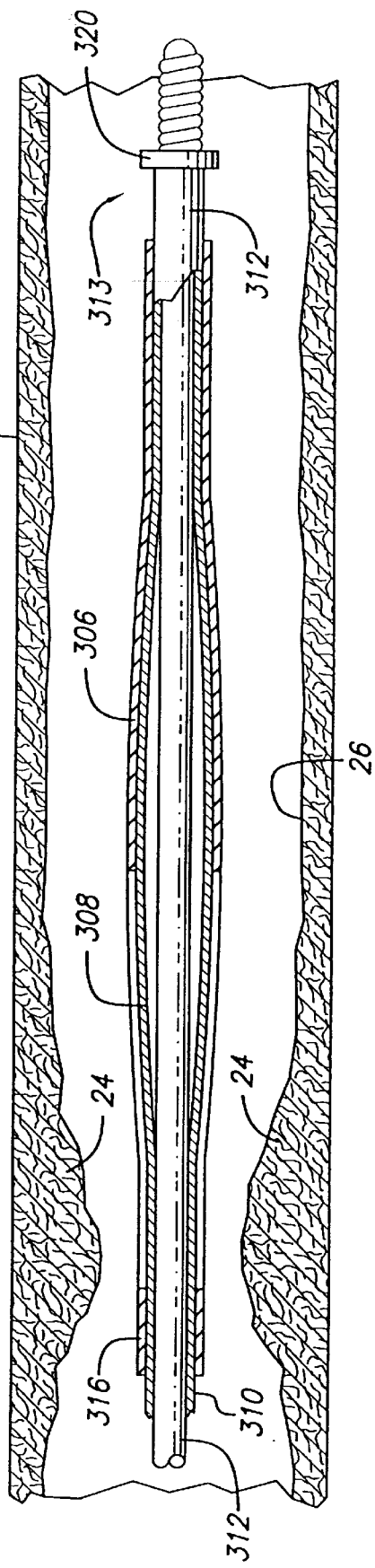
FIG. 27 is an elevational view, partially in section, depicting the embolic protection device of FIG. 25 in a collapsed position and disposed within a vessel.
Figure 28:
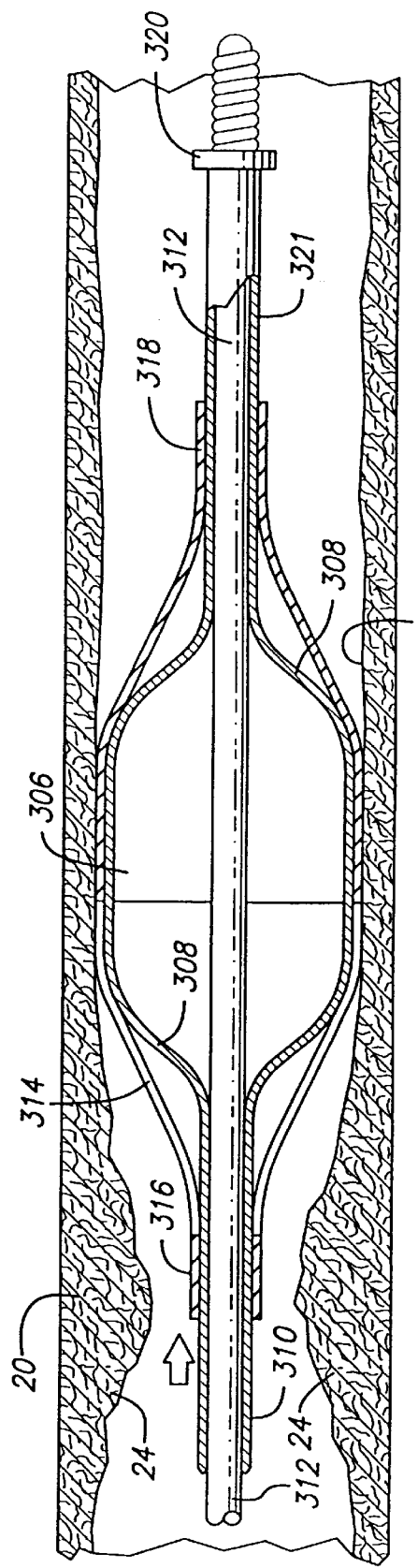
FIG. 28 is an elevational view, partially in section, similar to that shown in FIG. 27, wherein the embolic protection device is expanded within the vessel.

As can be seen in FIGS. 25–28, a stop element 320 is located near the distal coil 322 of the guide wire 312. This distal stop element 320 is utilized in conjunction with the outer tubular member 310 to produce the force necessary to expand the struts 308 into the expanded position. The embolic protection device 300 can be utilized in the following matter. First, the physician maneuvers the guide wire 312 into position past the lesion or area of treatment. Thereafter, the outer tubular member 310 with the strut assembly 304 is advanced over the guide wire 312 in an over-the-wire technique. The embolic protection device 300 remains in its collapsed position while being delivered over the guide wire 312 to the distal end 313 of the guide wire, as is shown in FIG. 27. Thereafter, the physician allows the distal sleeve 312 of the outer tubular member 310 to contact the stop element 320 located on the guide wire 312. By applying additional force at the proximal end of the elongated tubular member 310, the physician will cause the struts 308 to expand radially outward for deployment within the artery. The resulting expansion of the struts 308 thereby opens up the filter element 306 within the artery. The physician can then deliver interventional debris into the area of treatment and perform the procedure on the lesion. Any embolic debris which may be created during the interventional procedure will be collected within the interior of the filter 306.

A simple locking mechanism 600 device located at the proximal end of the outer tubular member and guide wire, as is shown in FIGS. 43 and 44, can be utilized to move and maintain the strut assembly 304 in the expanded condition. Thereafter, once the embolic protection device 300 is desired to be removed from the vasculature, the physician merely retracts the proximal end of the outer tubular member 310 to remove the force on the strut assembly 304 allowing the struts 308 to move back to the collapsed position. Thereafter, the embolic protection device 300 and guide wire 312 can be removed from the patient's vasculature.

The filter element 306 takes on a some what different shape from the previous filter element in that the main portion of the filter element 306 has a shape of a half of a dilatation balloon utilized in angioplasty procedures. Perfusion openings 313 are located on the filter elements 306 for allowing blood perfusion while capturing embolic debris. The proximal end of the filter element 306 includes a plurality of restraining straps 314 which extend to a proximal sleeve 316 which is affixed to the outer tubular member 310 proximal of the struts 308. The distal end 318 of the filter element 306 is also attached to the distal sleeve 321 which is formed on the outer tubular member 310 when the struts 308 are formed.

FIGS. 29 and 30 show another embodiment of a embolic protection device 400 made in accordance with the present invention. This particular embodiment is somewhat similar to the previous embodiments in that an external force is generated on the ends of the struts of the strut assembly to facilitate the outward expansion and inward contraction of the struts. Referring specifically now to FIG. 29, the embolic protection device 400 includes a filter assembly 402 having a strut assembly 404 which has a filter element 406 attached thereto. The individual struts 408 are formed on an outer tubular member 410 which has a distal end 412 attached to the distal end 413 of an inner tubular member 414. Both the inner member 414 and the outer member 410 have proximal ends which are located outside of the patient's vasculature. The struts 408 are radially expanded by moving the outer tubular member 410 relative to the inner tubular member 414 to apply the necessary axial force to cause the struts to deploy outward. An opposite axial force is necessary to cause the struts 408 to move back to the collapsed position when the device is to be removed from the patient's vasculature. In this embodiment, more than four struts 408 are used to expand the filter element 406 within the artery 420. Again, the number, size and shape of the struts 408 can be varied without departing from the spirit and scope of the present invention.

The filter element 406 also has the shape of one half of a dilatation balloon utilized in angioplasty procedures and includes openings 416 which allows blood to flow through the filter but captures the desired size of the embolic debris. The proximal end of the filter element 406 which includes an inlet opening 417 is attached to each of the center sections 418 of the struts 408. The distal end 420 of the filter 406 is attached to the distal end 412 of the strut assembly 404.

The lumen 422 of the inner tubular member 414 can be utilized for a number of purposes, such as blood perfusion past the deployed filter assembly 402 when placed in the artery. Therefore, should the openings 416 of the filter element 406 become clogged with debris which prevents blood from flowing through the filter, oxygenated blood can be perfused to downstream vessels via the inner lumen of the inner tubular member 414. This lumen can also be utilized for delivering the embolic protection device 404 over a guide wire in an over-the-wire fashion.

FIG. 31 and 32 show a variation of the previous filter element which can be utilized in conjunction with the present invention. The filter embolic protection device 400 is basically the same device shown in FIGS. 29 and 30 except that the filter element 430 has a different design. As can be seen in FIG. 31, the filter element 430 includes a proximal cone shape portion 431 which extends in front of the inlet opening 432 of the filter element 430. This type of filter 430 has advantages in that it may be easier to attach to the strut assembly 404. Additionally, the wall of the artery is insulated from the struts 408 by restraining straps 434. This device also has the benefits of being low profile and allows the use of any guide wire, as well as allowing for guide wire exchanges. This particular embodiment, like the previous embodiments, allows for the exchange of the interventional device in an over-the-wire procedure.

Referring now to FIGS. 33–38, two different embodiments of the present invention are shown which utilize a different mechanism for deploying the struts of the strut assembly. In FIG. 33, an embolic protection device 500 is shown as including a filter assembly 502 having an expandable strut assembly 504 and a filter element 506. As with the other embodiments, the strut assembly 504 includes a plurality of radially expandable struts 508 which are utilized to place the filter element 506 into an expanded position within the patient's vasculature. The mechanism for deploying the radially expandable struts 508 utilizes a number of self-expanding deployment members 510 which are attached to each of the struts 508 making up the expandable strut assembly 504. The self-expanding deployment members 510 are made from self-expanding materials, such as nickel-titanium alloy, which can be compressed to a very small profile and expanded to a rather large expanded position which moves the struts 508 and filter 506 to the fully expanded position. As is seen in FIGS. 33 and 34, there are a number of deployment members 510 which are located along the length of each of the struts 508. There is a proximal set 512 of deployment members 510 located along the proximal region of each strut 508. There is a center set 514 of deployment members 510 located at the center section of each stent 508. As can be seen in FIG. 34, the coverage of the filter element 506 begins at this center set 514. A third or distal set 516 of deployment members 510 is located on the struts in the region where the filter element 506 is placed to enhance the deployment of each strut.

As can be seen in FIG. 37, each deployment member 510 is basically a collapsible piece of self-expanding material which will expand to a final size when fully deployed. FIG. 38 shows an end view of the center set 514 and distal set 516 of the deployment members as they are located along the struts 508. Each of the sets of deployment members 510 will fully expand to a quarter-circle segment which cooperate to form a "ring" when the sets of the deployment members are fully expanded. As a result of using this particular construction, the filter element 506 will fully deploy and maintain a circular-shaped opening 507 which will contact the wall of the artery when the embolic protection device 500 is deployed within the patient's vasculature.

In the first embodiment of this particular embolic protection device 500, the distal end 518 of the expandable strut assembly 504 is permanently attached to the guide wire 520. The proximal end 522 of the strut assembly 504 is, in turn, attached to an elongated outer tubular member 524 which has a proximal end (not shown) which extends outside of the patient's vasculature along with the proximal end of the guide wire. The embolic protection device 500 can be moved into its collapsed position as shown in FIG. 35 by simply retracting the proximal end of the outer tubular member 524 to impart an outward force on the ends of the strut assembly 504. The force which will be imparted on the ends of the strut assembly 504 should be sufficient to collapse each deployment members 510 which will, in turn, cause each of the struts 508 to move back to the collapsed position. As with the other embodiments, once the struts 508 are placed in its collapsed position, the filter element 506 will likewise collapse and will trap and encapsulate any embolic debris which may have been trapped within the filter element 506.

Referring now to FIG. 36, an alternative embodiment of an embolic protection device similar to the one shown in FIG. 33 is disclosed. This particular embolic protection device 530 utilized the same filter assembly 502 and strut assembly 504 as shown in the previous embodiment. The differences between the strut assembly 532 of the embolic protection device 530 includes the elimination of the proximal set 512 of deployment members 510 from this strut assembly 532. Otherwise, the filter assembly 534 is virtually the same as the filter assembly 502 of the previous device 500.

The distal end 518 of the strut assembly 534 is also permanently affixed to the guide wire 520 in this particular embodiment. The proximal end of this particular strut assembly 534 is free to move longitudinally along the length of the guide wire when being moved from a deployed to a contracted position and visa versa. The mechanism for deploying the filter assembly 532 is restraining sheath 536 which places a force on the and deployment members 510 which prevent them from expanding until the restraining sheath 536 is retracted. Once the embolic protection device 530 is properly in place within the patient's vasculature, the proximal end (not shown) of the restraining sheath 536 is retracted to allow the deployment members 510 to open the struts 508 and filter element 506 to the fully expanded position within the artery. When the device is to be removed from the patient's vasculature, the restraining sheath 536 is placed against the proximal region 535 of the struts 508 and is retracted over the struts to force the deployment members 510 back into their collapsed position. Thereafter, any embolic debris which may be trapped within the filter element 506 is retained and safely removed from the patient's vasculature. A proximal set of deployment members 510 may not have to be used with this particular embodiment since there may be a need to reduce the amount of expansive force applied to the struts in this proximal region 535. However, it is still possible to place a first set of deployment members at this proximal region 535 provided that the sheath has sufficient strength to collapse the struts in this region.

The filter element 506 shown in FIGS. 33–38 is made from a mesh material which allows blood to perfuse therethrough but captures embolic material. The mesh material can be made from any interwoven fabric which contains small size openings which will trap the desired size of emboli. Alternatively, the filter 506 can be made from a polymeric material with perfusion openings found therein.

Referring now to FIGS. 39A, 39B and 40, an alternative strut assembly 550 which could be utilized in conjunction with any of the filtering assemblies made in accordance with the present invention is shown. The strut assembly 550 includes struts 552 and a deployment member 554 which is used to expand the struts 552 into the deployed expanded position. This deployment member 554 acts in the same manner as the previously described deployment members in that the deployment member 554 can be made from a self-expanding material which will expand to a final size once fully deployed. The deployment member 554 also could be collapsed to an unexpanded position when an external force is placed on the assembly to maintain the deployment member 554 in its collapsed position. As can be seen in FIGS. 39A, 39B and 40, the deployment member 554 has a serpentine pattern made of peaks 556 and valleys 558 which are accordingly attached to the struts 552 of the assembly 550. In these particular embodiment of the invention, the deployment member 554 has a sinusoidal wave pattern which includes the peaks 556 and valleys 558 that are attached to the ends of the struts 552. This particular pattern allows the struts to be offset or staggered from one another to allow the assembly 550 to be collapsed to a lower profile which enhances the assembly's ability to reach tighter lesions and to be maneuvered into even distal anatomy. The staggered strut design also increases the assembly's flexibility which enhances the ability to move the assembly within the patient's anatomy. A filter element could be likewise placed over or within the struts 552 to create a composite filter assembly. The deployment member 554 provides complete vessel wall opposition, forcing a seal of the filter edge to the wall of the vessel. The deployment member 554 can have multiple geometries without departing from the spirit and scope of the present invention. This particular strut assembly 550 also could be created from a lazed hypotube which incorporates the staggered strut design. The number of struts can be varied along with the particular lengths of the struts. Alternatively, the deployment member 554 could be made from a separate piece of material from the struts and could be attached using methods such as soldering, brazing or bonding, using suitable adhesives. As can be seen from FIGS. 39A and 39B, the attachment of the struts 552 to the peaks 556 and valleys 558 of the deployment 554 can be varied as shown. Both of these particular designs allow the strut assembly to be collapsed to a low profile.

Figure 41:
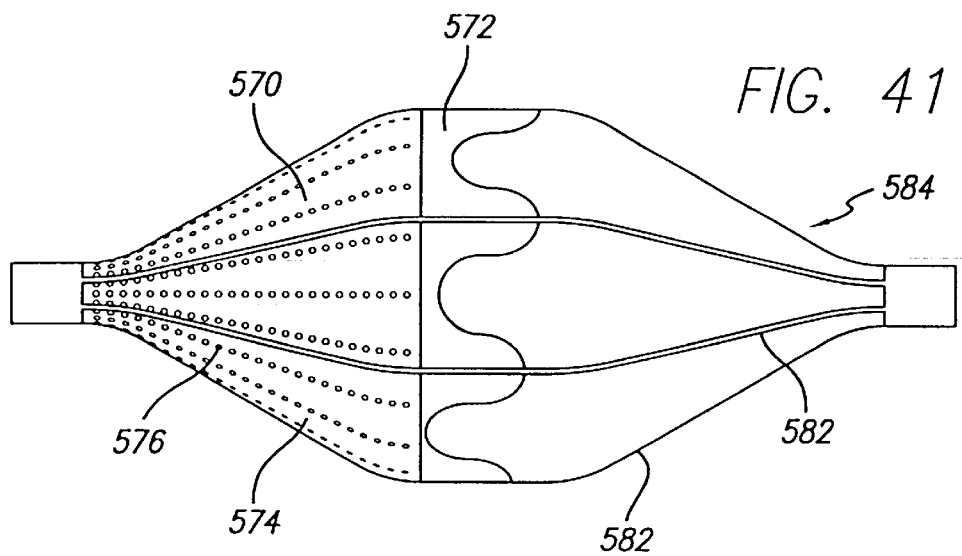
FIG. 41 is an alternative embodiment of a filter assembly with an alternative filter element made in accordance with the present invention.
Figure 42:
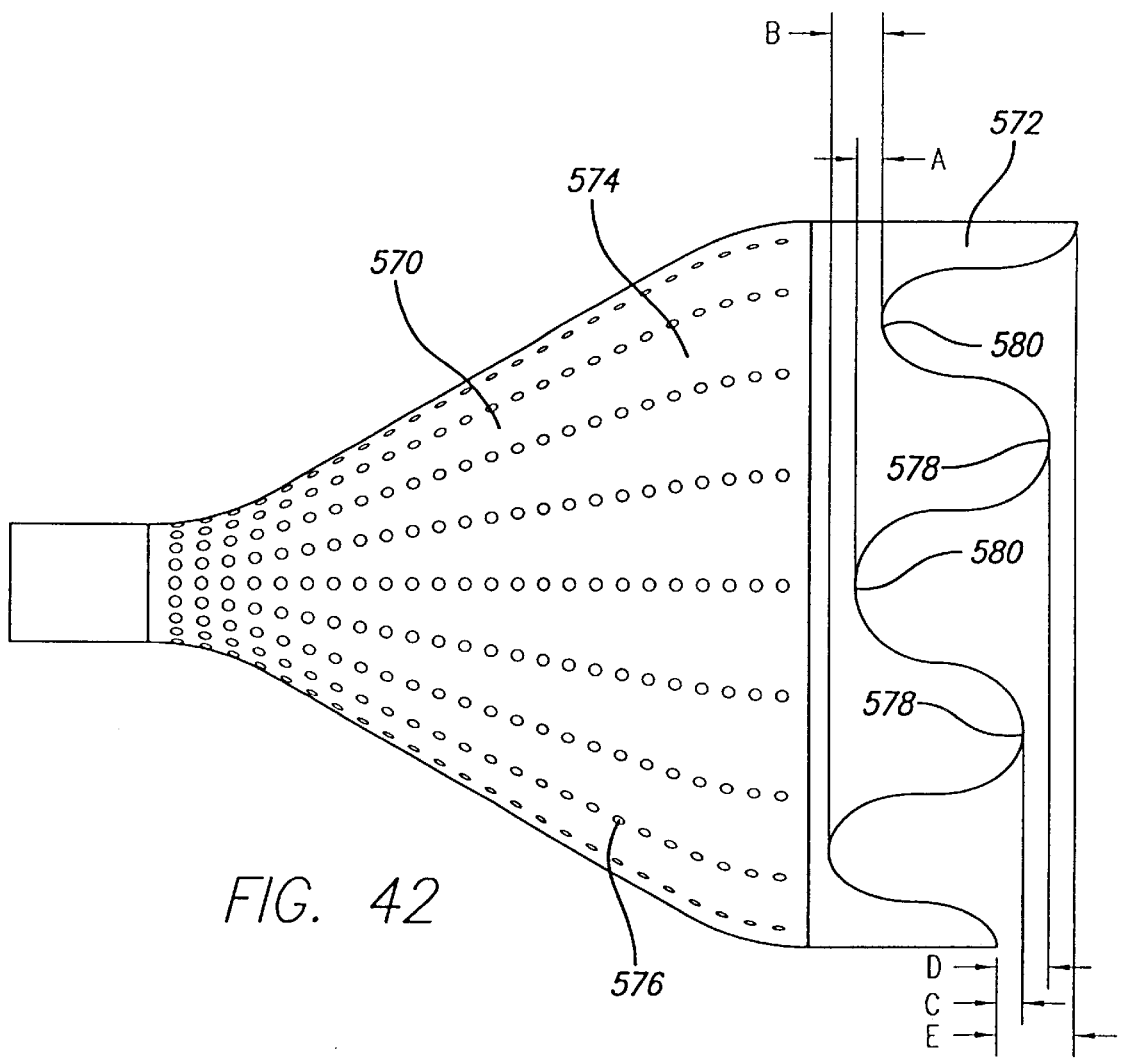
FIG. 42 is an enlarged side view of the filter element of the filtering assembly of FIG. 41.

Referring now to FIGS. 41 and 42, an alternative filter element 570 with an angulated filter edge 572 is shown which is used to help in the loading and retrieval of the embolic protection device into a restraining sheath. The filter element 570 is similar to the filters previously described in that the filter element 570 includes a central section 574 which has a plurality of openings 576 that are utilized in filtering the embolic debris. The filter element 570 includes an edge 572 which is configured similar to a crown, with pointed peaks 578 and valleys 580. This configuration of the filter edge 572 allows the filter to be incrementally introduced into the restraining sheath, thus preventing the material from entering the sheath all at once. As can be seen in FIGS. 41 and 42, the edge 572 has a somewhat sinusoidal configuration which would reduce the stress concentration in the valley regions 580 of the filter. The peaks 578 of the filtering element 570 would be matched up with the struts 582 of the strut assembly 584. The number of peaks 578 could vary with the number of struts 582 on the strut assembly 584. In this particular embodiment, the filtering element 570 could be placed within the inside of the strut assembly 584, or, alternatively, the filter could be placed on the outside of the assembly 584. It should be appreciated that other filter elements described herein also could either replace on the inside or outside of the strut assembly used in connection with a particular filtering assembly. As the strut assembly 584 is being loaded or retrieved, the peaks 578 of the filter element 570 would enter the restraining sheath first. This prevents all of the filtering material from entering the sheath at once, causing a gradual and incremental loading of the filter element 570 into the sheath. Additionally, dimensions A and B shown in FIG. 42 show the difference in the valley depths in the sinusoidal pattern of the filter edge 572. This allows for a variety of configurations. One possible configuration is A=B=0. Additionally, B≧A≧0 so that the loading of the filter into the sheath will be in a smooth operation. This particular configuration eliminates or virtually eliminates all of the valley portions 580 from entering the sheath at the same time. The filter edge 572 may or may not have openings 576. The peaks 578 can also have varying heights. Dimensions C, D and E shown in FIG. 42 shows a difference in the peak heights on the sinusoidal pattern of the filter edge 572. This particular pattern also allows for a variety of configurations. One possible configuration is C=D=E=0. Additionally, E≧D≧C≧0 to correspond, or alternatively, not to correspond with the depths of the valleys 580.

Referring now to FIGS. 45–48, an alternative embodiment of an embolic protection device 640 is disclosed. This particular embolic protection device 640 utilizes a filter assembly 642 and strut assembly 644 which is somewhat similar to the strut assembly 550 shown in FIG. 39B. The particular strut assembly 644 includes a set of proximal struts 646 attached to a deployment member 648 which moves between an unexpanded or collapsed position and an expanded position in the same manner as the previously described deployment members. This deployment member 648 can be made from a self-expanding material which will expand to a final diameter once fully deployed. This deployment member 648 is collapsible when a sheath or sleeve is placed over the assembly. A set of distal struts 650 are attached to the deployment member 648 and also are expandable and collapsible with the deployment member 648. The deployment member 648 has a substantial V-shaped wave pattern which permits the strut assembly to more easily collapse to a low profile. A filter element 652 is attached to the strut assembly 644 and has a shape much like the filter element 570 shown in FIGS. 41 and 42. The filter element 652 includes an edge portion 654 which is configured with alternating peaks 656 and valleys 658. This configuration of the filter edge portion 654 also allows the filter to be incrementally introduced into the restraining sheath 660, thus preventing the filtering material from entering the sheath 660 all at once. As can be seen in FIGS. 45 and 46, the filter element 652 has a somewhat tulip-like shape due to the construction of the peaks 656 and valleys 658. As is shown in FIG. 46, the peaks 656 of the filter element 652 are matched up with the wave pattern of the deployment member 648 and are attached thereto using adhesives or other bonding techniques. The filter can extend along and outside the struts with the edge portion 654 adhesively attached to the inside edge of the deployment member 648.

The filter element 652 can be made from a mesh material which allows blood to profuse therethrough but captures embolic material. The mesh material can be made from interwoven fabric which contains small size openings which would trap the desired size of emboli. Alternatively, the filter element 652 can be made from a polymeric material with profusion openings formed therein.

In this particular embodiment of the embolic protection device 640, an obturator 662 is located at the distal end 664 of the filter assembly 642 and is utilized for obtaining smooth deployment through the patient's vasculature. This particular obturator 662 acts much like the sphere 56 shown in FIGS. 1 and 2 which prevents "snow plowing" of the embolic protection device as it is being delivered through the patient's arteries. This obturator 662 also has a smooth surface which tapers from a smaller diameter distally to a larger diameter that corresponds to the outer diameter of the restraining sheath 660. A smooth outer surface is created when the obturator 662 and restraining sheath 660 are placed adjacent to each other. This obturator can be made from a material such as PEBAX 40D, or other polymeric materials or alloys which are capable of performing the desired function.

Figure 48:
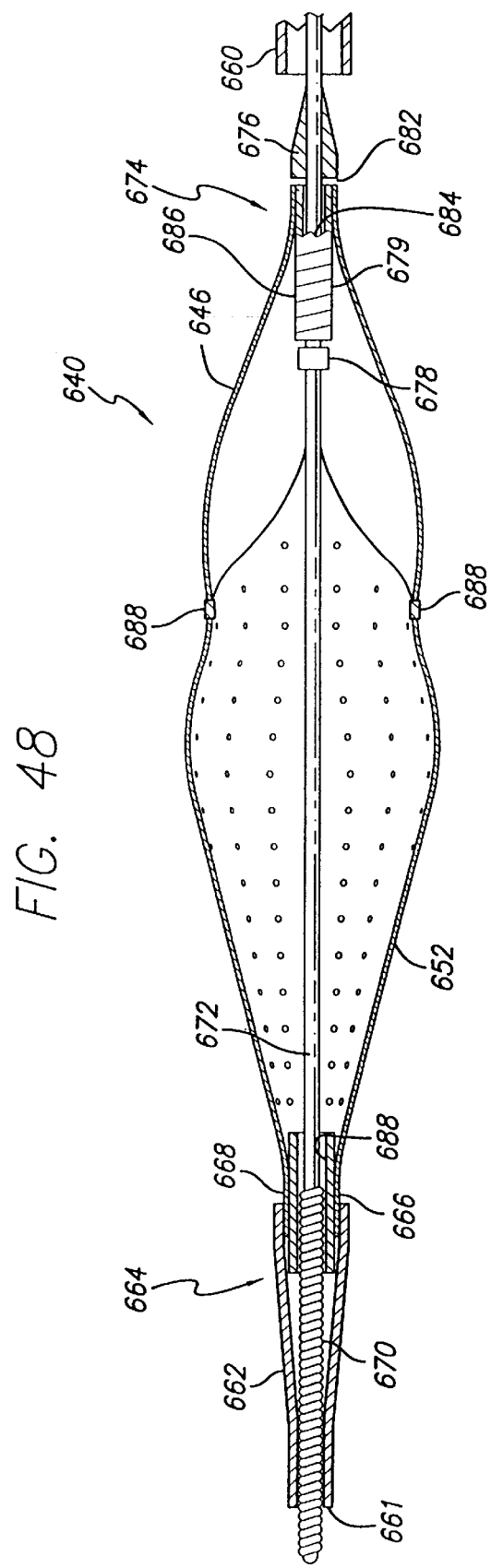
FIG. 48 is a cross-sectional view of the embolic protection device of FIG. 46.

As is shown in the cross-sectional view of the device in FIG. 48, the obturator 660 is attached (via adhesive or other bonding material) to a tubular member 666, which is made from a material such as polyimide tubing. This tubular member 666 is adhesively or otherwise attached to the distal ends 668 of the distal struts 650. The tubular member 666 is not, however, adhesively attached to the guide wire 672, but rather, is allowed to rotate free around the coils 670. The obturator 662 also extends over a portion of the coils 670 of the guide wire 672 and is free to rotate about the coils 670. The proximal end 674 of the filter assembly 642 is attached to the guide wire 672 in such a manner to allow it to rotate freely about or "spin" on the guide wire 672 as well. The filter assembly 642 is attached to the guide wire 672 much like the embodiment shown in FIGS. 1 and 2. As can be seen in FIGS. 46 and 48, a stop fitting 676 is attached to the guide wire 672 to prevent the proximal end 674 from moving past that particular fitting. A second stop fitting 678, located within the filter assembly 642, helps prevent the filter assembly 642 from moving axially any substantial distance along the guide wire 672.

The proximal ends 680 of the proximal struts 646 are attached to a pair of tubular segments 682 and 684 which are in a coaxial relationship. A marker band (not shown) can be partially sandwiched between these two tubular segments 682 and 684 to provide the physician with a reference when placing the embolic protection device 640 in the patient's vasculature. The tubular segments 682 and 684 are adhesively affixed to each other and the marker band to form a composite tubular extension member 686. This composite tubular extension member 686 extends between the two stop fittings 676 and 678. The extension member 686 may include a dampening element 679 which is formed on a portion of the segment to help dampen some of the vibratory motion which may be transmitted along the guide wire 672. It can be cut into the extension member 686 much like the dampening element 38 is cut on the embodiment shown in FIGS. 1–3. It should be appreciated that this extension member 686 can be formed from a single piece of tubing and need not be two separately formed segments glued together. This extension member 686 also helps to increase the torque response of the embolic protection device 640 on the guide wire and allows more room for the filter assembly to rotate, if needed.

Additional marker bands 688 can be placed on the strut assembly 644 to provide additional reference sources for the physician to rely on when maneuvering the device in the patient's arteries. Like the previously described filter assemblies, this particular filter assembly 642 will remain in place within the patient's vasculature, once deployed therein, and will remain stationary even if the guide wire 672 is rotated by the physician during an exchange of interventional devices along the guide wire. As a result, there is less chance of trauma to the patient's artery at the location where the filter assembly 642 contacts the wall of the artery.

The particular configuration of the filter assembly 642 and its attachment to the guide wire 672 allows the physician to eliminate any air bubbles which may be trapped within the restraining sheath 660 as it covers the filter assembly 642 in its collapsed state. The present design allows the physician to flush a solution, such as saline, through the lumen of the restraining sheath 660 out to its distal end to cause any trapped air bubbles to be vented through the distal opening 661 of the obturator 662. As a result, the possibility that an air bubble possibly could be released into the patient's artery can be virtually eliminated by thoroughly flushing saline through the restraining sheath 660 to eliminate any trapped air bubbles. The tubular member 666 acts as a conduit for the saline to flow out of the obturator 662. Fluid is allowed to flow through the restraining sheath 660 through the inner lumen 688 of the tubular member 666 and out the distal opening 661 of the obturator 662.

Referring now to FIGS. 49 and 50, another alternative embodiment of a embolic protection device 690 is shown. In this particular embodiment, the filter assembly 692 includes a strut assembly 694 which includes only a proximal set of struts 696 that are attached to a deployment member 698. This particular filter assembly 692 is somewhat similar to the assembly shown in FIGS. 45–48, except that a distal set of struts are not utilized. The filter element 700 is attached directly to the deployment member 698 and has a distal end 702 which is attached to a segment of tubing 704 made from a material such a polyimide. This tubing 704 extends from the proximal end 706 of the filter assembly 692 to the distal end 702 of the filter 700 and is rotatable on the guide wire 710.

In this particular embodiment, the proximal end 706 of the filter assembly 692 is attached directly to a tubing member 704. The proximal end 706 of the filter assembly 692 terminates in a collar 708 as is shown in FIGS. 49 and 50. It is attached to the tubing 704 using adhesives or other bonding techniques. This entire filter assembly 692, which includes the tubing member 704, is rotatable upon the guide wire 710 to allow the device to remain stationary within the patient's artery even if the guide wire is rotated by the physician during a device exchange. A stop fitting 712 located on the guide wire 710 acts to prevent the filter assembly 692 from moving axially along the length of the guide wire 710. The distal end 714 of tubing member 704 abuts against the most proximal coil 716 formed on the guide wire 710. In this manner, the coil 716 acts as a stop fitting to prevent axial movement of the tubing member 704 along the guide wire 710.

The distal end 702 of the filter 700 is attached to the tubing member 704 using adhesives or other bonding agents. The distal end 702 of the filter does not have to be movable axially along the guide wire, as with the previous embodiments, since the filter 700 itself is pliable and will move as the strut assembly 694 moves between its expanded and collapsed positions. When the strut assembly 694 is moved from its unexpanded to expanded position, the filter 700 will "stretch" somewhat as the deployment member 698 and struts 696 move outward and somewhat away from the distal end 702 of the filter 700. As with the previous embodiments, a restraining sheath (not shown) is utilized to move the filter assembly 692 between its expanded and unexpanded positions.

Figure 51:
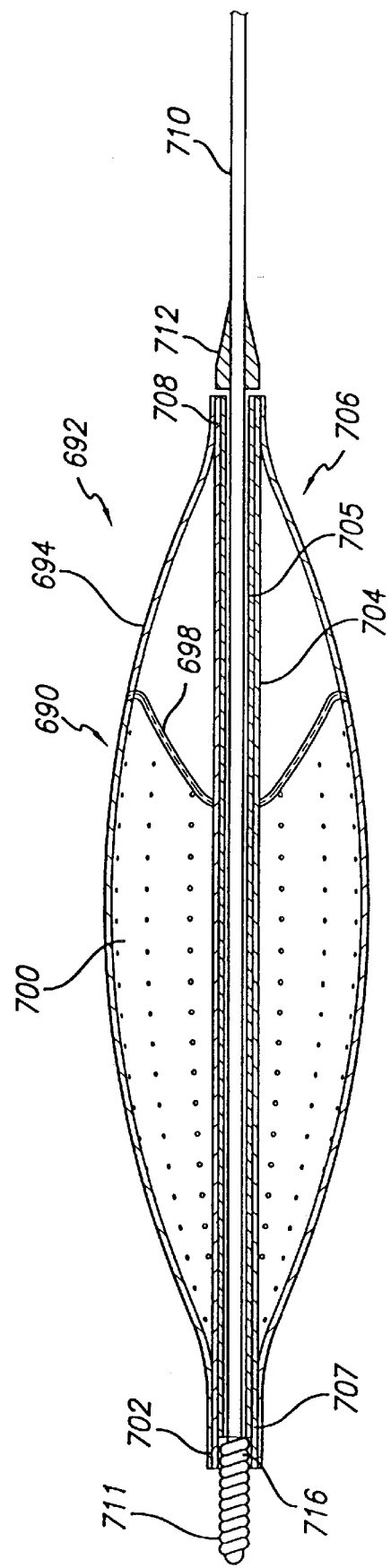
FIG. 51 is an elevational view, partially in cross-section, showing an alternative way to rotatably mount the filter assembly of FIG. 49 to the guide wire.

Referring now to FIG. 51, an alternative method for mounting the filter assembly 692 to the guide wire 710 is shown. In this particular embodiment, the strut assembly 694 is attached to an outer segment of tubing 704, which can be made from materials such as polyimide. This outer tubing 704 is in turn bonded, or otherwise attached to, an inner tubing 705 which is slightly shorter than the length of the outer tubing 704. For example, the outer tubing 704 and inner tubing 705 can be attached to each other utilizing a suitable adhesive. As can be seen in FIG. 51, the inner tubing 705 has a distal end 707 which abuts against the coil of the spring tip 711 of the guide wire 710. This allows a portion of the outer tubing 704 to extend over some of the proximal coils of the spring tip 711. The proximal ends of the outer tubing 704 and inner tubing 705 are adapted to abut the stop fitting 712 located on the guide wire which also helps prevent the filter assembly 692 from moving axially along the length of the guide wire. This inner tubing 705 can also be made from a number of different materials, including polyimide. Also, the length of the inner tubing 704 and outer tubing 705 can be adjusted such that the radiopaque spring tip 711 can be used to indicate corresponding device positions under fluoroscopy.

Figure 52:
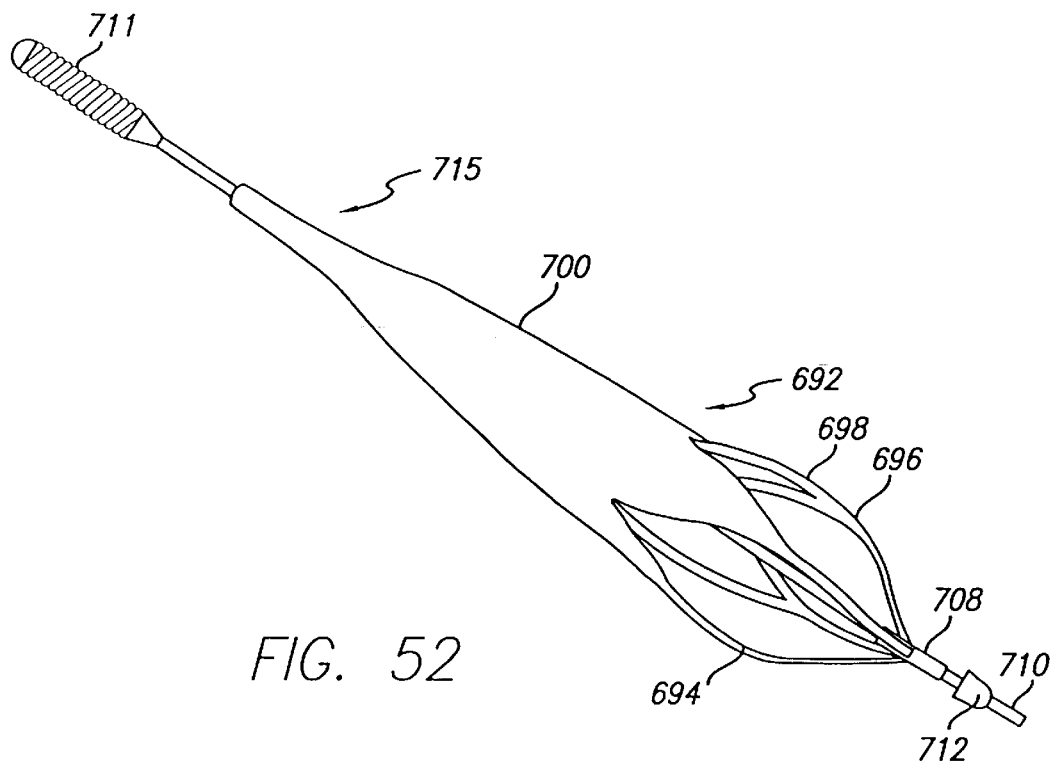
FIG. 52 is an elevational view of another embodiment of the embolic protection device make in accordance with the present invention.

Referring now to FIGS. 51 and 52, a variation of the filter assembly of FIGS. 49 and 50 is shown. In this particular embodiment, the filter assembly 692 includes a strut assembly 694 in which only a proximal set of struts 696 are attached to a deployment member 698. The filter element 700 is attached directly to the deployment member 698 and has a distal end which can be attached either directly to the guide wire 710 or to a small segment of tubing 713 (FIG. 53) which will allow the filter element 700 and strut assembly 694 to spin about the guide wire 710 in the manner which has been previously described.

In this particular embodiment, the inner tubing upon which the previously described embolic protection device 690 is mounted has been removed to obtain a slightly lower profile for the composite device. As can be seen in FIG. 51, the proximal end 706 of the filter assembly 692 terminates at a collar 708 which is directly attached to the guide wire 710. A stop fitting 712 located on the guide wire 710 acts to prevent the filter assembly 692 from moving axially along the length of the guide wire.

Figure 53:
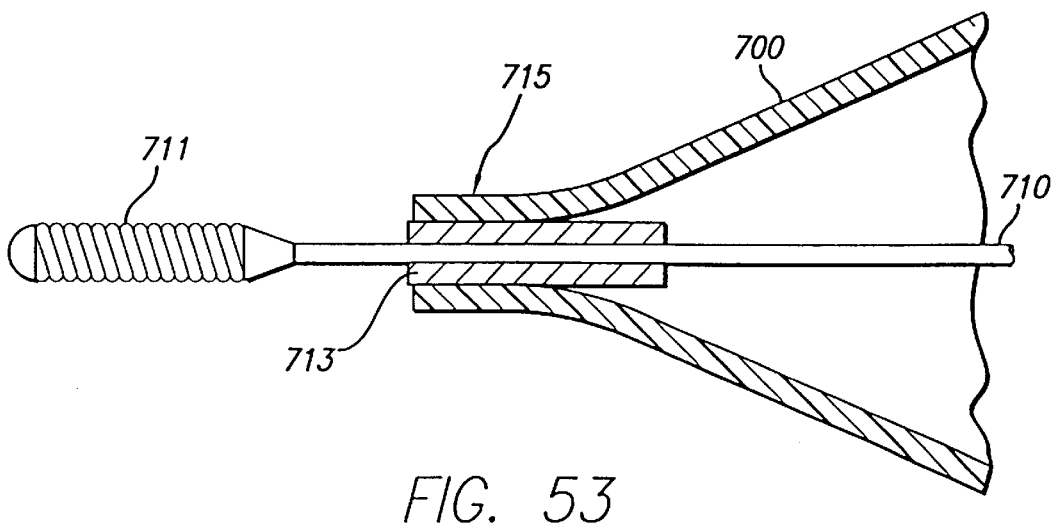
FIG. 53 is a cross-sectional view showing the distal end of the embolic protection device of FIG. 52.

Referring specifically now to FIG. 53, the distal end 715 of the filter element 700 includes the short segment of tubing 713 which allows the filter 700 to spin about the guide wire 710. This particular tubing can be made from any one of a number of different materials, including polyimide. Alternatively, the distal end of the filter 700 could be attached directly to the guide wire utilizing adhesives or other bonding techniques. The entire filter assembly 692 would still be able to rotate slightly on the guide wire since the filter element 700 can be made from a pliable material which would "twist" to a certain degree on the guide wire. This would still allow the strut assembly 694 to remain stationary in place within the patient's vasculature in the event that the guide wire is slightly rotated at the proximal end by the physician. Again, the filter element and strut assembly can be made in accordance with the methods described herein.

Referring now to FIGS. 43 and 44, a simple locking mechanism 600 for expanding and collapsing the filter assembly described herein are shown. These particular mechanisms are useful whenever the embolic protection device utilizes an inner shaft member and outer tubular member for moving the strut assemblies into the expanded or collapsed position. Referring first to FIG. 43, the proximal end 602 of the outer tubular member 604 is shown with a locking mechanism 600 which can be utilized to lock the embolic protection device in either an expanded or unexpanded position. The locking mechanism 600 includes an elongated slot 606 which is cut into the wall of the outer tubular member 604 and includes a first locking position 608 and a second locking position 610. The inner shaft member 612, which can be either a solid shaft such as a guide wire or a hollow tubular shaft, has a raised dimple 614 which moves within this elongated slot 606. This raised dimple 614 can be moved into either the first locking position 608 or second locking position 610 to either maintain the filter assembly in an expanded or unexpanded position. It should be appreciated that only two locking positions are shown on this particular embodiment, however, it is possible to use a number of different locking positions if the user desires to have several expanded positions. If the filter assembly is self-expanding, then a removable handle that pushes and pulls the inner and outer members could be used. The handle would push/pull the inner and outer members to hold the assembly closed, then be removed so that other interventional devices could be passed over the inner tubular member. Thereafter, the handle could be placed back onto the proximal ends of the inner and outer members to collapse and remove the filter assembly.

The proximal end 602 of the outer tubular member includes a small section of knurling 616, as does the inner shaft member 612, which provides the physician with a surface to grip when holding and maneuvering the proximal ends of these devices. The locking mechanism 600 can also include a biasing spring 618 located within the inner lumen 620 of the outer tubular member 604 for biasing the inner shaft member 612 with an outward force which maintain the raised dimple 614 near the first locking position 608. This biasing mechanism includes a shoulder region 621 located at the proximal end of the outer tubular member and a collar 622 located on the inner shaft member 612. The force of the spring 618 again helps to maintain the dimple 614 at or near the first locking position 608. Such a mechanism is preferable when the device is designed to be maintained in an unexpanded position until it is ready to be deployed. It may be beneficial to keep the filter assembly in its unexpanded position until ready for use since it is possible to cause damage to the filter assembly if left in an expanded position. When the filter assembly is desired to be placed into the deployed or expanded position, the physician merely grasps the proximal end of the inner shaft member and pulls it back until the dimple 614 is placed into the second locking position 610. When the strut assembly is made from elements which are self-expanding, then there may not be a need to have a biasing spring 618 since the struts on the strut assembly will act somewhat like a biasing spring to maintain the filter assembly in an expanded position.

Referring now to FIGS. 54–56, an alternative embodiment of a filter assembly 750 is shown. The filter assembly 750 includes a strut assembly 752 which includes a proximal set of struts 754 that are attached to a deployment member 756 which comprises a circumferential range which is integrally connected to each of the struts 754. A filter 758 is attached to the deployment member 756 and terminates at a distal end 760 which is slidable along the guide wire 762. A pair of stop fittings 764 and 766 allow the composite filter assembly 750 to rotatably spin on the guide wire 762 as has been previously described in connection with other embodiments disclosed herein.

The lengths of the four individual struts 754 which make up the strut assembly 752 as indicated by arrows $l_1$, $l_2$, $l_3$, and $l_4$ vary so that as the filter assembly 750 is being resheathed into the restraining sheath, the filter assembly 750 can be incrementally introduced into the restraining sheath, thus preventing the filter and individual struts from entering the sheath all at once. This particular arrangement helps in the collapse and resheathing of the filter assembly in the patient's vasculature, especially when the filter portion of the filter assembly is being resheathed.

As can be seen in FIG. 56, when the filter assembly 750 is expanded, the deployment member 756 is substantially round and has a slight distal bow when viewed longitudinally (as shown in FIG. 54), to facilitate collapsing of the assembly. In manufacturing this particular strut assembly 752, a tubing of material, such as nitinol, can be laser cut with the strut assembly heat set in the open (expanded) shape and then delivered and removed from the patient's vasculature with a low profile sheath. The longitudinal struts that open and employ the filter 758 can be intrically connected with the circumferential deployment member 756, which as shown in FIGS. 54–56 is a ring that can be cut from the same tubing as the struts. This deployment member 756 would completely contact with the lumen wall when fully deployed. As the struts are withdrawn into the sheath, the deployment member between each strut will be formed by bowing distally convex, as is shown in FIG. 55. Thus, a complete collapse, the deployment member 756, along with the filter 758, can be drawn into the sheath. Additionally, this deployment member 756 can be heat set completely round when fully deployed as is shown in FIG. 56.

Referring now to FIG. 57, a dampening element 770, similar to one which has been described above, is utilized accordance with a filter assembly 772 made in accordance with the present invention. In this particular embodiment, the dampening element 770 is shown as a separate coil spring which acts as a shock absorber when placed between the proximal end 774 of the strut assembly 776 and the proximal stop element 778. This particular arrangement is similar to the one shown in FIGS. 1–2 and 7, except that the dampening element 770 is a separate element from the strut assembly of 776. In this manner, the dampening element 770 can be made from a material which is different from the material used to form the strut assembly 776. This dampening element 770 also will act to dissipate at least some of the vibratory motion which may be transmitted along the guide wire 783.

Referring now to FIG. 58, and also to the particular embodiment shown in FIGS. 45–48, another method for attaching the obturator 660 to the strut assembly 644 is shown. In FIG. 58, the obturator 660 is shown as it is adhesively attached to the strut assembly 644 which allows for greater bond strength and flexibility during usage. As can be seen in FIG. 58, the distal end of the filter 652 is cut short of the distal end 664 of the strut assembly 644 to allow more of the strut assembly 644 to be exposed to the obturator 660. As a result, an adhesive 665 can be placed between the obturator 660 to directly contact the strut assembly 644 and achieve a stronger bond. The assembly still includes the tubular member 666, which be made from a material such as polyimide, or other suitable material, which allows the filter assembly 642 to spin on the guide wire 672. Again, the strut assembly 664 itself is bonded to this tubular member 666 to allow the distal end to spin freely about the guide wire 672. The bond strength is maximized through this increased surface area on the strut assembly 664 which is in direct contact with the obturator 660. In one embodiment, the tubular member 666 can extend out approximately 5 mm from the distal end of the strut assembly 644. This should eliminate any possible contact of adhesive to the guide wire. Again, this construction allows for a smooth rotation of the filter 652 on the guide wire. Any excess adhesive from the obturator should collect on the tubing to further increase the bond contact of the obturator to the filter assembly 642.

One of the requirements of the design of the filter assemblies shown and described herein is that embolic material must pass around proximal struts of the assembly into the filter portion of the device. Embolic debris which may collect or "stick" to a proximal strut may pose a problem when the filter assembly is being collapsed and withdrawn into the restraining sheath for removal from the patient's vasculature. Should embolic debris collect on a proximal strut, it may not be driven into the filter assembly for collection and could possibly be released into the patient's blood stream when the filter assembly is being collapsed for removal from the patient. In such an event, the physician must face the prospect of having to treat possible blockage to downstream vessels caused by such embolic debris.

In order to alleviate or help reduce this unwanted release of embolic debris from occurring, it is possible to selectively coat the strut assembly with a material which makes the struts "slippery", i.e., reduces the coefficient of friction between the embolic debris and struts, to help reduce the chances of embolic debris sticking to the struts.

Referring now to FIG. 59, a typical filter assembly 790 is shown including a strut assembly 792 which includes proximal struts 794 that are located upstream from the filter 796. It is in the region of these proximal struts that one or more pieces of embolic debris can collect, rather than being driven into the filter 796. However, the proximal struts 794 can be coated with a polymer which reduces the coefficient of friction to help prevent, or at least make it more difficult for, embolic debris to stick onto a strut. For example, a polymer coating can be placed selectively on these proximal struts. The intent in selectively depositing a slippery polymer coating to these struts is to prevent the coating from extending to areas of the strut assembly which experience high strain during device expansion. This may include the deployment member 798 which helps to deploy the filter 796 during usage. The high strain area of this deployment member may cause certain coating material to crack if the coating is not sufficiently elastic to "stretch" as the strut assembly expands. Alternatively, a very elastic coating material could be selected which will allow the entire strut assembly to be coated. Materials of interest include polyimide and PTFE coatings which could be applied to a nickel titanium strut assembly without significantly affecting the mechanical properties of the struts. It should be important to select a polymer coating which reduces the coefficient of friction yet does not affect the mechanical properties of the struts. If the material proves to be too stiff, the performance characteristics of the strut assembly could be affected. However, it is still possible to account for the stiff characteristics of the polymer through the strut design, i.e., the struts could be designed to be more flexible which would offset the stiffness caused by the polymer. Other coatings which could be utilized include hydrophillic coatings or heparin.

An alternative material for forming the filter used to trap the friable embolic debris utilizes an open-cell microporous material having a network-like porous structure that captures the debris. This particular filter material eliminates the need to either mechanically drill or laser cut the filter material to create a porous filter which still allows blood perfusion during the procedure. Use of the filter membrane in a microporous structure allows for perfusion and can be mechanically strong and more tear resistant than films with direct holes. This microporous structure also allows for more efficient trapping of emboli since the particles of debris have to travel through the intricate pattern of the filter in order to escape. Since a very fine micro-structure can be created, the chances of embolic debris passing through the microporous filter are extremely small.

Figure 60:
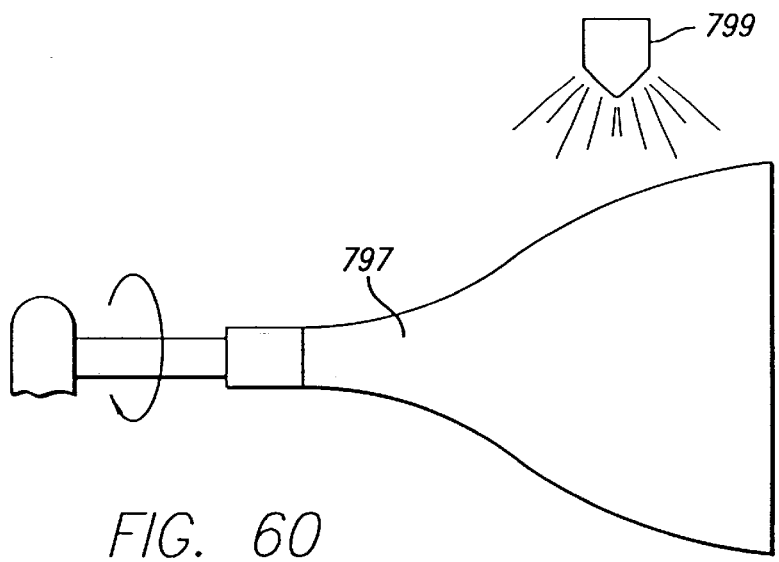
FIG. 60 is a schematic elevational view of a rotating mandrel utilized to create an open-celled microporous filtering material made in accordance with the present invention.
Figure 61:
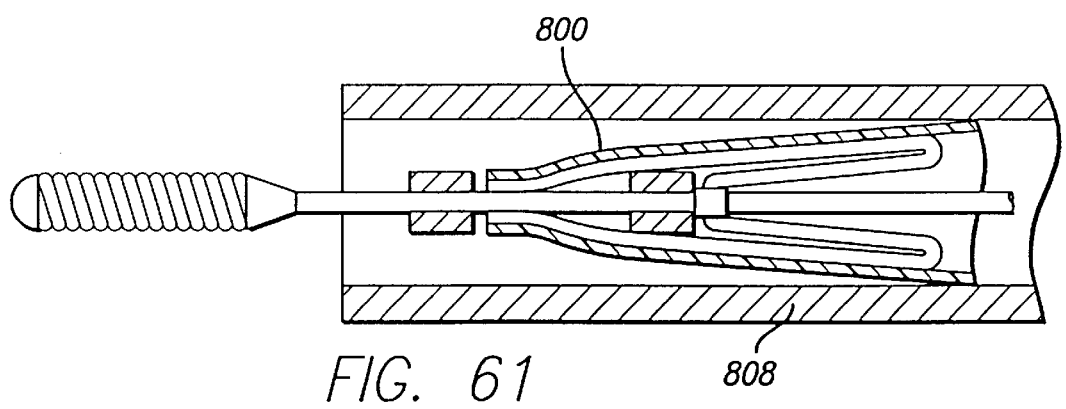
FIG. 61 is an elevational view of another embodiment of an embolic protection device embodying features of the present invention showing the expandable filter assembly in its collapsed position within a restraining sheath.

Referring now to FIG. 60, a cone-shaped rotating mandrel 797 is shown that can be utilized in creating a microporous film/membrane for forming the filters. The sequence of making the microporous film is a follows, namely, a polymer is first dissolved in a solvent to produce a polymer/solvent solution. This resulting polymer/solvent solution can be then sprayed or cast into the desired shape and thickness. For example, the film can be sprayed (via a spray nozzle 799 or by other means) on the rotating mandrel shown in FIG. 60 to create a cone-shaped structure. The rotating mandrel can be made in a number of sizes and shapes to create the desired filter element. Rotation of the mandrel usually improves the uniformity of the film thickness. After the polymer/solvent solution is sprayed or cast into the desired shape an thickness, it can then be either dipped or sprayed with a non-solvent before complete evaporation of the solvent occurs. This non-solvent induces phaseseparation of the polymer which creates the microporous structures throughout the material.

In one example of a microporous polymer film made in accordance with the present invention, the film can be made from Tecophilic 60D, a flexible polyurethane. Pellets of Tecophilic 60D can be dissolved in THF solvent, and sprayed onto a cone-shaped rotating mandel. The thickness of the film can be controlled by several factors, including the concentration of the solution, the rotational speed of the mandrel, and the amount of solution sprayed. After the film is cast, water (a non-solvent) then can be sprayed on the film to induce phase-separation and create the microporous structure. The porosity of the Tecophilic 60D film can be varied by controlling the type of solvent and concentration of the solvent used. Since this particular process is thermal dynamic, there should be no material restrictions. The choice of polymer will depend upon attributes like flexibility and strength of film.

Referring now to FIGS. 61–64, still another embodiment of an embolic protection device is disclosed. This particular embolic protection device 800 utilizes a filter assembly 802 and a strut assembly 804 mounted on the distal end of a guide wire 806. The strut assembly 804 is self-expanding so that a restraining sheath 808 is required to maintain the assembly in its collapsed position, ready for deployment within the patient's vasculature.

Figure 62:
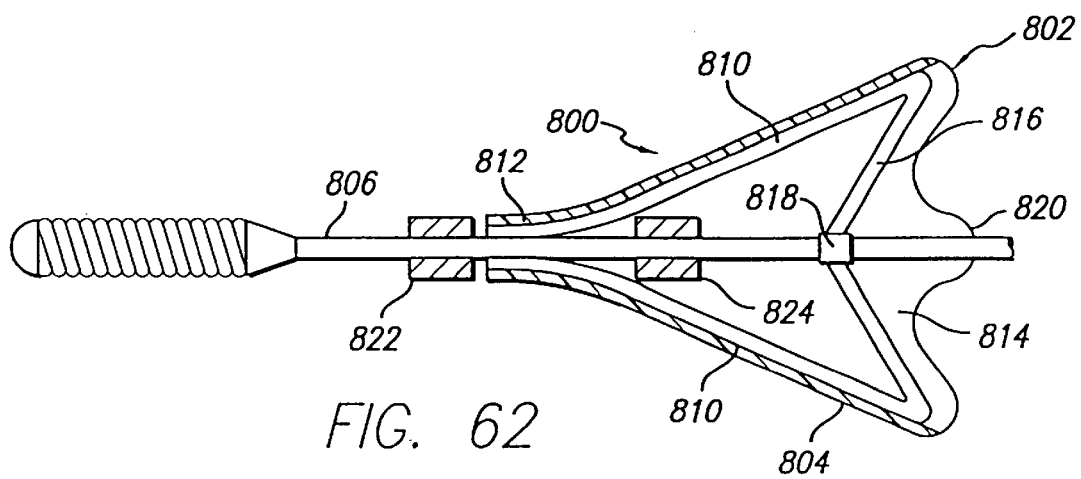
FIG. 62 is an elevational view, partially in cross-section, similar to that shown in FIG. 61, wherein the expandable filtering assembly is in its expanded position outside of the restraining sheath.
Figure 63:
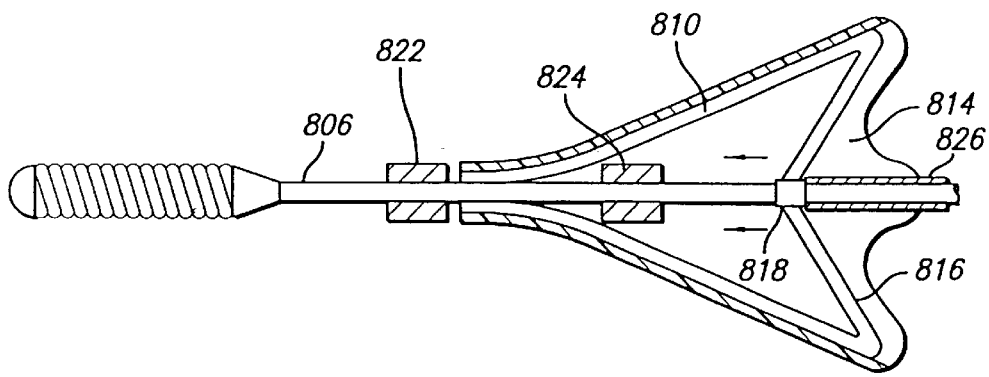
FIG. 63 is an elevational view, partially in cross-section, similar to that shown in FIG. 62, wherein an actuating member is being utilized to retract the expanded filtering assembly shown in FIG. 62 to its collapsed position.
Figure 64:
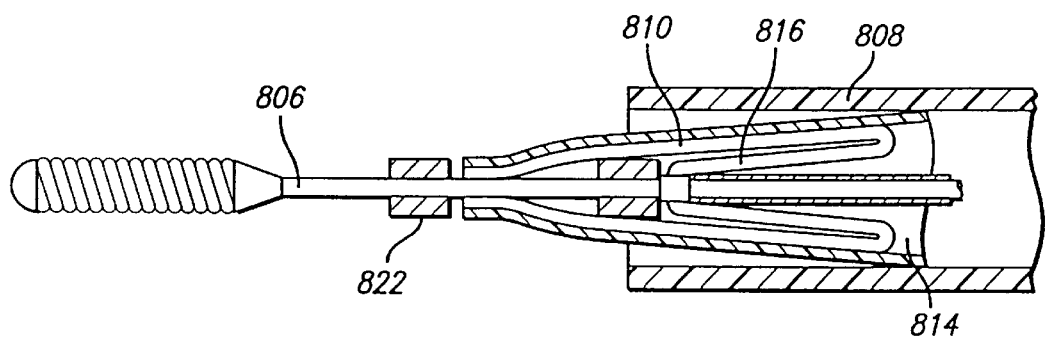
FIG. 64 is an elevational view depicting the embolic protection device of FIG. 63 as it is being moved into a restraining sheath.

The strut assembly 804 has a different configuration from the previously described strut assemblies. As can be seen in FIG. 62, the strut assembly 804 includes several forward radial expandable struts 810 which extend from the distal end 812 of the filter assembly 802. The forward struts 810 help to deploy the filter 814 in the patient's vasculature during usage. The forward struts 810 are attached to several activating struts 816 which are attached at a collar 818 that is slidable along the guide wire 808. The composite forward struts 810 and activating struts 816 provide a mechanism for opening the filter 814 once the restraining sheath 808 is retracted from the filter assembly 802. The filter 814 can have an scalloped filter edge 820 which, as described in a previous embodiment above, prevents the entire filter from entering the sheath at the same time when the device is being collapsed for removal from the patient's vasculature. A pair of stop fittings 822 and 824, which also act as radiopaque markers to assist in locating fluoroscopically within the patient, are located at the distal end 812 of the strut assembly 804 to attach the assembly to the guide wire 806. This particular design allows the filter assembly 802 to rotate or spin freely around the guide wire 806, while remaining fixed to the guide wire 806.

After the filter assembly 802 has been deployed and it is desired to remove it from the patient's vasculature, an outer tubular member 826 (shown in FIG. 63) is utilized to push the activating struts 816 and collar 818 distally to collapse the strut assembly 804 back to its collapsed position. This outer tubular member 826 should have sufficient stiffness to push the collar 818 distally along the guide wire 806. After the filter assembly 802 is collapsed, a restraining sheath is used to resheath the entire device for removal from the patient. (See FIG. 64.)

The materials which are utilized to create this particular embodiment are similar to these previously described and include self-expanding metals and alloys, such as nickel titanium, which can be utilized for the strut assembly. The filter can likewise be made from materials described herein. Likewise, the restraining sheath can be made from materials described herein, along with any other suitable materials, which should produce a flexible restraining device having sufficient hoop strength to hold the filter assembly in its collapsed position.

The strut assemblies of the present invention can be made in many ways. However, the one particular method of making the strut assembly is to cut a thin-walled tubular member, such as nickel-titanium hypotube, to remove portions of the tubing in the desired pattern for each strut, leaving relatively untouched the portions of the tubing which are to form each strut. The tubing may be cut into the desired pattern by means of a machine-controlled laser.

The tubing used to make the strut assembly may be made of suitable biocompatible material such as stainless steel. The stainless steel tube may be alloy-type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent.

The strut size is usually very small, so the tubing from which it is made must necessarily also have a small diameter. Typically, the tubing has an outer diameter on the order of about 0.020–0.040 inches in the unexpanded condition. The wall thickness of the tubing is about 0.076 mm (0.003–0.006 inches). For strut assemblies implanted in body lumens, such as PTA applications, the dimensions of the tubing maybe correspondingly larger. While it is preferred that the strut assembly be made from laser cut tubing, those skilled in the art will realize that the strut assembly can be laser cut from a flat sheet and then rolled up in a cylindrical configuration with the longitudinal edges welded to form a cylindrical member.

Generally, the hypotube is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished struts. The strut assembly can thus be laser cut much like a stent is laser cut. Details on how the tubing can be cut by a laser are found in U.S. Pat. No. 5,759,192 (Saunders) and U.S. Pat. No. 5,780,807 (Saunders), which have been assigned to Advanced Cardiovascular Systems, Inc. and are incorporated herein by reference in their entirely.

The process of cutting a pattern for the strut assembly into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

A suitable composition of nickel-titanium which can be used to manufacture the strut assembly of the present invention is approximately 55% nickel and 45% titanium (by weight) with trace amounts of other elements making up about 0.5% of the composition. The austenite transformation temperature is between about −15° C. and 0° C. in order to achieve superelasticity. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is approximately 0.5%. The breaking elongation is a minimum of 10%. It should be appreciated that other compositions of nickel-titanium can be utilized, as can other self-expanding alloys, to obtain the same features of a self-expanding stent made in accordance with the present invention.

The strut assembly of the present invention can be laser cut from a tube of nickel-titanium (Nitinol) whose transformation temperature is below body temperature. After the strut pattern is cut into the hypotube, the tubing is expanded and heat treated to be stable at the desired final diameter. The heat treatment also controls the transformation temperature of the strut assembly such that it is super elastic at body temperature. The transformation temperature is at or below body temperature so that the stent is superelastic at body temperature. The strut assembly is usually implanted into the target vessel which is smaller than the diameter if the strut assembly in the expanded position so that the struts apply a force to the vessel wall to maintain the filter element in the expanded position.

The piece of tubular hypotube which can be utilized in accordance with the present invention to form the strut assemblies can be one continuous piece which forms both the outer tubular member and the strut assembly as well. In some of the embodiments disclosed herein, the strut assembly is shown as being made from a short segment of hypotube which is selectively cut to form the strut patterns. Thereafter, the proximal end of the strut assembly is bonded to, either by adhesives, welding, brazing or soldering to the distal end of the outer tubular member. However, these two separate pieces can be formed from a piece of single tubing in a particular embodiment of the invention.

The dampening element which is shown in one of the embodiments of the present invention could also be used with any of the other embodiments disclosed herein. The dampening element could either be cut into the proximal end of the strut assemblies, as is shown in FIGS. 1 and 2, or an alternative dampening element could be attached to the strut assembly. For example, a separate spring made from a different material or similar material could be welded, brazed or soldered to the end of the strut assembly. Also, other dampening materials could be used besides a helical spring in order to achieve dampening. For example, a segment of elastomeric material could be bonded to the strut assembly as well to act as a "shock absorber" for the system.

The outer tubular member could be made from various materials such as stainless steel, nickel-titanium alloy or materials which have memory. As discussed above, when using a separate outer member attached to the strut assembly, the distal end can be easily affixed to the strut assembly by known bonding methods. The inner diameter of the outer tubular member must of course be comparable to the outer diameter of the inner shaft member to allow the outer tubular member to slide in a coaxial arrangement. The inner shaft member can also be made from stainless steel, nickel-titanium alloys or shape-memory materials. In one embodiment, the inner shaft member is shown as a tubular member which has an inner lumen which allows the device to slide over a guide wire in an over-the-wire fashion. Other embodiments show the inner shaft member as a guide wire or guide wire-like shaft. Generally, when the inner shaft member is utilized as a guide wire, it should include an atraumatic guide wire coil tip to prevent injury to the vessel as the guide wire is being maneuvered through the patient's vasculature. It should be appreciated that the coil tip does not have to be placed directly next to the filtering assembly in those embodiments which utilize a guide wire as the inner shaft member. The filtering assembly could be placed much more proximal to the coil tip to create a short, distal segment of guide wire which may be pre-bent by the physician to aid in steering through the patient's vasculature.

Again, the tubing or hypotube which could be utilized to create the strut assembly can be a nickel-titanium alloy, such as Nitinol, or other shape-memory materials. It is also possible to utilize stainless steel to form the strut assembly as well. The strut assembly could also be made from a self-expanding material even in embodiments in which the outer tubular member and inner shaft member are utilized to provide the axial forces necessary to expand or contract the device during use. Additionally, the strut assembly could be either biased to remain in its collapsed position or expanded position as may be desired. It should be appreciated that the stent assembly can be made from either pseudo elastic NiTi stressed induced martensite or shape memory NiTi.

One way of making the strut assemblies of the present device is to utilize a shape-memory material,such as nickel titanium, which has the struts cut utilizing a machine-controlled laser. A tubular piece of material could be utilized in this process. The strut assembly could be manufactured to remain in its open position while at body temperature and would move to its collapsed position upon application of a low temperature. One suitable method to allow the strut assembly to assume a change phase which would facilitate the strut and filter assembly being mounted into the restraining sheath include chilling the filter assembly in a cooling chamber maintained at a temperature below the martensite finish temperature through the use of liquid nitrogen. Once the strut assembly is placed in its collapsed state, the restraining sheath can be placed over the device to prevent the device from expanding once the temperature is brought up to body temperature. Thereafter, once the device is to be utilized, the restraining sheath is simply retracted to allow the filter assembly/strut assembly to move to its expanded position within the patient's vasculature.

The polymeric material which can be utilized to create the filtering element include, but is not limited to, polyurethane and Gortex, a commercially available material. Other possible suitable materials include ePTFE. The material can be elastic or non-elastic. The wall thickness of the filtering element can be about 0.00050–0.0050 inches. The wall thickness may vary depending on the particular material selected. The material can be made into a cone or similarly sized shape utilizing blow-mold technology. The perfusion openings can be any different shape or size. A laser, a heated rod or other process can be utilized to create to perfusion openings in the filter material. The holes, would of course be properly sized to catch the particular size of embolic debris of interest. Holes can be lazed in a spinal pattern with some similar pattern which will aid in the re-wrapping of the media during closure of the vice. Additionally, the filter material can have a "set" put in it much like the "set" used in dilatation balloons to make the filter element re-wrap more easily when placed in the collapsed position.

The materials which can be utilized for the restraining sheath and recovery sheath can be made from similar polymeric material such as cross-linked HDPE. It can alternatively be made from a material such as polyolifin which has sufficient strength to hold the compressed strut assembly and has relatively low frictional characteristics to minimize any friction between the filtering assembly and the sheath. Friction can be further reduced by applying a coat of silicone lubricant, such as Microglide®, to the inside surface of the restraining sheath before the sheaths are placed over the filtering assembly.

In view of the foregoing, it is apparent that the system and device of the present invention substantially enhance the safety of performing certain interventional procedures by significantly reducing the risks associated with embolic material being created and released into the patient's bloodstream. Further modifications and improvements may additionally be made to the system and method disclosed herein without departing from the scope of the present invention. Accordingly, it is not intended that the invention be limited, except as by the appended claims.

What is claimed:

1. An embolic protection device for capturing embolic debris released into a body vessel of a patient, comprising:

a shaft member having a distal and a proximal end;

a filtering assembly mounted on the shaft member, the filtering assembly including an expandable strut assembly and a filter attached to the strut assembly for capturing embolic debris, the expandable strut assembly having a set of proximal struts, each strut having a first end and a second end; and a deployment member having a pattern of alternating peaks and valleys in a wave-like pattern, each of the first ends of the struts being attached to the peak portions of the deployment member, the filter element being attached to the deployment member and having a filter edge having alternating peaks and valleys in a wave-like pattern corresponding to the pattern of the deployment member, the filter element being moveable with the struts and deployment member so that at least a portion thereof contacts the wall of the vessel to capture embolic debris released into the body vessel, wherein the second end of each of the struts is attached to a proximal collar placed between a proximal stop element and a distal stop element attached to the shaft member for preventing axial movement of the proximal collar along the shaft member.

2. The embolic protection device of claim 1, wherein:

the filtering assembly is rotatably mounted onto the shaft member.

3. The embolic protection device of claim 1, wherein:

the set of struts and deployment member are made from a segment of tubing made from a self-expanding material which is laser cut to form the individual struts and deployment member.

4. The embolic protection device of claim 3, wherein:

the alternating peaks and valleys forming the wave-like pattern of the deployment member are substantially V-shaped.

5. The embolic protection device of claim 1, further including a layer of polymeric material deposited on the proximal struts, the layer of polymeric material having a coefficient of friction less than the coefficient of friction of the material forming the strut assembly.

6. The embolic protection device of claim 5, wherein the polymeric material is selected from the group consisting of PTFE and polyimide.

7. The embolic protection device of claim 1, further including a layer of heparin deposited on the filtering element.

8. The embolic protection device of claim 1, further including a layer of polymeric material selectively deposited on the strut assembly.

* * * * *

UNITED STATES PATENT AND TRADEMARK OFFICE
CERTIFICATE OF CORRECTION

PATENT NO. : 6,702,834 B1
DATED : March 9, 2004
INVENTOR(S) : John F. Boylan et al.

It is certified that error appears in the above-identified patent and that said Letters Patent is hereby corrected as shown below:

Title page,
Item [75], Inventors, delete:
"Francisco Sanchez, Temecula, CA(US);
Debashis Dutta, Santa Clara, CA (US);
Samir Patel, Del Mar, CA (US);
Chicheng Wang, Highland Park, CA (US);
Paul F. Muller, San Carlos, CA (US)."

Column 5,
Line 38, delete "way" and insert -- ways --.

Column 6,
Line 19, delete "triangle" and insert -- triangles --.
Line 27, delete "collapsed" and insert -- collapse --.

Column 17,
Line 7, delete "14" and insert -- 1-4 --.

Column 18,
Line 5, delete "is" and insert -- it --.

Column 20,
Line 2, delete "shows" and insert -- show --.
Line 46, delete "more".
Line 57, delete "some what" and insert -- somewhat --.

Column 21,
Line 49, delete "some what" and insert -- somewhat --.

Column 23,
Line 67, delete "and".

UNITED STATES PATENT AND TRADEMARK OFFICE
CERTIFICATE OF CORRECTION

PATENT NO. : 6,702,834 B1
DATED : March 9, 2004
INVENTOR(S) : John F. Boylan et al.

It is certified that error appears in the above-identified patent and that said Letters Patent is hereby corrected as shown below:

Column 30,
Line 60, after "utilized" insert -- in --.

Column 31,
Line 20, delete "which be" and insert -- which can be --.

Column 32,
Line 40, delete "is a" and insert -- is as --.
Line 53, delete "phaseseparation" and insert -- phase separation --.

Signed and Sealed this

Twenty-first Day of September, 2004

JON W. DUDAS
*Director of the United States Patent and Trademark Office*